United States Patent [19]
Potter et al.

[11] Patent Number: 6,100,066
[45] Date of Patent: *Aug. 8, 2000

[54] **NUCLEIC ACID MOLECULES ENCODING *HAEMOPHILUS SOMNUS* PROTEINS**

[75] Inventors: Andrew A. Potter, Saskatoon, Canada; Michael Theisen, Frederiks Ber GC, Denmark; Richard J. Harland; Clement R. Rioux, both of Saskatoon, Canada

[73] Assignee: University of Saskatchewan, Saskatoon, Canada

[ * ] Notice: This patent issued on a continued prosecution application filed under 37 CFR 1.53(d), and is subject to the twenty year patent term provisions of 35 U.S.C. 154(a)(2).

[21] Appl. No.: 08/619,812

[22] Filed: Mar. 15, 1996

Related U.S. Application Data

[60] Division of application No. 08/038,719, Mar. 29, 1993, abandoned, which is a continuation-in-part of application No. 07/865,050, Apr. 9, 1992, abandoned.

[51] Int. Cl.⁷ ..................................... C12P 21/06
[52] U.S. Cl. .................. 435/69.3; 435/69.1; 435/252.3; 435/320.1; 536/23.1; 536/23.7; 536/24.32; 424/256.1
[58] Field of Search ............................. 435/69.3, 320.1, 435/252.3; 536/22.1, 23.7, 23.1, 24.32; 424/256.1

[56] References Cited

U.S. PATENT DOCUMENTS

| | | | |
|---|---|---|---|
| 4,877,613 | 10/1989 | Vedros et al. | 424/92 |
| 4,981,685 | 1/1991 | Healey | 424/92 |

OTHER PUBLICATIONS

Anderson et al., *J. Bacteriol.* (1988) 170:4493–4500.
Bessler et al., *Z. Immun.* (1977) 153:11–22.
Bessler et al., *J. Immunol.* (1985) 135:1900–1905.
Bricker et al., *Infect. Immun.* (1988) 56:295–301.
Corbeil et al., *Infect. Immun.* (1987) 55: 1381–1386.
Corbeil et al., *Infect. Immun.* (1988) 56:2736–2742.
Corbeil, *Can. J. Vet. Res.* (1990) 54:557–562.
Corbeil et al., *Infect. Immun.* (1991) 59:4295–4301.
Goglolewski et al., *Infect. Immun.* (1988) 56:2307–2316.
Hanson et al., *Mol. Microbiol.* (1991) 5:267–278.
Harland et al., *Res. Work. Admin. Dis. 71st* (1990) 29:6.
Harris et al., *Can J. Vet. Res.* (1990) 30:816–822.
Hubbard et al., *Infect. Immun.* (1991) 59:1521–1528.
Humphrey et al., *Vet. Bull.* (1983) 53:987–1004.
Melchers et al., *J. Exp. Med.* (1975) 142:473–482.
Nelson et al., *Infect. Immun.* (1988) 56:128–134.
Theisen et al., *Infect. Immun.* (1992) 60:826–831.
Theisen et al., *Infect. Immun.* (1993) 61:1793–1798.
Theisen et al., *Abstr. Gen. Meeting. Am. Soc. Microbiol.* (1992) 92:88.
Thirkell et al., *Infect. Immun.* (1991) 59:781–784.
Theisen et al Abstracts of the Gen. Meeting ASM p. 88 B–377 (Apr. 8, 1992).
Theisen et al Infect & Immunity 60: 826–831, 1992.
Sambrook et al cited by applicant.
Mulvey et al Nucleic Acids 17:9979–9991, 1989.
Stragene. 1991. Product Catalogue. p. 292.
Boehringer Manheim Biochemicals. 1991. Catalog p. 557.
New England Biolabs Catalog. 1986/7. pp. 60–62.
Gibco Catalog & Reference Guide 1992 p. 292.
Thiesen et al. Jan. 1992. J. Bacteriol. 174(1):17–23.

*Primary Examiner*—Christopher L. Chin
*Assistant Examiner*—Jennifer Graser
*Attorney, Agent, or Firm*—Robins & Associates

[57] ABSTRACT

Novel vaccines for use in the prevention and treatment of *H. somnus* infections are disclosed. The vaccines contain epitopes from LppA, LppB, LppC or combinations thereof. Also disclosed are the nucleotide sequences encoding these lipoproteins, vectors including these sequences, and host cells transformed with these vectors.

14 Claims, 17 Drawing Sheets

```
AAAAAATCCA TTGATAGCAA TCAGTTTTAT CTGAAATTGG TACAAAAAAT AATTACTATT    60

TTTAGTATGA ATACCAGTGC AGAATACTTT ACGACTAGAA CTTCGTTTAC GTCTGCCGGT   120

GATGCAGGGT TATTGGGGTG TTCCTAAAT GCCTTTGAAA ATTACCAACT GAATGAAGCG   180

TGGACTTGGG AAAAACAGGC TTTAGTTCGT TGTAGGGCGG TATACGGCGA TATTGATTTA   240

TGTGAACGCT TTGAAAAAAT TCGTTGTAAT GTGCTTTCAG CTCCAAGAAA TGTGGAACAG   300

CTGAAGCAAG ATATACGAGA GATGCGTCAA AAAATGTATC ATCATCTCTC TAAACATAAA   360

ACGGACGAAT TTAATATTAA GACTGATTTG GGCGGTATCA CAGATATTGA GTTTATTGCA   420

CAATACTTAG TTTTAGCTTA TGCTCCCCAA CACTAGCATT AACACGTTGG TCTGATAATG   480

TAGGATATTT GACTGTATGG CTGAAAGTGC GGTGATTTCA CAAGAAGTTT CCACAAAGTC   540

AAAAAAATGC TATGTAAATT TACGAAACCA AATTCATCAT TTAAATTTAT TAGGTCAAGA   600

ACCGATTATT AATGCACAAC TATTTAGCAA GGAAAGAACG TTTATTCTCA ATACATGGAA   660

AAGTTTATTG GAATGAATGA ACTTATAATT GCCCTAAAAT CAGCATATGA TAAGAAATTA   720

TTTATCATTT GTATTTTCTT TGTTATGCTA TGCAGACCTT TAACTTACAT TAACAAATGA   780

GAAATAAACG ATG AAA TTA AAT AAA TCA CTT TTG GTC GGC ACA TTA GTC      829
            Met Lys Leu Asn Lys Ser Leu Leu Val Gly Thr Leu Val
             1               5                  10

GCC TCA ACT GTA TTA TTA GCA GCT TGT AAT GAA AAA AAT AAA GCG GAA     877
Ala Ser Thr Val Leu Leu Ala Ala Cys Asn Glu Lys Asn Lys Ala Glu
 15                  20                  25

ACA ACG CCA ACT GAA CCG GTT ACA GTT GCA GAA ACT CAA GCT CAA CCT     925
Thr Thr Pro Thr Glu Pro Val Thr Val Ala Glu Thr Gln Ala Gln Pro
 30                  35                  40                  45

GAC GTT CAA GGA AAA ACT GAA ACA ACT TCA TCT GAA TCA ACC GCA ATT     973
Asp Val Gln Gly Lys Thr Glu Thr Thr Ser Ser Glu Ser Thr Ala Ile
                 50                  55                  60

GAA AAT ACA CAA TCT GAT GCT CAA GAA AAA ACT GAG ACA ACT TCA GTT    1021
Glu Asn Thr Gln Ser Asp Ala Gln Glu Lys Thr Glu Thr Thr Ser Val
                 65                  70                  75

GAA ACA ACC TCG ACT GAA CCA ACC GCA GCT GGA AAC ACA CAA CCT GAA    1069
Glu Thr Thr Ser Thr Glu Pro Thr Ala Ala Gly Asn Thr Gln Pro Glu
         80                  85                  90

TCT CAA GAA AAA GTT GTT TCA GAA AAA AGT GAG ACA GTT GTT CAA GAA    1117
Ser Gln Glu Lys Val Val Ser Glu Lys Ser Glu Thr Val Val Gln Glu
         95                 100                 105

ATT CTT AAT CAG TTT AAC AAT ACA GTT ACG ATC CAA TTG GTG GGG TAT    1165
Ile Leu Asn Gln Phe Asn Asn Thr Val Thr Ile Gln Leu Val Gly Tyr
110                 115                 120                 125
```

*FIG. 1A*

```
CAG AGT GAA AAA ATA GAG GGT GAA GAT ACT TTA TCT TTC GTT TAT AAC    1213
Gln Ser Glu Lys Ile Glu Gly Glu Asp Thr Leu Ser Phe Val Tyr Asn
            130                 135                 140

GTT AAG AAT AAA GGT GAT AAA GCA ATC AAA GAA CTT CAG TGG TAT AAC    1261
Val Lys Asn Lys Gly Asp Lys Ala Ile Lys Glu Leu Gln Trp Tyr Asn
            145                 150                 155

CTT GTT TTC TTT AAT TCG ACT CTG GTA GAG CCT CTT TCA ATA GCC TAT    1309
Leu Val Phe Phe Asn Ser Thr Leu Val Glu Pro Leu Ser Ile Ala Tyr
            160                 165                 170

TCT TTT GAG GAT ACG CTT GCT CCG GAA GGC GAG GGC GAA ATA AAA TTA    1357
Ser Phe Glu Asp Thr Leu Ala Pro Glu Gly Glu Gly Glu Ile Lys Leu
        175                 180                 185

ACA AAA TTA GCT AAA ACT TAT GCT GAA GAG ATT CGT GCA GAT ATA CTA    1405
Thr Lys Leu Ala Lys Thr Tyr Ala Glu Glu Ile Arg Ala Asp Ile Leu
190             195                 200                 205

AAA CCG GAA GCT AAT CTT CAA TTT AGC CCA ATA ATT GCA GGT CGA ATT    1453
Lys Pro Glu Ala Asn Leu Gln Phe Ser Pro Ile Ile Ala Gly Arg Ile
                210                 215                 220

ATT TTT GAA GAC GGT ACG CAA TTA GTT GTA ACT ACA GAT GAA GAG CTT    1501
Ile Phe Glu Asp Gly Thr Gln Leu Val Val Thr Thr Asp Glu Glu Leu
                225                 230                 235

ACT CAA TCT TTA CAG CAA ATT TTA ACG CAA TAATTTTTAA AAATAATTAT      1551
Thr Gln Ser Leu Gln Gln Ile Leu Thr Gln
            240                 245

TCAACGCATT AGTTATCTAT CCGCTCTTAC AAATCTATAA TATTTATAAA TAACTACAAA  1611

AAGTTATCAA TAAGATTTTA TAGATTGGTA AGATCGGTTA TGTTTCCGCA TCGAAATCTA  1671

CTGCCCATTA TTGGCGAAAC CGAAAGAAAT TCGTCGTAAA AAGCGTGCAG AGCAACAAGA  1731

AAAAGAAGTG TGAAGAAAAA AAGCTGAGAA TTTGCTAAAA ATCAGCTCAA CAAACCGCAC  1791

TTTAATAATA AAAATTTCTG CGAGAAATCA TGTAAAAAAA ATAACACCCT CTTAACAAGA  1851

AGAGGGTGAA TAATCAATTT ACCATTGGTA CCCTATAGAA ACTGAACCTG CCATTTTGCC  1911

TTGAGAATTT CTATTTCCTT GAAATTTAAG CATAATCTTA CGTTATCACT CATACGAGAA  1971

TAACCAATCG CCAT                                                   1985
```

FIG. 1B

```
CGACGCCAGT GCCAAGCTTG CATGCCTGCA GGTGATCTAA GCTTCCCGGG ATCCAAGAGG    60
TGAAGAGATT TATTGGATTG GACCAATAGG ACTGGCAGAA AATGAATCGG AAGGAACGGA   120
CTTCCATGCC GTTAAAAACG GCTATGTGTC AATTACACCC ATTCAAACAG ATATGACGGC   180
ATATCATTCA ATGACAGCTT TACAACAATG GTTAGATAAG GAATAACGAT AATCTTTTCA   240
TCGAAGGAAT AAAACATGAA AATTTTCGGT ACGCTATATG ATAAAACTAT GCAATGGGCA   300
AATCACCGTT TTGCTACATT TTGGCTAACT TTTGTTAGTT TTATTGAGGC TATTTCTTC    360
CCAATACCAC CTGATGTCAT GCTTATTCCG ATGTCAATAA ATAAACCTAA ATGTGCTACT   420
AAATTTGCAT TTTATGCAGC AATGGCTTCA GCCATTGGTG GGCAATTGG TTATGGATTA    480
GGTTATTACG CTTTTGATTT CATACAAAGT TATATTCAAC AATGGGGTTA TCAACAACAT   540
TGGGAAACTG CTCTTTCTTG GTTCAAAGAA TGGGGTATTT GGGTAGTTTT CGTTGCAGGT   600
TTTTCACCTA TTCCTTATAA AATTTTTACG ATTTGTGCAG GCGTCATGCA AATGGCATTT   660
TTGCCTTTCT TACTTACTGC CTTTATTTCT CGTATTGCAA GATTTTTGCT CGTTACCCAT   720
TTAGCGGCTT GGAGCGGAAA AAAATTTGCT GCGAAATTAC GTCAATCTAT TGAATTTATC   780
GGTTGGTCAG TTGTCATTAT TGCTATAGTT GTATATCTTG TCTTGAAATA ATCTAAGATA   840
AAAAATGAAT ATAAAGTAAC GGAGAATTTA C ATG AAA AAA TTT TTA CCT TTA      892
                                 Met Lys Lys Phe Leu Pro Leu
                                  1               5

TCT ATT AGT ATC ACT GTA CTA GCT GCT TGT AGT TCA CAC ACT CCG GCT     940
Ser Ile Ser Ile Thr Val Leu Ala Ala Cys Ser Ser His Thr Pro Ala
         10              15                  20

CCG GTA GAA AAT GCT AAG GAT TTA GCA CCA AGT ATT ATC AAA CCG ATT     988
Pro Val Glu Asn Ala Lys Asp Leu Ala Pro Ser Ile Ile Lys Pro Ile
     25              30                  35

AAT GGT ACA AAC TCA ACC GCT TGG GAA CCT CAA GTT ATT CAA CAA AAG    1036
Asn Gly Thr Asn Ser Thr Ala Trp Glu Pro Gln Val Ile Gln Gln Lys
 40              45                  50                  55

ATG CCC GAA AGT ATG AGA GTG CCG AAA GCA ACA AAC TCC ACT TAT CAA    1084
Met Pro Glu Ser Met Arg Val Pro Lys Ala Thr Asn Ser Thr Tyr Gln
             60                  65                  70

CCT GAA ATC ATT CAA CAA AAT CAA CAA AAA ACA GAA TCG ATA GCA AAA    1132
Pro Glu Ile Ile Gln Gln Asn Gln Gln Lys Thr Glu Ser Ile Ala Lys
                 75                  80                  85

AAA CAG GCT CTA CAA AAT TTT GAA ATT CCA AGA GAT CCT AAA ACT AAT    1180
Lys Gln Ala Leu Gln Asn Phe Glu Ile Pro Arg Asp Pro Lys Thr Asn
             90                  95                 100

GTG CCT GTT TAT AGC AAA ATT GAT AAG GGT TTT TAC AAA GGT GAT ACT    1228
Val Pro Val Tyr Ser Lys Ile Asp Lys Gly Phe Tyr Lys Gly Asp Thr
    105                 110                 115

TAC AAA GTA CGC AAA GGC GAT ACC ATG TTT CTT ATT GCT TAT ATT TCA    1276
Tyr Lys Val Arg Lys Gly Asp Thr Met Phe Leu Ile Ala Tyr Ile Ser
120                 125                 130                 135

GGC ATG GAT ATA AAA GAA TTG GCC ACA CTA AAT AAT ATG TCT GAG CCA    1324
Gly Met Asp Ile Lys Glu Leu Ala Thr Leu Asn Asn Met Ser Glu Pro
            140                 145                 150
```

*FIG. 3A*

| | |
|---|---|
| TAT CAT CTG AGT ATT GGA CAA GTA TTG AAA ATT GCA AAT AAT ATT CCC<br>Tyr His Leu Ser Ile Gly Gln Val Leu Lys Ile Ala Asn Asn Ile Pro<br>    155             160             165 | 1372 |
| GAT AGC AAT ATG ATA CCA ACA CAG ACA ATA AAT GAA TCA GAG GTG ACA<br>Asp Ser Asn Met Ile Pro Thr Gln Thr Ile Asn Glu Ser Glu Val Thr<br>    170             175             180 | 1420 |
| CAA AAT ACA GTC AAT GAG ACA TGG AAT GCT AAT AAA CCA ACA AAT GAA<br>Gln Asn Thr Val Asn Glu Thr Trp Asn Ala Asn Lys Pro Thr Asn Glu<br>    185             190             195 | 1468 |
| CAA ATG AAA CCC GTT GCT ACA CCA ACA CAT TCA ACA ATG CCA ATC AAT<br>Gln Met Lys Pro Val Ala Thr Pro Thr His Ser Thr Met Pro Ile Asn<br>200             205             210             215 | 1516 |
| AAA ACA CCT CCA GCC ACC TCA AAT ATA GCT TGG ATT TGG CCA ACA AAT<br>Lys Thr Pro Pro Ala Thr Ser Asn Ile Ala Trp Ile Trp Pro Thr Asn<br>    220             225             230 | 1564 |
| GGA AAA ATT ATT CAA GGA TTT TCC AGT GCT GAT GGA GGC AAT AAA GGT<br>Gly Lys Ile Ile Gln Gly Phe Ser Ser Ala Asp Gly Gly Asn Lys Gly<br>    235             240             245 | 1612 |
| ATT GAT ATT AGC GGT TCT CGT GGA CAA GCT GTT AAT GCA GCA GCT GCA<br>Ile Asp Ile Ser Gly Ser Arg Gly Gln Ala Val Asn Ala Ala Ala Ala<br>    250             255             260 | 1660 |
| TGG ACG CAG TTG TAT ATG CCG GAG ACG CTT TAC GTG GAT ATG GTA ATT<br>Trp Thr Gln Leu Tyr Met Pro Glu Thr Leu Tyr Val Asp Met Val Ile<br>    265             270             275 | 1708 |
| TAATTATTAT TAAACATAAT GACAGTTATT TAAGTGCTTA TGCACATAAT GAAAGTATAC | 1768 |
| TCGTCAAAGA TCAGCAAGAA GTTAAAGCGG GTCAACAAAT TGCTAAAATG GGAAGTTCTG | 1828 |
| GAACAAACAC AATCAAACTC CATTTAAAT TCGTTATTTT GGTCAATCAG TAGATCC | 1885 |

FIG. 3B

| | | |
|---|---|---|
| TTTAATACGA CTCACTATAG GGAATTCGAG TCGATCTAAG CTTCCCGGGG ATCACCGTGC | | 60 |

ATTTTACATT GCACATACTC AAGGAGCAAT TTATGTTATC TATTTTA ATG CAA GGT    116
                                                   Met Gln Gly
                                                    1

TTA CGC TTA AAA AAA TGC TTT CTC CCG ATT TTA GTT ATG TTT TTT TTA    164
Leu Arg Leu Lys Lys Cys Phe Leu Pro Ile Leu Val Met Phe Phe Leu
         5              10              15

GCA GGC TGT GTC AAT TTA TTA GGC AGT AGC TTT ACG GCA AGC TTA AAA    212
Ala Gly Cys Val Asn Leu Leu Gly Ser Ser Phe Thr Ala Ser Leu Lys
 20              25              30              35

AAT GAT GCC AAT GCA AGT TCT GAT TTT TAC ATT CGG AAA ATT GAA CAA    260
Asn Asp Ala Asn Ala Ser Ser Asp Phe Tyr Ile Arg Lys Ile Glu Gln
         40              45              50

ACA CAA AAT CAA CAA GAT TTA CAA ACC TAT AAA CTT TTA GCT GCT CGA    308
Thr Gln Asn Gln Gln Asp Leu Gln Thr Tyr Lys Leu Leu Ala Ala Arg
         55              60              65

GTT TTA GTA ACA GAA AAT AAA ATC CCG CAA GCG GAA GCA TAT CTT GCT    356
Val Leu Val Thr Glu Asn Lys Ile Pro Gln Ala Glu Ala Tyr Leu Ala
         70              75              80

GAA TTG ATA GAT TTA AAT GAT GAA CAA AAA CTA GAT AAA TCC CTG ATT    404
Glu Leu Ile Asp Leu Asn Asp Glu Gln Lys Leu Asp Lys Ser Leu Ile
 85              90              95

GAA GCT CAT ATT TCT GCT GTT AAA GGC AAA AAT GAA ACG GCA GAA TAT    452
Glu Ala His Ile Ser Ala Val Lys Gly Lys Asn Glu Thr Ala Glu Tyr
100             105             110             115

CAA TTA TCT TTA ATT CAC TTG ACA TTA CTT AGT CCT TCA CAA AAA TCA    500
Gln Leu Ser Leu Ile His Leu Thr Leu Leu Ser Pro Ser Gln Lys Ser
             120             125             130

CGT TAT TAT GAG ATT GTT TCT CGT ATT GCA GAA AAT CGT CAT GAT AAT    548
Arg Tyr Tyr Glu Ile Val Ser Arg Ile Ala Glu Asn Arg His Asp Asn
             135             140             145

ATT TCA GCG ATA AAA GCT CGA ATT CAA ATG GAT AAT TTT TTA AGT GAT    596
Ile Ser Ala Ile Lys Ala Arg Ile Gln Met Asp Asn Phe Leu Ser Asp
             150             155             160

ATT CAA CGA AAA CAA CAA AAT AAT GAC CGC ACT TGG GCA TTG CTA CGC    644
Ile Gln Arg Lys Gln Gln Asn Asn Asp Arg Thr Trp Ala Leu Leu Arg
             165             170             175

AAT ACA GAT AGT GAA GTA CTA AAT AAT ACT GAT GCG GAA GGA AAT ATT    692
Asn Thr Asp Ser Glu Val Leu Asn Asn Thr Asp Ala Glu Gly Asn Ile
180             185             190             195

ACA TTG AGC GGT TGG TTA ACA TTA GCT CAA CTA TAC AAT GAT AAC CTT    740
Thr Leu Ser Gly Trp Leu Thr Leu Ala Gln Leu Tyr Asn Asp Asn Leu
             200             205             210

AAT CAA CCT GCA CAA TTA ATT CAA ACA TTA CTG ACT TGG AAA AAT TAT    788
Asn Gln Pro Ala Gln Leu Ile Gln Thr Leu Leu Thr Trp Lys Asn Tyr
             215             220             225

FIG. 4A

```
TAT CCA ACA CAT ACG GCA GCA CAT TTA TTA CCT ACA GAA TTA CAA GGG         836
Tyr Pro Thr His Thr Ala Ala His Leu Leu Pro Thr Glu Leu Gln Gly
        230             235             240

CTT GCC AAT TTT CAA CAA ACT ACT TTA ACG CAA GTC GGT CTA ATA CTC         884
Leu Ala Asn Phe Gln Gln Thr Thr Leu Thr Gln Val Gly Leu Ile Leu
        245             250             255

CCT TTA AGC GGC AAT ACA CGA CTT ATC GGT GAA ACA ATC AAA AAC GGG         932
Pro Leu Ser Gly Asn Thr Arg Leu Ile Gly Glu Thr Ile Lys Asn Gly
260             265             270             275

TTT GAT GAT GCC AAA GTC AAT TAC AAT GTT CAA GTT CAC GTA TTT GAC         980
Phe Asp Asp Ala Lys Val Asn Tyr Asn Val Gln Val His Val Phe Asp
            280             285             290

TCA ATG AAA ATG TCT ATA GAA CAA ATT ATT AAT CAA GCA AAA AAA CAG        1028
Ser Met Lys Met Ser Ile Glu Gln Ile Ile Asn Gln Ala Lys Lys Gln
            295             300             305

GGA ATT AAC ACT CTT GTC GGA CCA TTA CTC AAA CAA AAT GTT GAT GTT        1076
Gly Ile Asn Thr Leu Val Gly Pro Leu Leu Lys Gln Asn Val Asp Val
            310             315             320

ATA GTC AAT AAT CCG TAT TTG GTA CAA GAT TTA AAT GTA TTA GCG TTG        1124
Ile Val Asn Asn Pro Tyr Leu Val Gln Asp Leu Asn Val Leu Ala Leu
325             330             335

AAC TCT ACG CCT AAT GCA CGG GCA ATT GAA CAC CTT TGT TAT TAT GGA        1172
Asn Ser Thr Pro Asn Ala Arg Ala Ile Glu His Leu Cys Tyr Tyr Gly
340             345             350             355

TTA TCG CCT GAA GAT GAA GCT GAA AGT GCG GCA AGT AAA ATG TGG AAT        1220
Leu Ser Pro Glu Asp Glu Ala Glu Ser Ala Ala Ser Lys Met Trp Asn
            360             365             370

GAT GCA GTA CGT ATT CCA CTT GTT TTA GTA CCG CAA AAT AAT CTG GGG        1268
Asp Ala Val Arg Ile Pro Leu Val Leu Val Pro Gln Asn Asn Leu Gly
            375             380             385

CGA CGC ACG GCA GCG GCA TTT ACT CTA CGT TGG CAA CAA CTA TTG GGT        1316
Arg Arg Thr Ala Ala Ala Phe Thr Leu Arg Trp Gln Gln Leu Leu Gly
        390             395             400

ACT GAT GCC AAT ATT AAA TTC TAT AAT CAA ACC GCA GAT ATT AAT TTT        1364
Thr Asp Ala Asn Ile Lys Phe Tyr Asn Gln Thr Ala Asp Ile Asn Phe
        405             410             415

GCA TTA AAA TCG GGG TTA AGT GAA AGT ACT GAC GGC GTG TAT ATT ATT        1412
Ala Leu Lys Ser Gly Leu Ser Glu Ser Thr Asp Gly Val Tyr Ile Ile
420             425             430             435

GCT AAT AAC AAA CAA TTA GCT GAA ATT AAA GCA GTG TTG GAT AAT ATT        1460
Ala Asn Asn Lys Gln Leu Ala Glu Ile Lys Ala Val Leu Asp Asn Ile
            440             445             450

AAT CCG ACC CTA AAA CTT TAT GCA AGT TCA CGT AGT AAT TCG CCT AAC        1508
Asn Pro Thr Leu Lys Leu Tyr Ala Ser Ser Arg Ser Asn Ser Pro Asn
        455             460             465
```

*FIG. 4B*

| | | | | | | | | | | | | | | | | |
|---|---|---|---|---|---|---|---|---|---|---|---|---|---|---|---|---|
| AGT | GGT | CCT | GAA | CAT | CGT | TTG | TTT | CTG | AAT | AAT | CTG | CAA | TTT | AGT | GAT | 1556 |
| Ser | Gly | Pro | Glu | His | Arg | Leu | Phe | Leu | Asn | Asn | Leu | Gln | Phe | Ser | Asp | |
| | | 470 | | | | | 475 | | | | 480 | | | | | |
| ATT | CCG | TTC | TTC | AAA | GAT | AGG | GAA | TCG | GAA | CAA | TAT | AAA | AAA | ATT | GAA | 1604 |
| Ile | Pro | Phe | Phe | Lys | Asp | Arg | Glu | Ser | Glu | Gln | Tyr | Lys | Lys | Ile | Glu | |
| | 485 | | | | | 490 | | | | | 495 | | | | | |
| AAA | ATG | ACC | AAT | AAT | GAT | TAC | TCA | TTA | ATG | CAT | TTA | TAT | GCT | ATG | GGT | 1652 |
| Lys | Met | Thr | Asn | Asn | Asp | Tyr | Ser | Leu | Met | His | Leu | Tyr | Ala | Met | Gly | |
| 500 | | | | | 505 | | | | 510 | | | | | 515 | | |
| TAT | GAT | GCT | TGG | TTA | TTA | ATA | AAT | CAA | TTT | AAT | GAA | TTC | CGT | CAA | ATT | 1700 |
| Tyr | Asp | Ala | Trp | Leu | Leu | Ile | Asn | Gln | Phe | Asn | Glu | Phe | Arg | Gln | Ile | |
| | | | | 520 | | | | 525 | | | | | 530 | | | |
| CCC | GGA | TTT | ACC | ATT | GAT | GGG | TTA | ACA | GGA | AAA | CTC | AGT | GCC | GGC | CCT | 1748 |
| Pro | Gly | Phe | Thr | Ile | Asp | Gly | Leu | Thr | Gly | Lys | Leu | Ser | Ala | Gly | Pro | |
| | | | 535 | | | | | 540 | | | | | 545 | | | |
| AAC | TGT | AAT | GTT | GAA | CGT | GAT | ATG | ACT | TGG | TTC | CAA | TAT | CAA | AAT | GGC | 1796 |
| Asn | Cys | Asn | Val | Glu | Arg | Asp | Met | Thr | Trp | Phe | Gln | Tyr | Gln | Asn | Gly | |
| | | 550 | | | | | 555 | | | | | 560 | | | | |
| AGT | ATC | TAT | CCG | CTT | AAC | GAG | CAA | GAT | GAC | AGC | ATC | TAT | CTG | ATT | AAC | 1844 |
| Ser | Ile | Tyr | Pro | Leu | Asn | Glu | Gln | Asp | Asp | Ser | Ile | Tyr | Leu | Ile | Asn | |
| | 565 | | | | | 570 | | | | | 575 | | | | | |

| | | | | |
|---|---|---|---|---|
| GAA GAA TGATACAATC CAAACGTCAA CAAGGTGCGA GTTTTGAATA TCAGGCTCGC | | | | | 1900 |
| Glu Glu | | | | |
| 580 | | | | |
| CTCTTTTTAG | AGAGACAAGG | TTTAACCTTT | ATTGCAGCTA | ACCAACGCTT TAACTGCGGT | 1960 |
| GAATTGGATT | TGATTATGCA | AGATCGGCAA | ACGATCGTTT | TGTTGAGGT TCGTCAGCGT | 2020 |
| AAAAATCAAA | TTTTCGGTTC | AGCAATTGAC | AGTGTAGATT | GGAAAAAGCA GCAAAAATGG | 2080 |
| CTTGATGCAG | CCAACCTATG | GTTAGCACAA | TATGATTCCA | GTTTAGAAGA TGCGGACTGC | 2140 |
| CGTTTCGATC | TGGTCGCTTT | TGGAGCAACA | ACAAATGATA | TCCAATGGAT ACCTAATTTT | 2200 |
| CTTGATGAAT | AAAAATTATG | AAAAAGTTAA | AGATATTTAT | ACGGAAAGTA TTCAAACTCA | 2260 |
| AATTTCTTCC | TCCAGCTTAC | TTGCAACAAA | AATCGTAGAG | GCAACTCAAC ATATTGTAAA | 2320 |
| TTGCCTGCTG | AAAGGTAATA | AAATTATTGT | CTGTGGGCAT | GGTAGATCCT AGCTAGCTAG | 2380 |
| CCATGGACCT | GCAGGCATGC | AAGCTTGGCA | CTGAGTCGTT | CGTTTTTACA ACGTTCGTTG | 2440 |
| ACTGGGAAAA | CCCTGGTCCG | TTTAG | | | 2465 |

*FIG. 4C*

```
            10          20          30          40          50
        *       *       *       *       *       *       *       *       *       *
ATG GCT ACT GTT ATA GAT CTA AGC TTC CCA AAA ACT GGG GCA AAA AAA ATT
TAC CGA TGA CAA TAT CTA GAT TCG AAG GGT TTT TGA CCC CGT TTT TTT TAA
Met Ala Thr Val Ile Asp Leu Ser Phe Pro Lys Thr Gly Ala Lys Lys Ile>
 __b___b___b___b___b___b____LEUKOTOXIN_b___b___b___b___b___b___b__>

60          70          80          90          100
        *       *       *       *       *       *       *       *       *       *
ATC CTC TAT ATT CCC CAA AAT TAC CAA TAT GAT ACT GAA CAA GGT AAT GGT
TAG GAG ATA TAA GGG GTT TTA ATG GTT ATA CTA TGA CTT GTT CCA TTA CCA
Ile Leu Tyr Ile Pro Gln Asn Tyr Gln Tyr Asp Thr Glu Gln Gly Asn Gly>
 __b___b___b___b___b___b____LEUKOTOXIN_b___b___b___b___b___b___b__>

110         120         130         140         150
        *       *       *       *       *       *       *       *       *       *
TTA CAG GAT TTA GTC AAA GCG GCC GAA GAG TTG GGG ATT GAG GTA CAA AGA
AAT GTC CTA AAT CAG TTT CGC CGG CTT CTC AAC CCC TAA CTC CAT GTT TCT
Leu Gln Asp Leu Val Lys Ala Ala Glu Glu Leu Gly Ile Glu Val Gln Arg>
 __b___b___b___b___b___b____LEUKOTOXIN_b___b___b___b___b___b___b__>

160         170         180         190         200
        *       *       *       *       *       *       *       *       *       *
GAA GAA CGC AAT AAT ATT GCA ACA GCT CAA ACC AGT TTA GGC ACG ATT CAA
CTT CTT GCG TTA TTA TAA CGT TGT CGA GTT TGG TCA AAT CCG TGC TAA GTT
Glu Glu Arg Asn Asn Ile Ala Thr Ala Gln Thr Ser Leu Gly Thr Ile Gln>
 __b___b___b___b___b___b____LEUKOTOXIN_b___b___b___b___b___b___b__>

210         220         230         240         250
        *       *       *       *       *       *       *       *       *       *
ACC GCT ATT GGC TTA ACT GAG CGT GGC ATT GTG TTA TCC GCT CCA CAA ATT
TGG CGA TAA CCG AAT TGA CTC GCA CCG TAA CAC AAT AGG CGA GGT GTT TAA
Thr Ala Ile Gly Leu Thr Glu Arg Gly Ile Val Leu Ser Ala Pro Gln Ile>
 __b___b___b___b___b___b____LEUKOTOXIN_b___b___b___b___b___b___b__>

260         270         280         290         300
        *       *       *       *       *       *       *       *       *       *
GAT AAA TTG CTA CAG AAA ACT AAA GCA GGC CAA GCA TTA GGT TCT GCC GAA
CTA TTT AAC GAT GTC TTT TGA TTT CGT CCG GTT CGT AAT CCA AGA CGG CTT
Asp Lys Leu Leu Gln Lys Thr Lys Ala Gly Gln Ala Leu Gly Ser Ala Glu>
 __b___b___b___b___b___b____LEUKOTOXIN_b___b___b___b___b___b___b__>

310         320         330         340         350
        *       *       *       *       *       *       *       *       *       *
AGC ATT GTA CAA AAT GCA AAT AAA GCC AAA ACT GTA TTA TCT GGC ATT CAA
TCG TAA CAT GTT TTA CGT TTA TTT CGG TTT TGA CAT AAT AGA CCG TAA GTT
Ser Ile Val Gln Asn Ala Asn Lys Ala Lys Thr Val Leu Ser Gly Ile Gln>
 __b___b___b___b___b___b____LEUKOTOXIN_b___b___b___b___b___b___b__>

360         370         380         390         400
        *       *       *       *       *       *       *       *       *       *
TCT ATT TTA GGC TCA GTA TTG GCT GGA ATG GAT TTA GAT GAG GCC TTA CAG
AGA TAA AAT CCG AGT CAT AAC CGA CCT TAC CTA AAT CTA CTC CGG AAT GTC
Ser Ile Leu Gly Ser Val Leu Ala Gly Met Asp Leu Asp Glu Ala Leu Gln>
 __b___b___b___b___b___b____LEUKOTOXIN_b___b___b___b___b___b___b__>
```

*FIG. 5A*

```
       410           420           430           440           450
        *     *       *     *       *     *       *     *       *     *
       AAT AAC AGC AAC CAA CAT GCT CTT GCT AAA GCT GGC TTG GAG CTA ACA AAT
       TTA TTG TCG TTG GTT GTA CGA GAA CGA TTT CGA CCG AAC CTC GAT TGT TTA
       Asn Asn Ser Asn Gln His Ala Leu Ala Lys Ala Gly Leu Glu Leu Thr Asn>
       __b___b___b___b___b___b____LEUKOTOXIN_b___b___b___b___b___b___b___>

460           470           480           490           500           510
        *     *       *     *       *     *       *     *       *     *       *
       TCA TTA ATT GAA AAT ATT GCT AAT TCA GTA AAA ACA CTT GAC GAA TTT GGT
       AGT AAT TAA CTT TTA TAA CGA TTA AGT CAT TTT TGT GAA CTG CTT AAA CCA
       Ser Leu Ile Glu Asn Ile Ala Asn Ser Val Lys Thr Leu Asp Glu Phe Gly>
       __b___b___b___b___b___b____LEUKOTOXIN_b___b___b___b___b___b___b___>

520           530           540           550           560
              *     *       *     *       *     *       *     *       *
             GAG CAA ATT AGT CAA TTT GGT TCA AAA CTA CAA AAT ATC AAA GGC TTA GGG
             CTC GTT TAA TCA GTT AAA CCA AGT TTT GAT GTT TTA TAG TTT CCG AAT CCC
             Glu Gln Ile Ser Gln Phe Gly Ser Lys Leu Gln Asn Ile Lys Gly Leu Gly>
             __b___b___b___b___b___b____LEUKOTOXIN_b___b___b___b___b___b___b___>

570           580           590           600           610
              *     *       *     *       *     *       *     *       *     *
             ACT TTA GGA GAC AAA CTC AAA AAT ATC GGT GGA CTT GAT AAA GCT GGC CTT
             TGA AAT CCT CTG TTT GAG TTT TTA TAG CCA CCT GAA CTA TTT CGA CCG GAA
             Thr Leu Gly Asp Lys Leu Lys Asn Ile Gly Gly Leu Asp Lys Ala Gly Leu>
             __b___b___b___b___b___b____LEUKOTOXIN_b___b___b___b___b___b___b___>

620           630           640           650           660
              *     *       *     *       *     *       *     *       *
             GGT TTA GAT GTT ATC TCA GGG CTA TTA TCG GGC GCA ACA GCT GCA CTT GTA
             CCA AAT CTA CAA TAG AGT CCC GAT AAT AGC CCG CGT TGT CGA CGT GAA CAT
             Gly Leu Asp Val Ile Ser Gly Leu Leu Ser Gly Ala Thr Ala Ala Leu Val>
             __b___b___b___b___b___b____LEUKOTOXIN_b___b___b___b___b___b___b___>

670           680           690           700           710
              *     *       *     *       *     *       *     *       *
             CTT GCA GAT AAA AAT GCT TCA ACA GCT AAA AAA GTG GGT GCG GGT TTT GAA
             GAA CGT CTA TTT TTA CGA AGT TGT CGA TTT TTT CAC CCA CGC CCA AAA CTT
             Leu Ala Asp Lys Asn Ala Ser Thr Ala Lys Lys Val Gly Ala Gly Phe Glu>
             __b___b___b___b___b___b____LEUKOTOXIN_b___b___b___b___b___b___b___>

720           730           740           750           760
              *     *       *     *       *     *       *     *       *     *
             TTG GCA AAC CAA GTT GTT GGT AAT ATT ACC AAA GCC GTT TCT TCT TAC ATT
             AAC CGT TTG GTT CAA CAA CCA TTA TAA TGG TTT CGG CAA AGA AGA ATG TAA
             Leu Ala Asn Gln Val Val Gly Asn Ile Thr Lys Ala Val Ser Ser Tyr Ile>
             __b___b___b___b___b___b____LEUKOTOXIN_b___b___b___b___b___b___b___>

770           780           790           800           810
              *     *       *     *       *     *       *     *       *     *
             TTA GCC CAA CGT GTT GCA GCA GGT TTA TCT TCA ACT GGG CCT GTG GCT GCT
             AAT CGG GTT GCA CAA CGT CGT CCA AAT AGA AGT TGA CCC GGA CAC CGA CGA
             Leu Ala Gln Arg Val Ala Ala Gly Leu Ser Ser Thr Gly Pro Val Ala Ala>
             __b___b___b___b___b___b____LEUKOTOXIN_b___b___b___b___b___b___b___>
```

FIG. 5B

```
       820         830         840         850         860
        *           *           *           *           *     *
TTA ATT GCT TCT ACT GTT TCT CTT GCG ATT AGC CCA TTA GCA TTT GCC GGT
AAT TAA CGA AGA TGA CAA AGA GAA CGC TAA TCG GGT AAT CGT AAA CGG CCA
Leu Ile Ala Ser Thr Val Ser Leu Ala Ile Ser Pro Leu Ala Phe Ala Gly>
 ___b___b___b___b___b___b_____LEUKOTOXIN_b___b___b___b___b___b___b___>

870         880         890         900         910
        *           *           *           *           *     *
ATT GCC GAT AAA TTT AAT CAT GCA AAA AGT TTA GAG AGT TAT GCC GAA CGC
TAA CGG CTA TTT AAA TTA GTA CGT TTT TCA AAT CTC TCA ATA CGG CTT GCG
Ile Ala Asp Lys Phe Asn His Ala Lys Ser Leu Glu Ser Tyr Ala Glu Arg>
 ___b___b___b___b___b___b_____LEUKOTOXIN_b___b___b___b___b___b___b___>

920         930         940         950         960
  *           *           *           *           *           *
TTT AAA AAA TTA GGC TAT GAC GGA GAT AAT TTA TTA GCA GAA TAT CAG CGG
AAA TTT TTT AAT CCG ATA CTG CCT CTA TTA AAT AAT CGT CTT ATA GTC GCC
Phe Lys Lys Leu Gly Tyr Asp Gly Asp Asn Leu Leu Ala Glu Tyr Gln Arg>
 ___b___b___b___b___b___b_____LEUKOTOXIN_b___b___b___b___b___b___b___>

970         980         990        1000        1010        1020
        *           *           *           *           *           *
GGA ACA GGG ACT ATT GAT GCA TCG GTT ACT GCA ATT AAT ACC GCA TTG GCC
CCT TGT CCC TGA TAA CTA CGT AGC CAA TGA CGT TAA TTA TGG CGT AAC CGG
Gly Thr Gly Thr Ile Asp Ala Ser Val Thr Ala Ile Asn Thr Ala Leu Ala>
 ___b___b___b___b___b___b_____LEUKOTOXIN_b___b___b___b___b___b___b___>

1030        1040        1050        1060        1070
            *           *           *           *           *     *
GCT ATT GCT GGT GGT GTG TCT GCT GCT GCA GCC GGC TCG GTT ATT GCT TCA
CGA TAA CGA CCA CCA CAC AGA CGA CGA CGT CGG CCG AGC CAA TAA CGA AGT
Ala Ile Ala Gly Gly Val Ser Ala Ala Ala Ala Gly Ser Val Ile Ala Ser>
 ___b___b___b___b___b___b_____LEUKOTOXIN_b___b___b___b___b___b___b___>

1080        1090        1100        1110        1120
        *           *           *           *           *     *
CCG ATT GCC TTA TTA GTA TCT GGG ATT ACC GGT GTA ATT TCT ACG ATT CTG
GGC TAA CGG AAT AAT CAT AGA CCC TAA TGG CCA CAT TAA AGA TGC TAA GAC
Pro Ile Ala Leu Leu Val Ser Gly Ile Thr Gly Val Ile Ser Thr Ile Leu>
 ___b___b___b___b___b___b_____LEUKOTOXIN_b___b___b___b___b___b___b___>

1130        1140        1150        1160        1170
        *           *           *           *           *     *
CAA TAT TCT AAA CAA GCA ATG TTT GAG CAC GTT GCA AAT AAA ATT CAT AAC
GTT ATA AGA TTT GTT CGT TAC AAA CTC GTG CAA CGT TTA TTT TAA GTA TTG
Gln Tyr Ser Lys Gln Ala Met Phe Glu His Val Ala Asn Lys Ile His Asn>
 ___b___b___b___b___b___b_____LEUKOTOXIN_b___b___b___b___b___b___b___>

1180        1190        1200        1210        1220
            *           *           *           *           *     *
AAA ATT GTA GAA TGG GAA AAA AAT AAT CAC GGT AAG AAC TAC TTT GAA AAT
TTT TAA CAT CTT ACC CTT TTT TTA TTA GTG CCA TTC TTG ATG AAA CTT TTA
Lys Ile Val Glu Trp Glu Lys Asn Asn His Gly Lys Asn Tyr Phe Glu Asn>
 ___b___b___b___b___b___b_____LEUKOTOXIN_b___b___b___b___b___b___b___>
```

FIG. 5C

```
         1230           1240           1250           1260           1270
   *       *       *       *       *       *       *       *       *       *
GGT TAC GAT GCC CGT TAT CTT GCG AAT TTA CAA GAT AAT ATG AAA TTC TTA
CCA ATG CTA CGG GCA ATA GAA CGC TTA AAT GTT CTA TTA TAC TTT AAG AAT
Gly Tyr Asp Ala Arg Tyr Leu Ala Asn Leu Gln Asp Asn Met Lys Phe Leu>
___b___b___b___b___b___b_____LEUKOTOXIN_b___b___b___b___b___b___b___>

1280           1290           1300           1310           1320
   *       *       *       *       *       *       *       *       *       *
CTG AAC TTA AAC AAA GAG TTA CAG GCA GAA CGT GTC ATC GCT ATT ACT CAG
GAC TTG AAT TTG TTT CTC AAT GTC CGT CTT GCA CAG TAG CGA TAA TGA GTC
Leu Asn Leu Asn Lys Glu Leu Gln Ala Glu Arg Val Ile Ala Ile Thr Gln>
___b___b___b___b___b___b_____LEUKOTOXIN_b___b___b___b___b___b___b___>

1330           1340           1350           1360           1370
   *       *       *       *       *       *       *       *       *       *
CAG CAA TGG GAT AAC AAC ATT GGT GAT TTA GCT GGT ATT AGC CGT TTA GGT
GTC GTT ACC CTA TTG TTG TAA CCA CTA AAT CGA CCA TAA TCG GCA AAT CCA
Gln Gln Trp Asp Asn Asn Ile Gly Asp Leu Ala Gly Ile Ser Arg Leu Gly>
___b___b___b___b___b___b_____LEUKOTOXIN_b___b___b___b___b___b___b___>

1380           1390           1400           1410           1420
   *       *       *       *       *       *       *       *       *       *
GAA AAA GTC CTT AGT GGT AAA GCC TAT GTG GAT GCG TTT GAA GAA GGC AAA
CTT TTT CAG GAA TCA CCA TTT CGG ATA CAC CTA CGC AAA CTT CTT CCG TTT
Glu Lys Val Leu Ser Gly Lys Ala Tyr Val Asp Ala Phe Glu Glu Gly Lys>
___b___b___b___b___b___b_____LEUKOTOXIN_b___b___b___b___b___b___b___>

1430           1440           1450           1460           1470
   *       *       *       *       *       *       *       *       *       *
CAC ATT AAA GCC GAT AAA TTA GTA CAG TTG GAT TCG GCA AAC GGT ATT ATT
GTG TAA TTT CGG CTA TTT AAT CAT GTC AAC CTA AGC CGT TTG CCA TAA TAA
His Ile Lys Ala Asp Lys Leu Val Gln Leu Asp Ser Ala Asn Gly Ile Ile>
___b___b___b___b___b___b_____LEUKOTOXIN_b___b___b___b___b___b___b___>

1480           1490           1500           1510           1520           1530
   *       *       *       *       *       *       *       *       *       *       *
GAT GTG AGT AAT TCG GGT AAA GCG AAA ACT CAG CAT ATC TTA TTC AGA ACG
CTA CAC TCA TTA AGC CCA TTT CGC TTT TGA GTC GTA TAG AAT AAG TCT TGC
Asp Val Ser Asn Ser Gly Lys Ala Lys Thr Gln His Ile Leu Phe Arg Thr>
___b___b___b___b___b___b_____LEUKOTOXIN_b___b___b___b___b___b___b___>

1540           1550           1560           1570           1580
   *       *       *       *       *       *       *       *       *       *
CCA TTA TTG ACG CCG GGA ACA GAG CAT CGT GAA CGC GTA CAA ACA GGT AAA
GGT AAT AAC TGC GGC CCT TGT CTC GTA GCA CTT GCG CAT GTT TGT CCA TTT
Pro Leu Leu Thr Pro Gly Thr Glu His Arg Glu Arg Val Gln Thr Gly Lys>
___b___b___b___b___b___b_____LEUKOTOXIN_b___b___b___b___b___b___b___>

1590           1600           1610           1620           1630
   *       *       *       *       *       *       *       *       *       *
TAT GAA TAT ATT ACC AAG CTC AAT ATT AAC CGT GTA GAT AGC TGG AAA ATT
ATA CTT ATA TAA TGG TTC GAG TTA TAA TTG GCA CAT CTA TCG ACC TTT TAA
Tyr Glu Tyr Ile Thr Lys Leu Asn Ile Asn Arg Val Asp Ser Trp Lys Ile>
___b___b___b___b___b___b_____LEUKOTOXIN_b___b___b___b___b___b___b___>
```

FIG. 5D

```
         1640        1650        1660        1670        1680
          *           *           *           *           *
      *       *   *       *   *       *   *       *   *       *
     ACA GAT GGT GCA GCA AGT TCT ACC TTT GAT TTA ACT AAC GTT GTT CAG CGT
     TGT CTA CCA CGT CGT TCA AGA TGG AAA CTA AAT TGA TTG CAA CAA GTC GCA
     Thr Asp Gly Ala Ala Ser Ser Thr Phe Asp Leu Thr Asn Val Val Gln Arg>
     __b___b___b___b___b___b____LEUKOTOXIN_b___b___b___b___b___b___b___>

1690        1700        1710        1720        1730
          *           *           *           *           *
      *       *   *       *   *       *   *       *   *       *
     ATT GGT ATT GAA TTA GAC AAT GCT GGA AAT GTA ACT AAA ACC AAA GAA ACA
     TAA CCA TAA CTT AAT CTG TTA CGA CCT TTA CAT TGA TTT TGG TTT CTT TGT
     Ile Gly Ile Glu Leu Asp Asn Ala Gly Asn Val Thr Lys Thr Lys Glu Thr>
     __b___b___b___b___b___b____LEUKOTOXIN_b___b___b___b___b___b___b___>

1740        1750        1760        1770        1780
          *           *           *           *           *
      *       *   *       *   *       *   *       *   *       *
     AAA ATT ATT GCC AAA CTT GGT GAA GGT GAT GAC AAC GTA TTT GTT GGT TCT
     TTT TAA TAA CGG TTT GAA CCA CTT CCA CTA CTG TTG CAT AAA CAA CCA AGA
     Lys Ile Ile Ala Lys Leu Gly Glu Gly Asp Asp Asn Val Phe Val Gly Ser>
     __b___b___b___b___b___b____LEUKOTOXIN_b___b___b___b___b___b___b___>

1790        1800        1810        1820        1830
          *           *           *           *           *
      *       *   *       *   *       *   *       *   *       *
     GGT ACG ACG GAA ATT GAT GGC GGT GAA GGT TAC GAC CGA GTT CAC TAT AGC
     CCA TGC TGC CTT TAA CTA CCG CCA CTT CCA ATG CTG GCT CAA GTG ATA TCG
     Gly Thr Thr Glu Ile Asp Gly Gly Glu Gly Tyr Asp Arg Val His Tyr Ser>
     __b___b___b___b___b___b____LEUKOTOXIN_b___b___b___b___b___b___b___>

1840        1850        1860        1870        1880
          *           *           *           *           *
      *       *   *       *   *       *   *       *   *       *
     CGT GGA AAC TAT GGT GCT TTA ACT ATT GAT GCA ACC AAA GAG ACC GAG CAA
     GCA CCT TTG ATA CCA CGA AAT TGA TAA CTA CGT TGG TTT CTC TGG CTC GTT
     Arg Gly Asn Tyr Gly Ala Leu Thr Ile Asp Ala Thr Lys Glu Thr Glu Gln>
     __b___b___b___b___b___b____LEUKOTOXIN_b___b___b___b___b___b___b___>

1890        1900        1910        1920        1930
       *           *           *           *           *
   *       *   *       *   *       *   *       *   *       *
     GGT AGT TAT ACC GTA AAT CGT TTC GTA GAA ACC GGT AAA GCA CTA CAC GAA
     CCA TCA ATA TGG CAT TTA GCA AAG CAT CTT TGG CCA TTT CGT GAT GTG CTT
     Gly Ser Tyr Thr Val Asn Arg Phe Val Glu Thr Gly Lys Ala Leu His Glu>
     __b___b___b___b___b___b____LEUKOTOXIN_b___b___b___b___b___b___b___>

1940        1950        1960        1970        1980
       *           *           *           *           *
   *       *   *       *   *       *   *       *   *       *
     GTG ACT TCA ACC CAT ACC GCA TTA GTG GGC AAC CGT GAA GAA AAA ATA GAA
     CAC TGA AGT TGG GTA TGG CGT AAT CAC CCG TTG GCA CTT CTT TTT TAT CTT
     Val Thr Ser Thr His Thr Ala Leu Val Gly Asn Arg Glu Glu Lys Ile Glu>
     __b___b___b___b___b___b____LEUKOTOXIN_b___b___b___b___b___b___b___>

1990        2000        2010        2020        2030        2040
       *           *           *           *           *           *
   *       *   *       *   *       *   *       *   *       *   *       *
     TAT CGT CAT AGC AAT AAC CAG CAC CAT GCC GGT TAT TAC ACC AAA GAT ACC
     ATA GCA GTA TCG TTA TTG GTC GTG GTA CGG CCA ATA ATG TGG TTT CTA TGG
     Tyr Arg His Ser Asn Asn Gln His His Ala Gly Tyr Tyr Thr Lys Asp Thr>
     __b___b___b___b___b___b____LEUKOTOXIN_b___b___b___b___b___b___b___>
```

*FIG. 5E*

```
         2050         2060         2070         2080         2090
    *      *      *      *      *      *      *      *      *      *
  TTG AAA GCT GTT GAA GAA ATT ATC GGT ACA TCA CAT AAC GAT ATC TTT AAA
  AAC TTT CGA CAA CTT CTT TAA TAG CCA TGT AGT GTA TTG CTA TAG AAA TTT
  Leu Lys Ala Val Glu Glu Ile Ile Gly Thr Ser His Asn Asp Ile Phe Lys>
  ___b___b___b___b___b___b_____LEUKOTOXIN_b___b___b___b___b___b___b___>

2100         2110         2120         2130         2140
    *      *      *      *      *      *      *      *      *      *
  GGT AGT AAG TTC AAT GAT GCC TTT AAC GGT GGT GAT GGT GTC GAT ACT ATT
  CCA TCA TTC AAG TTA CTA CGG AAA TTG CCA CCA CTA CCA CAG CTA TGA TAA
  Gly Ser Lys Phe Asn Asp Ala Phe Asn Gly Gly Asp Gly Val Asp Thr Ile>
  ___b___b___b___b___b___b_____LEUKOTOXIN_b___b___b___b___b___b___b___>

2150         2160         2170         2180         2190
    *      *      *      *      *      *      *      *      *      *
  GAC GGT AAC GAC GGC AAT GAC CGC TTA TTT GGT GGT AAA GGC GAT GAT ATT
  CTG CCA TTG CTG CCG TTA CTG GCG AAT AAA CCA CCA TTT CCG CTA CTA TAA
  Asp Gly Asn Asp Gly Asn Asp Arg Leu Phe Gly Gly Lys Gly Asp Asp Ile>
  ___b___b___b___b___b___b_____LEUKOTOXIN_b___b___b___b___b___b___b___>

2200         2210         2220         2230         2240
    *      *      *      *      *      *      *      *      *      *
  CTC GAT GGT GGA AAT GGT GAT GAT TTT ATC GAT GGC GGT AAA GGC AAC GAC
  GAG CTA CCA CCT TTA CCA CTA CTA AAA TAG CTA CCG CCA TTT CCG TTG CTG
  Leu Asp Gly Gly Asn Gly Asp Asp Phe Ile Asp Gly Gly Lys Gly Asn Asp>
  ___b___b___b___b___b___b_____LEUKOTOXIN_b___b___b___b___b___b___b___>

2250         2260         2270         2280         2290
    *      *      *      *      *      *      *      *      *      *
  CTA TTA CAC GGT GGC AAG GGC GAT GAT ATT TTC GTT CAC CGT AAA GGC GAT
  GAT AAT GTG CCA CCG TTC CCG CTA CTA TAA AAG CAA GTG GCA TTT CCG CTA
  Leu Leu His Gly Gly Lys Gly Asp Asp Ile Phe Val His Arg Lys Gly Asp>
  ___b___b___b___b___b___b_____LEUKOTOXIN_b___b___b___b___b___b___b___>

2300         2310         2320         2330         2340
    *      *      *      *      *      *      *      *      *      *
  GGT AAT GAT ATT ATT ACC GAT TCT GAC GGC AAT GAT AAA TTA TCA TTC TCT
  CCA TTA CTA TAA TAA TGG CTA AGA CTG CCG TTA CTA TTT AAT AGT AAG AGA
  Gly Asn Asp Ile Ile Thr Asp Ser Asp Gly Asn Asp Lys Leu Ser Phe Ser>
  ___b___b___b___b___b___b_____LEUKOTOXIN_b___b___b___b___b___b___b___>

2350         2360         2370         2380         2390
    *      *      *      *      *      *      *      *      *      *
  GAT TCG AAC TTA AAA GAT TTA ACA TTT GAA AAA GTT AAA CAT AAT CTT GTC
  CTA AGC TTG AAT TTT CTA AAT TGT AAA CTT TTT CAA TTT GTA TTA GAA CAG
  Asp Ser Asn Leu Lys Asp Leu Thr Phe Glu Lys Val Lys His Asn Leu Val>
  ___b___b___b___b___b___b_____LEUKOTOXIN_b___b___b___b___b___b___b___>

2400         2410         2420         2430         2440
    *      *      *      *      *      *      *      *      *      *
  ATC ACG AAT AGC AAA AAA GAG AAA GTG ACC ATT CAA AAC TGG TTC CGA GAG
  TAG TGC TTA TCG TTT TTT CTC TTT CAC TGG TAA GTT TTG ACC AAG GCT CTC
  Ile Thr Asn Ser Lys Lys Glu Lys Val Thr Ile Gln Asn Trp Phe Arg Glu>
  ___b___b___b___b___b___b_____LEUKOTOXIN_b___b___b___b___b___b___b___>
```

*FIG. 5F*

```
      2450            2460            2470            2480            2490
   *       *       *       *       *       *       *       *       *       *
GCT GAT TTT GCT AAA GAA GTG CCT AAT TAT AAA GCA ACT AAA GAT GAG AAA
CGA CTA AAA CGA TTT CTT CAC GGA TTA ATA TTT CGT TGA TTT CTA CTC TTT
Ala Asp Phe Ala Lys Glu Val Pro Asn Tyr Lys Ala Thr Lys Asp Glu Lys>
 ___b___b___b___b___b___b____LEUKOTOXIN_b___b___b___b___b___b___b___>

2500            2510            2520            2530            2540            2550
 *       *       *       *       *       *       *       *       *       *       *
ATC GAA GAA ATC ATC GGT CAA AAT GGC GAG CGG ATC ACC TCA AAG CAA GTT
TAG CTT CTT TAG TAG CCA GTT TTA CCG CTC GCC TAG TGG AGT TTC GTT CAA
Ile Glu Glu Ile Ile Gly Gln Asn Gly Glu Arg Ile Thr Ser Lys Gln Val>
 ___b___b___b___b___b___b____LEUKOTOXIN_b___b___b___b___b___b___b___>

2560            2570            2580            2590            2600
         *       *       *       *       *       *       *       *       *
GAT GAT CTT ATC GCA AAA GGT AAC GGC AAA ATT ACC CAA GAT GAG CTA TCA
CTA CTA GAA TAG CGT TTT CCA TTG CCG TTT TAA TGG GTT CTA CTC GAT AGT
Asp Asp Leu Ile Ala Lys Gly Asn Gly Lys Ile Thr Gln Asp Glu Leu Ser>
 ___b___b___b___b___b___b____LEUKOTOXIN_b___b___b___b___b___b___b___>

2610            2620            2630            2640            2650
   *       *       *       *       *       *       *       *       *       *
AAA GTT GTT GAT AAC TAT GAA TTG CTC AAA CAT AGC AAA AAT GTG ACA AAC
TTT CAA CAA CTA TTG ATA CTT AAC GAG TTT GTA TCG TTT TTA CAC TGT TTG
Lys Val Val Asp Asn Tyr Glu Leu Leu Lys His Ser Lys Asn Val Thr Asn>
 ___b___b___b___b___b___b____LEUKOTOXIN_b___b___b___b___b___b___b___>

2660            2670            2680            2690            2700
   *       *       *       *       *       *       *       *       *       *
AGC TTA GAT AAG TTA ATC TCA TCT GTA AGT GCA TTT ACC TCG TCT AAT GAT
TCG AAT CTA TTC AAT TAG AGT AGA CAT TCA CGT AAA TGG AGC AGA TTA CTA
Ser Leu Asp Lys Leu Ile Ser Ser Val Ser Ala Phe Thr Ser Ser Asn Asp>
 ___b___b___b___b___b___b____LEUKOTOXIN_b    b___b___b___b___b___b___>

2710            2720            2730            2740            2750
   *       *       *       *       *       *       *       *       *       *
TCG AGA AAT GTA TTA GTG GCT CCA ACT TCA ATG TTG GAT CAA AGT TTA TCT
AGC TCT TTA CAT AAT CAC CGA GGT TGA AGT TAC AAC CTA GTT TCA AAT AGA
Ser Arg Asn Val Leu Val Ala Pro Thr Ser Met Leu Asp Gln Ser Leu Ser>
 ___b___b___b___b___b___b____LEUKOTOXIN_b___b___b___b___b___b___b___>

2760            2770            2780            2790            2800
   *       *       *       *       *       *       *       *       *       *
TCT CTT CAA TTT GCT AGG G TA GCT GCT TGT AGT TCA CAC ACT CCG GCT CCG
AGA GAA GTT AAA CGA TCC C AT CGA CGA ACA TCA AGT GTG TGA GGC CGA GGC
                        Xxx Ala Ala Cys Ser Ser His Thr Pro Ala Pro>
                        ___a___a____LPPB PEPTIDE [SPLIT]____a___a___>
Ser Leu Gln Phe Ala Arg>
 ___b____LEUKOTOXIN__b___b_>

2810            2820            2830            2840            2850
   *       *       *       *       *       *       *       *       *       *
GTA GAA AAT GCT AAG GAT TTA GCA CCA AGT ATT ATC AAA CCG ATT AAT GGT
CAT CTT TTA CGA TTC CTA AAT CGT GGT TCA TAA TAG TTT GGC TAA TTA CCA
Val Glu Asn Ala Lys Asp Leu Ala Pro Ser Ile Ile Lys Pro Ile Asn Gly>
 ___a___a___a___a___a___LPPB PEPTIDE [SPLIT]____a___a___a___a___a___>
```

FIG. 5G

```
            2860         2870         2880         2890         2900
              *            *            *            *            *
         ACA AAC TCA ACC GCT TGG GAA CCT CAA GTT ATT CAA CAA AAG ATG CCC GAA
         TGT TTG AGT TGG CGA ACC CTT GGA GTT CAA TAA GTT GTT TTC TAC GGG CTT
         Thr Asn Ser Thr Ala Trp Glu Pro Gln Val Ile Gln Gln Lys Met Pro Glu>
         ___a___a___a___a___a___LPPB PEPTIDE [SPLIT]____a___a___a___a___a___>

2910         2920         2930         2940         2950
              *            *            *            *            *
         AGT ATG AGA GTG CCG AAA GCA ACA AAC TCC ACT TAT CAA CCT GAA ATC ATT
         TCA TAC TCT CAC GGC TTT CGT TGT TTG AGG TGA ATA GTT GGA CTT TAG TAA
         Ser Met Arg Val Pro Lys Ala Thr Asn Ser Thr Tyr Gln Pro Glu Ile Ile>
         ___a___a___a___a___a___LPPB PEPTIDE [SPLIT]____a___a___a___a___a___>

2960         2970         2980         2990         3000
              *            *            *            *            *
         CAA CAA AAT CAA CAA AAA ACA GAA TCG ATA GCA AAA AAA CAG GCT CTA CAA
         GTT GTT TTA GTT GTT TTT TGT CTT AGC TAT CGT TTT TTT GTC CGA GAT GTT
         Gln Gln Asn Gln Gln Lys Thr Glu Ser Ile Ala Lys Lys Gln Ala Leu Gln>
         ___a___a___a___a___a___LPPB PEPTIDE [SPLIT]____a___a___a___a___a___>

3010         3020         3030         3040         3050         3060
              *            *            *            *            *            *
         AAT TTT GAA ATT CCA AGA GAT CCT AAA ACT AAT GTG CCT GTT TAT AGC AAA
         TTA AAA CTT TAA GGT TCT CTA GGA TTT TGA TTA CAC GGA CAA ATA TCG TTT
         Asn Phe Glu Ile Pro Arg Asp Pro Lys Thr Asn Val Pro Val Tyr Ser Lys>
         ___a___a___a___a___a___LPPB PEPTIDE [SPLIT]____a___a___a___a___a___>

3070         3080         3090         3100         3110
                *            *            *            *            *
         ATT GAT AAG GGT TTT TAC AAA GGT GAT ACT TAC AAA GTA CGC AAA GGC GAT
         TAA CTA TTC CCA AAA ATG TTT CCA CTA TGA ATG TTT CAT GCG TTT CCG CTA
         Ile Asp Lys Gly Phe Tyr Lys Gly Asp Thr Tyr Lys Val Arg Lys Gly Asp>
         ___a___a___a___a___a___LPPB PEPTIDE [SPLIT]____a___a___a___a___a___>

3120         3130         3140         3150         3160
              *            *            *            *            *
         ACC ATG TTT CTT ATT GCT TAT ATT TCA GGC ATG GAT ATA AAA GAA TTG GCC
         TGG TAC AAA GAA TAA CGA ATA TAA AGT CCG TAC CTA TAT TTT CTT AAC CGG
         Thr Met Phe Leu Ile Ala Tyr Ile Ser Gly Met Asp Ile Lys Glu Leu Ala>
         ___a___a___a___a___a___LPPB PEPTIDE [SPLIT]____a___a___a___a___a___>

3170         3180         3190         3200         3210
              *            *            *            *            *
         ACA CTA AAT AAT ATG TCT GAG CCA TAT CAT CTG AGT ATT GGA CAA GTA TTG
         TGT GAT TTA TTA TAC AGA CTC GGT ATA GTA GAC TCA TAA CCT GTT CAT AAC
         Thr Leu Asn Asn Met Ser Glu Pro Tyr His Leu Ser Ile Gly Gln Val Leu>
         ___a___a___a___a___a___LPPB PEPTIDE [SPLIT]____a___a___a___a___a___>

3220         3230         3240         3250         3260
              *            *            *            *            *
         AAA ATT GCA AAT AAT ATT CCC GAT AGC AAT ATG ATA CCA ACA CAG ACA ATA
         TTT TAA CGT TTA TTA TAA GGG CTA TCG TTA TAC TAT GGT TGT GTC TGT TAT
         Lys Ile Ala Asn Asn Ile Pro Asp Ser Asn Met Ile Pro Thr Gln Thr Ile>
         ___a___a___a___a___a___LPPB PEPTIDE [SPLIT]____a___a___a___a___a___>
```

FIG. 5H

```
         3270          3280          3290          3300          3310
  *      *      *      *      *      *      *      *      *      *      *
AAT GAA TCA GAG GTG ACA CAA AAT ACA GTC AAT GAG ACA TGG AAT GCT AAT
TTA CTT AGT CTC CAC TGT GTT TTA TGT CAG TTA CTC TGT ACC TTA CGA TTA
Asn Glu Ser Glu Val Thr Gln Asn Thr Val Asn Glu Thr Trp Asn Ala Asn>
___a___a___a___a___a___LPPB PEPTIDE [SPLIT]____a___a___a___a___a___>

3320          3330          3340          3350          3360
  *      *      *      *      *      *      *      *      *      *      *
AAA CCA ACA AAT GAA CAA ATG AAA CCC GTT GCT ACA CCA ACA CAT TCA ACA
TTT GGT TGT TTA CTT GTT TAC TTT GGG CAA CGA TGT GGT TGT GTA AGT TGT
Lys Pro Thr Asn Glu Gln Met Lys Pro Val Ala Thr Pro Thr His Ser Thr>
___a___a___a___a___a___LPPB PEPTIDE [SPLIT]____a___a___a___a___a___>

3370          3380          3390          3400          3410
  *      *      *      *      *      *      *      *      *      *      *
ATG CCA ATC AAT AAA ACA CCT CCA GCC ACC TCA AAT ATA GCT TGG ATT TGG
TAC GGT TAG TTA TTT TGT GGA GGT CGG TGG AGT TTA TAT CGA ACC TAA ACC
Met Pro Ile Asn Lys Thr Pro Pro Ala Thr Ser Asn Ile Ala Trp Ile Trp>
___a___a___a___a___a___LPPB PEPTIDE [SPLIT]____a___a___a___a___a___>

3420          3430          3440          3450          3460
  *      *      *      *      *      *      *      *      *      *
CCA ACA AAT GGA AAA ATT ATT CAA GGA TTT TCC AGT GCT GAT GGA GGC AAT
GGT TGT TTA CCT TTT TAA TAA GTT CCT AAA AGG TCA CGA CTA CCT CCG TTA
Pro Thr Asn Gly Lys Ile Ile Gln Gly Phe Ser Ser Ala Asp Gly Gly Asn>
___a___a___a___a___a___LPPB PEPTIDE [SPLIT]____a___a___a___a___a___>

3470          3480          3490          3500          3510
  *      *      *      *      *      *      *      *      *      *
AAA GGT ATT GAT ATT AGC GGT TCT CGT GGA CAA GCT GTT AAT GCA GCA GCT
TTT CCA TAA CTA TAA TCG CCA AGA GCA CCT GTT CGA CAA TTA CGT CGT CGA
Lys Gly Ile Asp Ile Ser Gly Ser Arg Gly Gln Ala Val Asn Ala Ala Ala>
___a___a___a___a___a___LPPB PEPTIDE [SPLIT]____a___a___a___a___a___>

3520          3530          3540          3550          3560          3570
  *      *      *      *      *      *      *      *      *      *      *      *
GCA TGG ACG CAG TTG TAT ATG CCG GAG ACG CTT TAC GTG GAT ATG GTA ATT
CGT ACC TGC GTC AAC ATA TAC GGC CTC TGC GAA ATG CAC CTA TAC CAT TAA
Ala Trp Thr Gln Leu Tyr Met Pro Glu Thr Leu Tyr Val Asp Met Val Ile>
___a___a___a___a___a___LPPB PEPTIDE [SPLIT]____a___a___a___a___a___>

3580          3590          3600          3610          3620
  *      *      *      *      *      *      *      *      *      *
TAATTATTATTAAACATAATGACAGTTATTTAAGTGCTTATGCACATAATG
ATTAATAATAATTTGTATTACTGTCAATAAATTCACGAATACGTGTATTAC 3630         3640
  *      *      *      *      *
AAAGTATCTAGCTAGCTAGCCATGG
TTTCATAGATCGATCGATCGGTACC
```

*FIG. 5I*

SEQUENCE LISTING (1) GENERAL INFORMATION:

(iii) NUMBER OF SEQUENCES: 10

(2) INFORMATION FOR SEQ ID NO:1:

(i) SEQUENCE CHARACTERISTICS:
      (A) LENGTH: 1985 base pairs
      (B) TYPE: nucleic acid
      (C) STRANDEDNESS: single
      (D) TOPOLOGY: linear (ii) MOLECULE TYPE: DNA (genomic)

(ix) FEATURE:
      (A) NAME/KEY: CDS
      (B) LOCATION: 791..1531

(xi) SEQUENCE DESCRIPTION: SEQ ID NO:1:

```
AAAAAATCCA TTGATAGCAA TCAGTTTTAT CTGAAATTGG TACAAAAAAT AATTACTATT      60

TTTAGTATGA ATACCAGTGC AGAATACTTT ACGACTAGAA CTTCGTTTAC GTCTGCCGGT     120

GATGCAGGGT TATTGGGGTG TTCCTTAAAT GCCTTTGAAA ATTACCAACT GAATGAAGCG     180

TGGACTTGGG AAAAACAGGC TTTAGTTCGT TGTAGGGCGG TATACGGCGA TATTGATTTA     240

TGTGAACGCT TTGAAAAAAT TCGTTGTAAT GTGCTTTCAG CTCCAAGAAA TGTGGAACAG     300

CTGAAGCAAG ATATACGAGA GATGCGTCAA AAAATGTATC ATCATCTCTC TAAACATAAA     360

ACGGACGAAT TTAATATTAA GACTGATTTG GGCGGTATCA CAGATATTGA GTTTATTGCA     420

CAATACTTAG TTTTAGCTTA TGCTCCCCAA CACTAGCATT AACACGTTGG TCTGATAATG     480

TAGGATATTT GACTGTATGG CTGAAAGTGC GGTGATTTCA CAAGAAGTTT CCACAAAGTC     540

AAAAAAATGC TATGTAAATT TACGAAACCA AATTCATCAT TTAAATTTAT TAGGTCAAGA     600

ACCGATTATT AATGCACAAC TATTTAGCAA GGAAAGAACG TTTATTCTCA ATACATGGAA     660

AAGTTTATTG GAATGAATGA ACTTATAATT GCCCTAAAAT CAGCATATGA TAAGAAATTA     720

TTTATCATTT GTATTTTCTT TGTTATGCTA TGCAGACCTT TAACTTACAT TAACAAATGA     780

GAAATAAACG ATG AAA TTA AAT AAA TCA CTT TTG GTC GGC ACA TTA GTC         829
            Met Lys Leu Asn Lys Ser Leu Leu Val Gly Thr Leu Val
             1               5                  10

GCC TCA ACT GTA TTA TTA GCA GCT TGT AAT GAA AAA AAT AAA GCG GAA         877
```

```
              Ala Ser Thr Val Leu Leu Ala Ala Cys Asn Glu Lys Asn Lys Ala Glu
                  15                  20                  25

ACA ACG CCA ACT GAA CCG GTT ACA GTT GCA GAA ACT CAA GCT CAA CCT            925
Thr Thr Pro Thr Glu Pro Val Thr Val Ala Glu Thr Gln Ala Gln Pro
 30              35                  40                  45

GAC GTT CAA GGA AAA ACT GAA ACA ACT TCA TCT GAA TCA ACC GCA ATT            973
Asp Val Gln Gly Lys Thr Glu Thr Thr Ser Ser Glu Ser Thr Ala Ile
                 50                  55                  60

GAA AAT ACA CAA TCT GAT GCT CAA GAA AAA ACT GAG ACA ACT TCA GTT           1021
Glu Asn Thr Gln Ser Asp Ala Gln Glu Lys Thr Glu Thr Thr Ser Val
                 65                  70                  75

GAA ACA ACC TCG ACT GAA CCA ACC GCA GCT GGA AAC ACA CAA CCT GAA           1069
Glu Thr Thr Ser Thr Glu Pro Thr Ala Ala Gly Asn Thr Gln Pro Glu
 80                  85                  90

TCT CAA GAA AAA GTT GTT TCA GAA AAA AGT GAG ACA GTT GTT CAA GAA           1117
Ser Gln Glu Lys Val Val Ser Glu Lys Ser Glu Thr Val Val Gln Glu
 95                 100                 105

ATT CTT AAT CAG TTT AAC AAT ACA GTT ACG ATC CAA TTG GTG GGG TAT           1165
Ile Leu Asn Gln Phe Asn Asn Thr Val Thr Ile Gln Leu Val Gly Tyr
110                 115                 120                 125

CAG AGT GAA AAA ATA GAG GGT GAA GAT ACT TTA TCT TTC GTT TAT AAC           1213
Gln Ser Glu Lys Ile Glu Gly Glu Asp Thr Leu Ser Phe Val Tyr Asn
                130                 135                 140

GTT AAG AAT AAA GGT GAT AAA GCA ATC AAA GAA CTT CAG TGG TAT AAC           1261
Val Lys Asn Lys Gly Asp Lys Ala Ile Lys Glu Leu Gln Trp Tyr Asn
                145                 150                 155

CTT GTT TTC TTT AAT TCG ACT CTG GTA GAG CCT CTT TCA ATA GCC TAT           1309
Leu Val Phe Phe Asn Ser Thr Leu Val Glu Pro Leu Ser Ile Ala Tyr
160                 165                 170

TCT TTT GAG GAT ACG CTT GCT CCG GAA GGC GAG GGC GAA ATA AAA TTA           1357
Ser Phe Glu Asp Thr Leu Ala Pro Glu Gly Glu Gly Glu Ile Lys Leu
175                 180                 185

ACA AAA TTA GCT AAA ACT TAT GCT GAA GAG ATT CGT GCA GAT ATA CTA           1405
Thr Lys Leu Ala Lys Thr Tyr Ala Glu Glu Ile Arg Ala Asp Ile Leu
190                 195                 200                 205

AAA CCG GAA GCT AAT CTT CAA TTT AGC CCA ATA ATT GCA GGT CGA ATT           1453
Lys Pro Glu Ala Asn Leu Gln Phe Ser Pro Ile Ile Ala Gly Arg Ile
                210                 215                 220

ATT TTT GAA GAC GGT ACG CAA TTA GTT GTA ACT ACA GAT GAA GAG CTT           1501
Ile Phe Glu Asp Gly Thr Gln Leu Val Val Thr Thr Asp Glu Glu Leu
                225                 230                 235

ACT CAA TCT TTA CAG CAA ATT TTA ACG CAA TAATTTTAA AAATAATTAT              1551
Thr Gln Ser Leu Gln Gln Ile Leu Thr Gln
240                 245

TCAACGCATT AGTTATCTAT CCGCTCTTAC AAATCTATAA TATTTATAAA TAACTACAAA         1611

AAGTTATCAA TAAGATTTTA TAGATTGGTA AGATCGGTTA TGTTTCCGCA TCGAAATCTA         1671

CTGCCCATTA TTGGCGAAAC CGAAAGAAAT TCGTCGTAAA AAGCGTGCAG AGCAACAAGA         1731

AAAAGAAGTG TGAAGAAAAA AAGCTGAGAA TTTGCTAAAA ATCAGCTCAA CAAACCGCAC         1791

TTTAATAATA AAAATTTCTG CGAGAAATCA TGTAAAAAAA ATAACACCCT CTTAACAAGA         1851

AGAGGGTGAA TAATCAATTT ACCATTGGTA CCCTATAGAA ACTGAACCTG CCATTTTGCC         1911

TTGAGAATTT CTATTTCCTT GAAATTTAAG CATAATCTTA CGTTATCACT CATACGAGAA         1971

TAACCAATCG CCAT                                                          1985

(2) INFORMATION FOR SEQ ID NO:2:

(i) SEQUENCE CHARACTERISTICS:
```

(A) LENGTH: 247 amino acids
        (B) TYPE: amino acid
        (D) TOPOLOGY: linear (ii) MOLECULE TYPE: protein (xi) SEQUENCE DESCRIPTION: SEQ ID NO:2:

Met Lys Leu Asn Lys Ser Leu Leu Val Gly Thr Leu Val Ala Ser Thr
 1               5                  10                  15

Val Leu Leu Ala Ala Cys Asn Glu Lys Asn Lys Ala Glu Thr Thr Pro
            20                  25                  30

Thr Glu Pro Val Thr Val Ala Glu Thr Gln Ala Gln Pro Asp Val Gln
        35                  40                  45

Gly Lys Thr Glu Thr Thr Ser Ser Glu Ser Thr Ala Ile Glu Asn Thr
    50                  55                  60

Gln Ser Asp Ala Gln Glu Lys Thr Glu Thr Thr Ser Val Glu Thr Thr
65                  70                  75                  80

Ser Thr Glu Pro Thr Ala Ala Gly Asn Thr Gln Pro Glu Ser Gln Glu
                85                  90                  95

Lys Val Val Ser Glu Lys Ser Glu Thr Val Val Gln Glu Ile Leu Asn
            100                 105                 110

Gln Phe Asn Asn Thr Val Thr Ile Gln Leu Val Gly Tyr Gln Ser Glu
        115                 120                 125

Lys Ile Glu Gly Glu Asp Thr Leu Ser Phe Val Tyr Asn Val Lys Asn
    130                 135                 140

Lys Gly Asp Lys Ala Ile Lys Glu Leu Gln Trp Tyr Asn Leu Val Phe
145                 150                 155                 160

Phe Asn Ser Thr Leu Val Glu Pro Leu Ser Ile Ala Tyr Ser Phe Glu
                165                 170                 175

Asp Thr Leu Ala Pro Glu Gly Glu Gly Glu Ile Lys Leu Thr Lys Leu
            180                 185                 190

Ala Lys Thr Tyr Ala Glu Glu Ile Arg Ala Asp Ile Leu Lys Pro Glu
        195                 200                 205

Ala Asn Leu Gln Phe Ser Pro Ile Ile Ala Gly Arg Ile Ile Phe Glu
    210                 215                 220

Asp Gly Thr Gln Leu Val Val Thr Thr Asp Glu Glu Leu Thr Gln Ser
225                 230                 235                 240

Leu Gln Gln Ile Leu Thr Gln
                245

(2) INFORMATION FOR SEQ ID NO:3:

(i) SEQUENCE CHARACTERISTICS:
        (A) LENGTH: 1885 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 872..1708

(xi) SEQUENCE DESCRIPTION: SEQ ID NO:3:

CGACGCCAGT GCCAAGCTTG CATGCCTGCA GGTGATCTAA GCTTCCCGGG ATCCAAGAGG      60

TGAAGAGATT TATTGGATTG GACCAATAGG ACTGGCAGAA AATGAATCGG AAGGAACGGA     120

CTTCCATGCC GTTAAAAACG GCTATGTGTC AATTACACCC ATTCAAACAG ATATGACGGC     180

```
ATATCATTCA ATGACAGCTT TACAACAATG GTTAGATAAG GAATAACGAT AATCTTTTCA     240

TCGAAGGAAT AAAACATGAA AATTTTCGGT ACGCTATATG ATAAAACTAT GCAATGGGCA     300

AATCACCGTT TGCTACATT TTGGCTAACT TTTGTTAGTT TTATTGAGGC TATTTTCTTC      360

CCAATACCAC CTGATGTCAT GCTTATTCCG ATGTCAATAA ATAAACCTAA ATGTGCTACT     420

AAATTTGCAT TTTATGCAGC AATGGCTTCA GCCATTGGTG GGGCAATTGG TTATGGATTA     480

GGTTATTACG CTTTTGATTT CATACAAAGT TATATTCAAC AATGGGGTTA TCAACAACAT     540

TGGGAAACTG CTCTTTCTTG GTTCAAAGAA TGGGGTATTT GGGTAGTTTT CGTTGCAGGT     600

TTTTCACCTA TTCCTTATAA AATTTTTACG ATTTGTGCAG GCGTCATGCA AATGGCATTT     660

TTGCCTTTCT TACTTACTGC CTTTATTTCT CGTATTGCAA GATTTTTGCT CGTTACCCAT     720

TTAGCGGCTT GGAGCGGAAA AAAATTTGCT GCGAAATTAC GTCAATCTAT TGAATTTATC     780

GGTTGGTCAG TTGTCATTAT TGCTATAGTT GTATATCTTG TCTTGAAATA ATCTAAGATA     840

AAAAATGAAT ATAAAGTAAC GGAGAATTTA C ATG AAA AAA TTT TTA CCT TTA        892
                                  Met Lys Lys Phe Leu Pro Leu
                                   1               5

TCT ATT AGT ATC ACT GTA CTA GCT GCT TGT AGT TCA CAC ACT CCG GCT       940
Ser Ile Ser Ile Thr Val Leu Ala Ala Cys Ser Ser His Thr Pro Ala
        10              15              20

CCG GTA GAA AAT GCT AAG GAT TTA GCA CCA AGT ATT ATC AAA CCG ATT       988
Pro Val Glu Asn Ala Lys Asp Leu Ala Pro Ser Ile Ile Lys Pro Ile
25              30              35

AAT GGT ACA AAC TCA ACC GCT TGG GAA CCT CAA GTT ATT CAA CAA AAG      1036
Asn Gly Thr Asn Ser Thr Ala Trp Glu Pro Gln Val Ile Gln Gln Lys
40              45              50              55

ATG CCC GAA AGT ATG AGA GTG CCG AAA GCA ACA AAC TCC ACT TAT CAA      1084
Met Pro Glu Ser Met Arg Val Pro Lys Ala Thr Asn Ser Thr Tyr Gln
            60              65              70

CCT GAA ATC ATT CAA CAA AAT CAA CAA AAA ACA GAA TCG ATA GCA AAA      1132
Pro Glu Ile Ile Gln Gln Asn Gln Gln Lys Thr Glu Ser Ile Ala Lys
        75              80              85

AAA CAG GCT CTA CAA AAT TTT GAA ATT CCA AGA GAT CCT AAA ACT AAT      1180
Lys Gln Ala Leu Gln Asn Phe Glu Ile Pro Arg Asp Pro Lys Thr Asn
    90              95              100

GTG CCT GTT TAT AGC AAA ATT GAT AAG GGT TTT TAC AAA GGT GAT ACT      1228
Val Pro Val Tyr Ser Lys Ile Asp Lys Gly Phe Tyr Lys Gly Asp Thr
    105             110             115

TAC AAA GTA CGC AAA GGC GAT ACC ATG TTT CTT ATT GCT TAT ATT TCA      1276
Tyr Lys Val Arg Lys Gly Asp Thr Met Phe Leu Ile Ala Tyr Ile Ser
120             125             130             135

GGC ATG GAT ATA AAA GAA TTG GCC ACA CTA AAT AAT ATG TCT GAG CCA      1324
Gly Met Asp Ile Lys Glu Leu Ala Thr Leu Asn Asn Met Ser Glu Pro
            140             145             150

TAT CAT CTG AGT ATT GGA CAA GTA TTG AAA ATT GCA AAT AAT ATT CCC      1372
Tyr His Leu Ser Ile Gly Gln Val Leu Lys Ile Ala Asn Asn Ile Pro
        155             160             165

GAT AGC AAT ATG ATA CCA ACA CAG ACA ATA AAT GAA TCA GAG GTG ACA      1420
Asp Ser Asn Met Ile Pro Thr Gln Thr Ile Asn Glu Ser Glu Val Thr
    170             175             180

CAA AAT ACA GTC AAT GAG ACA TGG AAT GCT AAT AAA CCA ACA AAT GAA      1468
Gln Asn Thr Val Asn Glu Thr Trp Asn Ala Asn Lys Pro Thr Asn Glu
    185             190             195

CAA ATG AAA CCC GTT GCT ACA CCA ACA CAT TCA ACA ATG CCA ATC AAT      1516
Gln Met Lys Pro Val Ala Thr Pro Thr His Ser Thr Met Pro Ile Asn
200             205             210             215

AAA ACA CCT CCA GCC ACC TCA AAT ATA GCT TGG ATT TGG CCA ACA AAT      1564
```

```
                Lys Thr Pro Pro Ala Thr Ser Asn Ile Ala Trp Ile Trp Pro Thr Asn
                            220                 225                 230

GGA AAA ATT ATT CAA GGA TTT TCC AGT GCT GAT GGA GGC AAT AAA GGT                1612
Gly Lys Ile Ile Gln Gly Phe Ser Ser Ala Asp Gly Gly Asn Lys Gly
            235                 240                 245

ATT GAT ATT AGC GGT TCT CGT GGA CAA GCT GTT AAT GCA GCA GCT GCA                1660
Ile Asp Ile Ser Gly Ser Arg Gly Gln Ala Val Asn Ala Ala Ala Ala
            250                 255                 260

TGG ACG CAG TTG TAT ATG CCG GAG ACG CTT TAC GTG GAT ATG GTA ATT                1708
Trp Thr Gln Leu Tyr Met Pro Glu Thr Leu Tyr Val Asp Met Val Ile
        265                 270                 275

TAATTATTAT TAAACATAAT GACAGTTATT TAAGTGCTTA TGCACATAAT GAAAGTATAC              1768

TCGTCAAAGA TCAGCAAGAA GTTAAAGCGG GTCAACAAAT TGCTAAAATG GGAAGTTCTG              1828

GAACAAACAC AATCAAACTC CATTTTAAAT TCGTTATTTT GGTCAATCAG TAGATCC                 1885

(2) INFORMATION FOR SEQ ID NO:4:

(i) SEQUENCE CHARACTERISTICS:
        (A) LENGTH: 279 amino acids
        (B) TYPE: amino acid
        (D) TOPOLOGY: linear (ii) MOLECULE TYPE: protein (xi) SEQUENCE DESCRIPTION: SEQ ID NO:4:

Met Lys Lys Phe Leu Pro Leu Ser Ile Ser Ile Thr Val Leu Ala Ala
  1               5                  10                  15

Cys Ser Ser His Thr Pro Ala Pro Val Glu Asn Ala Lys Asp Leu Ala
                 20                  25                  30

Pro Ser Ile Ile Lys Pro Ile Asn Gly Thr Asn Ser Thr Ala Trp Glu
             35                  40                  45

Pro Gln Val Ile Gln Gln Lys Met Pro Glu Ser Met Arg Val Pro Lys
         50                  55                  60

Ala Thr Asn Ser Thr Tyr Gln Pro Glu Ile Ile Gln Gln Asn Gln Gln
 65                  70                  75                  80

Lys Thr Glu Ser Ile Ala Lys Lys Gln Ala Leu Gln Asn Phe Glu Ile
                 85                  90                  95

Pro Arg Asp Pro Lys Thr Asn Val Pro Val Tyr Ser Lys Ile Asp Lys
            100                 105                 110

Gly Phe Tyr Lys Gly Asp Thr Tyr Lys Val Arg Lys Gly Asp Thr Met
        115                 120                 125

Phe Leu Ile Ala Tyr Ile Ser Gly Met Asp Ile Lys Glu Leu Ala Thr
130                 135                 140

Leu Asn Asn Met Ser Glu Pro Tyr His Leu Ser Ile Gly Gln Val Leu
145                 150                 155                 160

Lys Ile Ala Asn Asn Ile Pro Asp Ser Asn Met Ile Pro Thr Gln Thr
                165                 170                 175

Ile Asn Glu Ser Glu Val Thr Gln Asn Thr Val Asn Glu Thr Trp Asn
            180                 185                 190

Ala Asn Lys Pro Thr Asn Glu Gln Met Lys Pro Val Ala Thr Pro Thr
        195                 200                 205

His Ser Thr Met Pro Ile Asn Lys Thr Pro Pro Ala Thr Ser Asn Ile
    210                 215                 220

Ala Trp Ile Trp Pro Thr Asn Gly Lys Ile Ile Gln Gly Phe Ser Ser
225                 230                 235                 240

Ala Asp Gly Gly Asn Lys Gly Ile Asp Ile Ser Gly Ser Arg Gly Gln
```

```
                    245                 250                 255
Ala Val Asn Ala Ala Ala Trp Thr Gln Leu Tyr Met Pro Glu Thr
                260                 265                 270

Leu Tyr Val Asp Met Val Ile
            275

(2) INFORMATION FOR SEQ ID NO:5:

(i) SEQUENCE CHARACTERISTICS:
        (A) LENGTH: 2465 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 108..1850

(xi) SEQUENCE DESCRIPTION: SEQ ID NO:5:

TTTAATACGA CTCACTATAG GGAATTCGAG TCGATCTAAG CTTCCCGGGG ATCACCGTGC        60

ATTTTACATT GCACATACTC AAGGAGCAAT TTATGTTATC TATTTTA ATG CAA GGT        116
                                                  Met Gln Gly
                                                    1

TTA CGC TTA AAA AAA TGC TTT CTC CCG ATT TTA GTT ATG TTT TTT TTA        164
Leu Arg Leu Lys Lys Cys Phe Leu Pro Ile Leu Val Met Phe Phe Leu
    5                  10                  15

GCA GGC TGT GTC AAT TTA TTA GGC AGT AGC TTT ACG GCA AGC TTA AAA        212
Ala Gly Cys Val Asn Leu Leu Gly Ser Ser Phe Thr Ala Ser Leu Lys
 20                  25                  30                  35

AAT GAT GCC AAT GCA AGT TCT GAT TTT TAC ATT CGG AAA ATT GAA CAA        260
Asn Asp Ala Asn Ala Ser Ser Asp Phe Tyr Ile Arg Lys Ile Glu Gln
                 40                  45                  50

ACA CAA AAT CAA CAA GAT TTA CAA ACC TAT AAA CTT TTA GCT GCT CGA        308
Thr Gln Asn Gln Gln Asp Leu Gln Thr Tyr Lys Leu Leu Ala Ala Arg
         55                  60                  65

GTT TTA GTA ACA GAA AAT AAA ATC CCG CAA GCG GAA GCA TAT CTT GCT        356
Val Leu Val Thr Glu Asn Lys Ile Pro Gln Ala Glu Ala Tyr Leu Ala
     70                  75                  80

GAA TTG ATA GAT TTA AAT GAT GAA CAA AAA CTA GAT AAA TCC CTG ATT        404
Glu Leu Ile Asp Leu Asn Asp Glu Gln Lys Leu Asp Lys Ser Leu Ile
 85                  90                  95

GAA GCT CAT ATT TCT GCT GTT AAA GGC AAA AAT GAA ACG GCA GAA TAT        452
Glu Ala His Ile Ser Ala Val Lys Gly Lys Asn Glu Thr Ala Glu Tyr
100                 105                 110                 115

CAA TTA TCT TTA ATT CAC TTG ACA TTA CTT AGT CCT TCA CAA AAA TCA        500
Gln Leu Ser Leu Ile His Leu Thr Leu Leu Ser Pro Ser Gln Lys Ser
                120                 125                 130

CGT TAT TAT GAG ATT GTT TCT CGT ATT GCA GAA AAT CGT CAT GAT AAT        548
Arg Tyr Tyr Glu Ile Val Ser Arg Ile Ala Glu Asn Arg His Asp Asn
        135                 140                 145

ATT TCA GCG ATA AAA GCT CGA ATT CAA ATG GAT AAT TTT TTA AGT GAT        596
Ile Ser Ala Ile Lys Ala Arg Ile Gln Met Asp Asn Phe Leu Ser Asp
            150                 155                 160

ATT CAA CGA AAA CAA CAA AAT AAT GAC CGC ACT TGG GCA TTG CTA CGC        644
Ile Gln Arg Lys Gln Gln Asn Asn Asp Arg Thr Trp Ala Leu Leu Arg
        165                 170                 175

AAT ACA GAT AGT GAA GTA CTA AAT AAT ACT GAT GCG GAA GGA AAT ATT        692
Asn Thr Asp Ser Glu Val Leu Asn Asn Thr Asp Ala Glu Gly Asn Ile
180                 185                 190                 195
```

```
ACA TTG AGC GGT TGG TTA ACA TTA GCT CAA CTA TAC AAT GAT AAC CTT        740
Thr Leu Ser Gly Trp Leu Thr Leu Ala Gln Leu Tyr Asn Asp Asn Leu
            200                 205                 210

AAT CAA CCT GCA CAA TTA ATT CAA ACA TTA CTG ACT TGG AAA AAT TAT        788
Asn Gln Pro Ala Gln Leu Ile Gln Thr Leu Leu Thr Trp Lys Asn Tyr
            215                 220                 225

TAT CCA ACA CAT ACG GCA GCA CAT TTA TTA CCT ACA GAA TTA CAA GGG        836
Tyr Pro Thr His Thr Ala Ala His Leu Leu Pro Thr Glu Leu Gln Gly
            230                 235                 240

CTT GCC AAT TTT CAA CAA ACT ACT TTA ACG CAA GTC GGT CTA ATA CTC        884
Leu Ala Asn Phe Gln Gln Thr Thr Leu Thr Gln Val Gly Leu Ile Leu
            245                 250                 255

CCT TTA AGC GGC AAT ACA CGA CTT ATC GGT GAA ACA ATC AAA AAC GGG        932
Pro Leu Ser Gly Asn Thr Arg Leu Ile Gly Glu Thr Ile Lys Asn Gly
260                 265                 270                 275

TTT GAT GAT GCC AAA GTC AAT TAC AAT GTT CAA GTT CAC GTA TTT GAC        980
Phe Asp Asp Ala Lys Val Asn Tyr Asn Val Gln Val His Val Phe Asp
                280                 285                 290

TCA ATG AAA ATG TCT ATA GAA CAA ATT ATT AAT CAA GCA AAA AAA CAG       1028
Ser Met Lys Met Ser Ile Glu Gln Ile Ile Asn Gln Ala Lys Lys Gln
            295                 300                 305

GGA ATT AAC ACT CTT GTC GGA CCA TTA CTC AAA CAA AAT GTT GAT GTT       1076
Gly Ile Asn Thr Leu Val Gly Pro Leu Leu Lys Gln Asn Val Asp Val
            310                 315                 320

ATA GTC AAT AAT CCG TAT TTG GTA CAA GAT TTA AAT GTA TTA GCG TTG       1124
Ile Val Asn Asn Pro Tyr Leu Val Gln Asp Leu Asn Val Leu Ala Leu
            325                 330                 335

AAC TCT ACG CCT AAT GCA CGG GCA ATT GAA CAC CTT TGT TAT TAT GGA       1172
Asn Ser Thr Pro Asn Ala Arg Ala Ile Glu His Leu Cys Tyr Tyr Gly
340                 345                 350                 355

TTA TCG CCT GAA GAT GAA GCT GAA AGT GCG GCA AGT AAA ATG TGG AAT       1220
Leu Ser Pro Glu Asp Glu Ala Glu Ser Ala Ala Ser Lys Met Trp Asn
                360                 365                 370

GAT GCA GTA CGT ATT CCA CTT GTT TTA GTA CCG CAA AAT AAT CTG GGG       1268
Asp Ala Val Arg Ile Pro Leu Val Leu Val Pro Gln Asn Asn Leu Gly
            375                 380                 385

CGA CGC ACG GCA GCG GCA TTT ACT CTA CGT TGG CAA CAA CTA TTG GGT       1316
Arg Arg Thr Ala Ala Ala Phe Thr Leu Arg Trp Gln Gln Leu Leu Gly
            390                 395                 400

ACT GAT GCC AAT ATT AAA TTC TAT AAT CAA ACC GCA GAT ATT AAT TTT       1364
Thr Asp Ala Asn Ile Lys Phe Tyr Asn Gln Thr Ala Asp Ile Asn Phe
405                 410                 415

GCA TTA AAA TCG GGG TTA AGT GAA AGT ACT GAC GGC GTG TAT ATT ATT       1412
Ala Leu Lys Ser Gly Leu Ser Glu Ser Thr Asp Gly Val Tyr Ile Ile
420                 425                 430                 435

GCT AAT AAC AAA CAA TTA GCT GAA ATT AAA GCA GTG TTG GAT AAT ATT       1460
Ala Asn Asn Lys Gln Leu Ala Glu Ile Lys Ala Val Leu Asp Asn Ile
                440                 445                 450

AAT CCG ACC CTA AAA CTT TAT GCA AGT TCA CGT AGT AAT TCG CCT AAC       1508
Asn Pro Thr Leu Lys Leu Tyr Ala Ser Ser Arg Ser Asn Ser Pro Asn
            455                 460                 465

AGT GGT CCT GAA CAT CGT TTG TTT CTG AAT AAT CTG CAA TTT AGT GAT       1556
Ser Gly Pro Glu His Arg Leu Phe Leu Asn Asn Leu Gln Phe Ser Asp
            470                 475                 480

ATT CCG TTC TTC AAA GAT AGG GAA TCG GAA CAA TAT AAA AAA ATT GAA       1604
Ile Pro Phe Phe Lys Asp Arg Glu Ser Glu Gln Tyr Lys Lys Ile Glu
            485                 490                 495

AAA ATG ACC AAT AAT GAT TAC TCA TTA ATG CAT TTA TAT GCT ATG GGT       1652
Lys Met Thr Asn Asn Asp Tyr Ser Leu Met His Leu Tyr Ala Met Gly
500                 505                 510                 515
```

```
TAT GAT GCT TGG TTA TTA ATA AAT CAA TTT AAT GAA TTC CGT CAA ATT       1700
Tyr Asp Ala Trp Leu Leu Ile Asn Gln Phe Asn Glu Phe Arg Gln Ile
                520                 525                 530

CCC GGA TTT ACC ATT GAT GGG TTA ACA GGA AAA CTC AGT GCC GGC CCT       1748
Pro Gly Phe Thr Ile Asp Gly Leu Thr Gly Lys Leu Ser Ala Gly Pro
                535                 540                 545

AAC TGT AAT GTT GAA CGT GAT ATG ACT TGG TTC CAA TAT CAA AAT GGC       1796
Asn Cys Asn Val Glu Arg Asp Met Thr Trp Phe Gln Tyr Gln Asn Gly
                550                 555                 560

AGT ATC TAT CCG CTT AAC GAG CAA GAT GAC AGC ATC TAT CTG ATT AAC       1844
Ser Ile Tyr Pro Leu Asn Glu Gln Asp Asp Ser Ile Tyr Leu Ile Asn
                565                 570                 575

GAA GAA TGATACAATC CAAACGTCAA CAAGGTGCGA GTTTTGAATA TCAGGCTCGC        1900
Glu Glu
580

CTCTTTTTAG AGAGACAAGG TTTAACCTTT ATTGCAGCTA ACCAACGCTT TAACTGCGGT     1960

GAATTGGATT TGATTATGCA AGATCGGCAA ACGATCGTTT TTGTTGAGGT TCGTCAGCGT     2020

AAAAATCAAA TTTTCGGTTC AGCAATTGAC AGTGTAGATT GGAAAAAGCA GCAAAAATGG     2080

CTTGATGCAG CCAACCTATG GTTAGCACAA TATGATTCCA GTTTAGAAGA TGCGGACTGC     2140

CGTTTCGATC TGGTCGCTTT TGGAGCAACA ACAAATGATA TCCAATGGAT ACCTAATTTT     2200

CTTGATGAAT AAAAATTATG AAAAAGTTAA AGATATTTAT ACGGAAAGTA TTCAAACTCA     2260

AATTTCTTCC TCCAGCTTAC TTGCAACAAA ATCGTAGAG GCAACTCAAC ATATTGTAAA      2320

TTGCCTGCTG AAAGGTAATA AAATTATTGT CTGTGGGCAT GGTAGATCCT AGCTAGCTAG     2380

CCATGGACCT GCAGGCATGC AAGCTTGGCA CTGAGTCGTT CGTTTTTACA ACGTTCGTTG     2440

ACTGGGAAAA CCCTGGTCCG TTTAG                                          2465

(2) INFORMATION FOR SEQ ID NO:6:

(i) SEQUENCE CHARACTERISTICS:
        (A) LENGTH: 581 amino acids
        (B) TYPE: amino acid
        (D) TOPOLOGY: linear (ii) MOLECULE TYPE: protein (xi) SEQUENCE DESCRIPTION: SEQ ID NO:6:

Met Gln Gly Leu Arg Leu Lys Lys Cys Phe Leu Pro Ile Leu Val Met
 1                   5                  10                  15

Phe Phe Leu Ala Gly Cys Val Asn Leu Leu Gly Ser Ser Phe Thr Ala
                20                  25                  30

Ser Leu Lys Asn Asp Ala Asn Ala Ser Ser Asp Phe Tyr Ile Arg Lys
            35                  40                  45

Ile Glu Gln Thr Gln Asn Gln Gln Asp Leu Gln Thr Tyr Lys Leu Leu
        50                  55                  60

Ala Ala Arg Val Leu Val Thr Glu Asn Lys Ile Pro Gln Ala Glu Ala
65                  70                  75                  80

Tyr Leu Ala Glu Leu Ile Asp Leu Asn Asp Glu Gln Lys Leu Asp Lys
                85                  90                  95

Ser Leu Ile Glu Ala His Ile Ser Ala Val Lys Gly Lys Asn Glu Thr
            100                 105                 110

Ala Glu Tyr Gln Leu Ser Leu Ile His Leu Thr Leu Leu Ser Pro Ser
        115                 120                 125

Gln Lys Ser Arg Tyr Tyr Glu Ile Val Ser Arg Ile Ala Glu Asn Arg
    130                 135                 140
```

-continued

```
His Asp Asn Ile Ser Ala Ile Lys Ala Arg Ile Gln Met Asp Asn Phe
145                 150                 155                 160

Leu Ser Asp Ile Gln Arg Lys Gln Gln Asn Asn Asp Arg Thr Trp Ala
                165                 170                 175

Leu Leu Arg Asn Thr Asp Ser Glu Val Leu Asn Asn Thr Asp Ala Glu
                180                 185                 190

Gly Asn Ile Thr Leu Ser Gly Trp Leu Thr Leu Ala Gln Leu Tyr Asn
                195                 200                 205

Asp Asn Leu Asn Gln Pro Ala Gln Leu Ile Gln Thr Leu Leu Thr Trp
210                 215                 220

Lys Asn Tyr Tyr Pro Thr His Thr Ala Ala His Leu Leu Pro Thr Glu
225                 230                 235                 240

Leu Gln Gly Leu Ala Asn Phe Gln Gln Thr Thr Leu Thr Gln Val Gly
                245                 250                 255

Leu Ile Leu Pro Leu Ser Gly Asn Thr Arg Leu Ile Gly Glu Thr Ile
                260                 265                 270

Lys Asn Gly Phe Asp Asp Ala Lys Val Asn Tyr Asn Val Gln Val His
                275                 280                 285

Val Phe Asp Ser Met Lys Met Ser Ile Glu Gln Ile Asn Gln Ala
290                 295                 300

Lys Lys Gln Gly Ile Asn Thr Leu Val Gly Pro Leu Leu Lys Gln Asn
305                 310                 315                 320

Val Asp Val Ile Val Asn Asn Pro Tyr Leu Val Gln Asp Leu Asn Val
                325                 330                 335

Leu Ala Leu Asn Ser Thr Pro Asn Ala Arg Ala Ile Glu His Leu Cys
                340                 345                 350

Tyr Tyr Gly Leu Ser Pro Glu Asp Glu Ala Glu Ser Ala Ala Ser Lys
                355                 360                 365

Met Trp Asn Asp Ala Val Arg Ile Pro Leu Val Leu Val Pro Gln Asn
370                 375                 380

Asn Leu Gly Arg Arg Thr Ala Ala Ala Phe Thr Leu Arg Trp Gln Gln
385                 390                 395                 400

Leu Leu Gly Thr Asp Ala Asn Ile Lys Phe Tyr Asn Gln Thr Ala Asp
                405                 410                 415

Ile Asn Phe Ala Leu Lys Ser Gly Leu Ser Glu Ser Thr Asp Gly Val
                420                 425                 430

Tyr Ile Ile Ala Asn Asn Lys Gln Leu Ala Glu Ile Lys Ala Val Leu
                435                 440                 445

Asp Asn Ile Asn Pro Thr Leu Lys Leu Tyr Ala Ser Ser Arg Ser Asn
450                 455                 460

Ser Pro Asn Ser Gly Pro Glu His Arg Leu Phe Leu Asn Asn Leu Gln
465                 470                 475                 480

Phe Ser Asp Ile Pro Phe Lys Asp Arg Glu Ser Glu Gln Tyr Lys
                485                 490                 495

Lys Ile Glu Lys Met Thr Asn Asp Tyr Ser Leu Met His Leu Tyr
                500                 505                 510

Ala Met Gly Tyr Asp Ala Trp Leu Leu Ile Asn Gln Phe Asn Glu Phe
                515                 520                 525

Arg Gln Ile Pro Gly Phe Thr Ile Asp Gly Leu Thr Gly Lys Leu Ser
530                 535                 540

Ala Gly Pro Asn Cys Asn Val Glu Arg Asp Met Thr Trp Phe Gln Tyr
545                 550                 555                 560
```

```
Gln Asn Gly Ser Ile Tyr Pro Leu Asn Glu Gln Asp Asp Ser Ile Tyr
            565                 570                 575

Leu Ile Asn Glu Glu
        580

(2) INFORMATION FOR SEQ ID NO:7:

(i) SEQUENCE CHARACTERISTICS:
        (A) LENGTH: 3646 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 1..2772

(ix) FEATURE:
        (A) NAME/KEY: CDS
        (B) LOCATION: 2776..3570

(xi) SEQUENCE DESCRIPTION: SEQ ID NO:7:

ATG GCT ACT GTT ATA GAT CTA AGC TTC CCA AAA ACT GGG GCA AAA AAA        48
Met Ala Thr Val Ile Asp Leu Ser Phe Pro Lys Thr Gly Ala Lys Lys
 1               5                  10                  15

ATT ATC CTC TAT ATT CCC CAA AAT TAC CAA TAT GAT ACT GAA CAA GGT        96
Ile Ile Leu Tyr Ile Pro Gln Asn Tyr Gln Tyr Asp Thr Glu Gln Gly
                 20                  25                  30

AAT GGT TTA CAG GAT TTA GTC AAA GCG GCC GAA GAG TTG GGG ATT GAG       144
Asn Gly Leu Gln Asp Leu Val Lys Ala Ala Glu Glu Leu Gly Ile Glu
             35                  40                  45

GTA CAA AGA GAA GAA CGC AAT AAT ATT GCA ACA GCT CAA ACC AGT TTA       192
Val Gln Arg Glu Glu Arg Asn Asn Ile Ala Thr Ala Gln Thr Ser Leu
         50                  55                  60

GGC ACG ATT CAA ACC GCT ATT GGC TTA ACT GAG CGT GGC ATT GTG TTA       240
Gly Thr Ile Gln Thr Ala Ile Gly Leu Thr Glu Arg Gly Ile Val Leu
 65                  70                  75                  80

TCC GCT CCA CAA ATT GAT AAA TTG CTA CAG AAA ACT AAA GCA GGC CAA       288
Ser Ala Pro Gln Ile Asp Lys Leu Leu Gln Lys Thr Lys Ala Gly Gln
                 85                  90                  95

GCA TTA GGT TCT GCC GAA AGC ATT GTA CAA AAT GCA AAT AAA GCC AAA       336
Ala Leu Gly Ser Ala Glu Ser Ile Val Gln Asn Ala Asn Lys Ala Lys
                100                 105                 110

ACT GTA TTA TCT GGC ATT CAA TCT ATT TTA GGC TCA GTA TTG GCT GGA       384
Thr Val Leu Ser Gly Ile Gln Ser Ile Leu Gly Ser Val Leu Ala Gly
            115                 120                 125

ATG GAT TTA GAT GAG GCC TTA CAG AAT AAC AGC AAC CAA CAT GCT CTT       432
Met Asp Leu Asp Glu Ala Leu Gln Asn Asn Ser Asn Gln His Ala Leu
130                 135                 140

GCT AAA GCT GGC TTG GAG CTA ACA AAT TCA TTA ATT GAA AAT ATT GCT       480
Ala Lys Ala Gly Leu Glu Leu Thr Asn Ser Leu Ile Glu Asn Ile Ala
145                 150                 155                 160

AAT TCA GTA AAA ACA CTT GAC GAA TTT GGT GAG CAA ATT AGT CAA TTT       528
Asn Ser Val Lys Thr Leu Asp Glu Phe Gly Glu Gln Ile Ser Gln Phe
                165                 170                 175

GGT TCA AAA CTA CAA AAT ATC AAA GGC TTA GGG ACT TTA GGA GAC AAA       576
Gly Ser Lys Leu Gln Asn Ile Lys Gly Leu Gly Thr Leu Gly Asp Lys
                180                 185                 190

CTC AAA AAT ATC GGT GGA CTT GAT AAA GCT GGC CTT GGT TTA GAT GTT       624
Leu Lys Asn Ile Gly Gly Leu Asp Lys Ala Gly Leu Gly Leu Asp Val
            195                 200                 205
```

```
ATC TCA GGG CTA TTA TCG GGC GCA ACA GCT GCA CTT GTA CTT GCA GAT      672
Ile Ser Gly Leu Leu Ser Gly Ala Thr Ala Ala Leu Val Leu Ala Asp
210                 215                 220

AAA AAT GCT TCA ACA GCT AAA AAA GTG GGT GCG GGT TTT GAA TTG GCA      720
Lys Asn Ala Ser Thr Ala Lys Lys Val Gly Ala Gly Phe Glu Leu Ala
225                 230                 235                 240

AAC CAA GTT GTT GGT AAT ATT ACC AAA GCC GTT TCT TCT TAC ATT TTA      768
Asn Gln Val Val Gly Asn Ile Thr Lys Ala Val Ser Ser Tyr Ile Leu
            245                 250                 255

GCC CAA CGT GTT GCA GCA GGT TTA TCT TCA ACT GGG CCT GTG GCT GCT      816
Ala Gln Arg Val Ala Ala Gly Leu Ser Ser Thr Gly Pro Val Ala Ala
        260                 265                 270

TTA ATT GCT TCT ACT GTT TCT CTT GCG ATT AGC CCA TTA GCA TTT GCC      864
Leu Ile Ala Ser Thr Val Ser Leu Ala Ile Ser Pro Leu Ala Phe Ala
    275                 280                 285

GGT ATT GCC GAT AAA TTT AAT CAT GCA AAA AGT TTA GAG AGT TAT GCC      912
Gly Ile Ala Asp Lys Phe Asn His Ala Lys Ser Leu Glu Ser Tyr Ala
290                 295                 300

GAA CGC TTT AAA AAA TTA GGC TAT GAC GGA GAT AAT TTA TTA GCA GAA      960
Glu Arg Phe Lys Lys Leu Gly Tyr Asp Gly Asp Asn Leu Leu Ala Glu
305                 310                 315                 320

TAT CAG CGG GGA ACA GGG ACT ATT GAT GCA TCG GTT ACT GCA ATT AAT     1008
Tyr Gln Arg Gly Thr Gly Thr Ile Asp Ala Ser Val Thr Ala Ile Asn
            325                 330                 335

ACC GCA TTG GCC GCT ATT GCT GGT GGT GTG TCT GCT GCT GCA GCC GGC     1056
Thr Ala Leu Ala Ala Ile Ala Gly Gly Val Ser Ala Ala Ala Ala Gly
        340                 345                 350

TCG GTT ATT GCT TCA CCG ATT GCC TTA TTA GTA TCT GGG ATT ACC GGT     1104
Ser Val Ile Ala Ser Pro Ile Ala Leu Leu Val Ser Gly Ile Thr Gly
    355                 360                 365

GTA ATT TCT ACG ATT CTG CAA TAT TCT AAA CAA GCA ATG TTT GAG CAC     1152
Val Ile Ser Thr Ile Leu Gln Tyr Ser Lys Gln Ala Met Phe Glu His
370                 375                 380

GTT GCA AAT AAA ATT CAT AAC AAA ATT GTA GAA TGG GAA AAA AAT AAT     1200
Val Ala Asn Lys Ile His Asn Lys Ile Val Glu Trp Glu Lys Asn Asn
385                 390                 395                 400

CAC GGT AAG AAC TAC TTT GAA AAT GGT TAC GAT GCC CGT TAT CTT GCG     1248
His Gly Lys Asn Tyr Phe Glu Asn Gly Tyr Asp Ala Arg Tyr Leu Ala
            405                 410                 415

AAT TTA CAA GAT AAT ATG AAA TTC TTA CTG AAC TTA AAC AAA GAG TTA     1296
Asn Leu Gln Asp Asn Met Lys Phe Leu Leu Asn Leu Asn Lys Glu Leu
        420                 425                 430

CAG GCA GAA CGT GTC ATC GCT ATT ACT CAG CAG CAA TGG GAT AAC AAC     1344
Gln Ala Glu Arg Val Ile Ala Ile Thr Gln Gln Gln Trp Asp Asn Asn
    435                 440                 445

ATT GGT GAT TTA GCT GGT ATT AGC CGT TTA GGT GAA AAA GTC CTT AGT     1392
Ile Gly Asp Leu Ala Gly Ile Ser Arg Leu Gly Glu Lys Val Leu Ser
450                 455                 460

GGT AAA GCC TAT GTG GAT GCG TTT GAA GAA GGC AAA CAC ATT AAA GCC     1440
Gly Lys Ala Tyr Val Asp Ala Phe Glu Glu Gly Lys His Ile Lys Ala
465                 470                 475                 480

GAT AAA TTA GTA CAG TTG GAT TCG GCA AAC GGT ATT ATT GAT GTG AGT     1488
Asp Lys Leu Val Gln Leu Asp Ser Ala Asn Gly Ile Ile Asp Val Ser
            485                 490                 495

AAT TCG GGT AAA GCG AAA ACT CAG CAT ATC TTA TTC AGA ACG CCA TTA     1536
Asn Ser Gly Lys Ala Lys Thr Gln His Ile Leu Phe Arg Thr Pro Leu
        500                 505                 510

TTG ACG CCG GGA ACA GAG CAT CGT GAA CGC GTA CAA ACA GGT AAA TAT     1584
Leu Thr Pro Gly Thr Glu His Arg Glu Arg Val Gln Thr Gly Lys Tyr
    515                 520                 525
```

```
GAA TAT ATT ACC AAG CTC AAT ATT AAC CGT GTA GAT AGC TGG AAA ATT         1632
Glu Tyr Ile Thr Lys Leu Asn Ile Asn Arg Val Asp Ser Trp Lys Ile
        530                 535                 540

ACA GAT GGT GCA GCA AGT TCT ACC TTT GAT TTA ACT AAC GTT GTT CAG         1680
Thr Asp Gly Ala Ala Ser Ser Thr Phe Asp Leu Thr Asn Val Val Gln
545                 550                 555                 560

CGT ATT GGT ATT GAA TTA GAC AAT GCT GGA AAT GTA ACT AAA ACC AAA         1728
Arg Ile Gly Ile Glu Leu Asp Asn Ala Gly Asn Val Thr Lys Thr Lys
                565                 570                 575

GAA ACA AAA ATT ATT GCC AAA CTT GGT GAA GGT GAT GAC AAC GTA TTT         1776
Glu Thr Lys Ile Ile Ala Lys Leu Gly Glu Gly Asp Asp Asn Val Phe
            580                 585                 590

GTT GGT TCT GGT ACG ACG GAA ATT GAT GGC GGT GAA GGT TAC GAC CGA         1824
Val Gly Ser Gly Thr Thr Glu Ile Asp Gly Gly Glu Gly Tyr Asp Arg
        595                 600                 605

GTT CAC TAT AGC CGT GGA AAC TAT GGT GCT TTA ACT ATT GAT GCA ACC         1872
Val His Tyr Ser Arg Gly Asn Tyr Gly Ala Leu Thr Ile Asp Ala Thr
610                 615                 620

AAA GAG ACC GAG CAA GGT AGT TAT ACC GTA AAT CGT TTC GTA GAA ACC         1920
Lys Glu Thr Glu Gln Gly Ser Tyr Thr Val Asn Arg Phe Val Glu Thr
625                 630                 635                 640

GGT AAA GCA CTA CAC GAA GTG ACT TCA ACC CAT ACC GCA TTA GTG GGC         1968
Gly Lys Ala Leu His Glu Val Thr Ser Thr His Thr Ala Leu Val Gly
                645                 650                 655

AAC CGT GAA GAA AAA ATA GAA TAT CGT CAT AGC AAT AAC CAG CAC CAT         2016
Asn Arg Glu Glu Lys Ile Glu Tyr Arg His Ser Asn Asn Gln His His
            660                 665                 670

GCC GGT TAT TAC ACC AAA GAT ACC TTG AAA GCT GTT GAA GAA ATT ATC         2064
Ala Gly Tyr Tyr Thr Lys Asp Thr Leu Lys Ala Val Glu Glu Ile Ile
        675                 680                 685

GGT ACA TCA CAT AAC GAT ATC TTT AAA GGT AGT AAG TTC AAT GAT GCC         2112
Gly Thr Ser His Asn Asp Ile Phe Lys Gly Ser Lys Phe Asn Asp Ala
690                 695                 700

TTT AAC GGT GGT GAT GGT GTC GAT ACT ATT GAC GGT AAC GAC GGC AAT         2160
Phe Asn Gly Gly Asp Gly Val Asp Thr Ile Asp Gly Asn Asp Gly Asn
705                 710                 715                 720

GAC CGC TTA TTT GGT GGT AAA GGC GAT GAT ATT CTC GAT GGT GGA AAT         2208
Asp Arg Leu Phe Gly Gly Lys Gly Asp Asp Ile Leu Asp Gly Gly Asn
                725                 730                 735

GGT GAT GAT TTT ATC GAT GGC GGT AAA GGC AAC GAC CTA TTA CAC GGT         2256
Gly Asp Asp Phe Ile Asp Gly Gly Lys Gly Asn Asp Leu Leu His Gly
            740                 745                 750

GGC AAG GGC GAT GAT ATT TTC GTT CAC CGT AAA GGC GAT GGT AAT GAT         2304
Gly Lys Gly Asp Asp Ile Phe Val His Arg Lys Gly Asp Gly Asn Asp
        755                 760                 765

ATT ATT ACC GAT TCT GAC GGC AAT GAT AAA TTA TCA TTC TCT GAT TCG         2352
Ile Ile Thr Asp Ser Asp Gly Asn Asp Lys Leu Ser Phe Ser Asp Ser
770                 775                 780

AAC TTA AAA GAT TTA ACA TTT GAA AAA GTT AAA CAT AAT CTT GTC ATC         2400
Asn Leu Lys Asp Leu Thr Phe Glu Lys Val Lys His Asn Leu Val Ile
785                 790                 795                 800

ACG AAT AGC AAA AAA GAG AAA GTG ACC ATT CAA AAC TGG TTC CGA GAG         2448
Thr Asn Ser Lys Lys Glu Lys Val Thr Ile Gln Asn Trp Phe Arg Glu
                805                 810                 815

GCT GAT TTT GCT AAA GAA GTG CCT AAT TAT AAA GCA ACT AAA GAT GAG         2496
Ala Asp Phe Ala Lys Glu Val Pro Asn Tyr Lys Ala Thr Lys Asp Glu
            820                 825                 830

AAA ATC GAA GAA ATC ATC GGT CAA AAT GGC GAG CGG ATC ACC TCA AAG         2544
Lys Ile Glu Glu Ile Ile Gly Gln Asn Gly Glu Arg Ile Thr Ser Lys
```

```
              835                 840                 845
CAA GTT GAT GAT CTT ATC GCA AAA GGT AAC GGC AAA ATT ACC CAA GAT      2592
Gln Val Asp Asp Leu Ile Ala Lys Gly Asn Gly Lys Ile Thr Gln Asp
    850                 855                 860

GAG CTA TCA AAA GTT GTT GAT AAC TAT GAA TTG CTC AAA CAT AGC AAA      2640
Glu Leu Ser Lys Val Val Asp Asn Tyr Glu Leu Leu Lys His Ser Lys
865                 870                 875                 880

AAT GTG ACA AAC AGC TTA GAT AAG TTA ATC TCA TCT GTA AGT GCA TTT      2688
Asn Val Thr Asn Ser Leu Asp Lys Leu Ile Ser Ser Val Ser Ala Phe
                885                 890                 895

ACC TCG TCT AAT GAT TCG AGA AAT GTA TTA GTG GCT CCA ACT TCA ATG      2736
Thr Ser Ser Asn Asp Ser Arg Asn Val Leu Val Ala Pro Thr Ser Met
            900                 905                 910

TTG GAT CAA AGT TTA TCT TCT CTT CAA TTT GCT AGG GTA GCT GCT TGT      2784
Leu Asp Gln Ser Leu Ser Ser Leu Gln Phe Ala Arg     Ala Ala Cys
            915                 920                     1

AGT TCA CAC ACT CCG GCT CCG GTA GAA AAT GCT AAG GAT TTA GCA CCA      2832
Ser Ser His Thr Pro Ala Pro Val Glu Asn Ala Lys Asp Leu Ala Pro
    5                   10                  15

AGT ATT ATC AAA CCG ATT AAT GGT ACA AAC TCA ACC GCT TGG GAA CCT      2880
Ser Ile Ile Lys Pro Ile Asn Gly Thr Asn Ser Thr Ala Trp Glu Pro
20                  25                  30                  35

CAA GTT ATT CAA CAA AAG ATG CCC GAA AGT ATG AGA GTG CCG AAA GCA      2928
Gln Val Ile Gln Gln Lys Met Pro Glu Ser Met Arg Val Pro Lys Ala
            40                  45                  50

ACA AAC TCC ACT TAT CAA CCT GAA ATC ATT CAA CAA AAT CAA CAA AAA      2976
Thr Asn Ser Thr Tyr Gln Pro Glu Ile Ile Gln Gln Asn Gln Gln Lys
        55                  60                  65

ACA GAA TCG ATA GCA AAA AAA CAG GCT CTA CAA AAT TTT GAA ATT CCA      3024
Thr Glu Ser Ile Ala Lys Lys Gln Ala Leu Gln Asn Phe Glu Ile Pro
    70                  75                  80

AGA GAT CCT AAA ACT AAT GTG CCT GTT TAT AGC AAA ATT GAT AAG GGT      3072
Arg Asp Pro Lys Thr Asn Val Pro Val Tyr Ser Lys Ile Asp Lys Gly
85                  90                  95

TTT TAC AAA GGT GAT ACT TAC AAA GTA CGC AAA GGC GAT ACC ATG TTT      3120
Phe Tyr Lys Gly Asp Thr Tyr Lys Val Arg Lys Gly Asp Thr Met Phe
100                 105                 110                 115

CTT ATT GCT TAT ATT TCA GGC ATG GAT ATA AAA GAA TTG GCC ACA CTA      3168
Leu Ile Ala Tyr Ile Ser Gly Met Asp Ile Lys Glu Leu Ala Thr Leu
                120                 125                 130

AAT AAT ATG TCT GAG CCA TAT CAT CTG AGT ATT GGA CAA GTA TTG AAA      3216
Asn Asn Met Ser Glu Pro Tyr His Leu Ser Ile Gly Gln Val Leu Lys
            135                 140                 145

ATT GCA AAT AAT ATT CCC GAT AGC AAT ATG ATA CCA ACA CAG ACA ATA      3264
Ile Ala Asn Asn Ile Pro Asp Ser Asn Met Ile Pro Thr Gln Thr Ile
        150                 155                 160

AAT GAA TCA GAG GTG ACA CAA AAT ACA GTC AAT GAG ACA TGG AAT GCT      3312
Asn Glu Ser Glu Val Thr Gln Asn Thr Val Asn Glu Thr Trp Asn Ala
    165                 170                 175

AAT AAA CCA ACA AAT GAA CAA ATG AAA CCC GTT GCT ACA CCA ACA CAT      3360
Asn Lys Pro Thr Asn Glu Gln Met Lys Pro Val Ala Thr Pro Thr His
180                 185                 190                 195

TCA ACA ATG CCA ATC AAT AAA ACA CCT CCA GCC ACC TCA AAT ATA GCT      3408
Ser Thr Met Pro Ile Asn Lys Thr Pro Pro Ala Thr Ser Asn Ile Ala
                200                 205                 210

TGG ATT TGG CCA ACA AAT GGA AAA ATT ATT CAA GGA TTT TCC AGT GCT      3456
Trp Ile Trp Pro Thr Asn Gly Lys Ile Ile Gln Gly Phe Ser Ser Ala
            215                 220                 225

GAT GGA GGC AAT AAA GGT ATT GAT ATT AGC GGT TCT CGT GGA CAA GCT      3504
```

```
Asp Gly Gly Asn Lys Gly Ile Asp Ile Ser Gly Ser Arg Gly Gln Ala
            230                 235                 240

GTT AAT GCA GCA GCT GCA TGG ACG CAG TTG TAT ATG CCG GAG ACG CTT      3552
Val Asn Ala Ala Ala Ala Trp Thr Gln Leu Tyr Met Pro Glu Thr Leu
        245                 250                 255

TAC GTG GAT ATG GTA ATT TAATTATTAT TAAACATAAT GACAGTTATT             3600
Tyr Val Asp Met Val Ile
260              265

TAAGTGCTTA TGCACATAAT GAAAGTATCT AGCTAGCTAG CCATGG                   3646

(2) INFORMATION FOR SEQ ID NO:8:

(i) SEQUENCE CHARACTERISTICS:
        (A) LENGTH: 924 amino acids
        (B) TYPE: amino acid
        (D) TOPOLOGY: linear (ii) MOLECULE TYPE: protein (xi) SEQUENCE DESCRIPTION: SEQ ID NO:8:

Met Ala Thr Val Ile Asp Leu Ser Phe Pro Lys Thr Gly Ala Lys Lys
 1               5                  10                  15

Ile Ile Leu Tyr Ile Pro Gln Asn Tyr Gln Tyr Asp Thr Glu Gln Gly
            20                  25                  30

Asn Gly Leu Gln Asp Leu Val Lys Ala Ala Glu Glu Leu Gly Ile Glu
        35                  40                  45

Val Gln Arg Glu Arg Asn Asn Ile Ala Thr Ala Gln Thr Ser Leu
    50                  55                  60

Gly Thr Ile Gln Thr Ala Ile Gly Leu Thr Glu Arg Gly Ile Val Leu
65                  70                  75                  80

Ser Ala Pro Gln Ile Asp Lys Leu Leu Gln Lys Thr Lys Ala Gly Gln
                85                  90                  95

Ala Leu Gly Ser Ala Glu Ser Ile Val Gln Asn Ala Asn Lys Ala Lys
            100                 105                 110

Thr Val Leu Ser Gly Ile Gln Ser Ile Leu Gly Ser Val Leu Ala Gly
        115                 120                 125

Met Asp Leu Asp Glu Ala Leu Gln Asn Asn Ser Asn Gln His Ala Leu
    130                 135                 140

Ala Lys Ala Gly Leu Glu Leu Thr Asn Ser Leu Ile Glu Asn Ile Ala
145                 150                 155                 160

Asn Ser Val Lys Thr Leu Asp Glu Phe Gly Gln Ile Ser Gln Phe
                165                 170                 175

Gly Ser Lys Leu Gln Asn Ile Lys Gly Leu Gly Thr Leu Gly Asp Lys
            180                 185                 190

Leu Lys Asn Ile Gly Gly Leu Asp Lys Ala Gly Leu Gly Leu Asp Val
        195                 200                 205

Ile Ser Gly Leu Leu Ser Gly Ala Thr Ala Ala Leu Val Leu Ala Asp
    210                 215                 220

Lys Asn Ala Ser Thr Ala Lys Lys Val Gly Ala Gly Phe Glu Leu Ala
225                 230                 235                 240

Asn Gln Val Val Gly Asn Ile Thr Lys Ala Val Ser Ser Tyr Ile Leu
                245                 250                 255

Ala Gln Arg Val Ala Ala Gly Leu Ser Ser Thr Gly Pro Val Ala Ala
            260                 265                 270

Leu Ile Ala Ser Thr Val Ser Leu Ala Ile Ser Pro Leu Ala Phe Ala
        275                 280                 285
```

-continued

```
Gly Ile Ala Asp Lys Phe Asn His Ala Lys Ser Leu Glu Ser Tyr Ala
290                 295                 300

Glu Arg Phe Lys Lys Leu Gly Tyr Asp Gly Asp Asn Leu Leu Ala Glu
305                 310                 315                 320

Tyr Gln Arg Gly Thr Gly Thr Ile Asp Ala Ser Val Thr Ala Ile Asn
                325                 330                 335

Thr Ala Leu Ala Ala Ile Ala Gly Gly Val Ser Ala Ala Ala Ala Gly
                340                 345                 350

Ser Val Ile Ala Ser Pro Ile Ala Leu Leu Val Ser Gly Ile Thr Gly
                355                 360                 365

Val Ile Ser Thr Ile Leu Gln Tyr Ser Lys Gln Ala Met Phe Glu His
370                 375                 380

Val Ala Asn Lys Ile His Asn Lys Ile Val Glu Trp Glu Lys Asn Asn
385                 390                 395                 400

His Gly Lys Asn Tyr Phe Glu Asn Gly Tyr Asp Ala Arg Tyr Leu Ala
                405                 410                 415

Asn Leu Gln Asp Asn Met Lys Phe Leu Leu Asn Leu Asn Lys Glu Leu
                420                 425                 430

Gln Ala Glu Arg Val Ile Ala Ile Thr Gln Gln Trp Asp Asn Asn
                435                 440                 445

Ile Gly Asp Leu Ala Gly Ile Ser Arg Leu Gly Glu Lys Val Leu Ser
450                 455                 460

Gly Lys Ala Tyr Val Asp Ala Phe Glu Gly Lys His Ile Lys Ala
465                 470                 475                 480

Asp Lys Leu Val Gln Leu Asp Ser Ala Asn Gly Ile Ile Asp Val Ser
                485                 490                 495

Asn Ser Gly Lys Ala Lys Thr Gln His Ile Leu Phe Arg Thr Pro Leu
                500                 505                 510

Leu Thr Pro Gly Thr Glu His Arg Glu Arg Val Gln Thr Gly Lys Tyr
                515                 520                 525

Glu Tyr Ile Thr Lys Leu Asn Ile Asn Arg Val Asp Ser Trp Lys Ile
530                 535                 540

Thr Asp Gly Ala Ala Ser Ser Thr Phe Asp Leu Thr Asn Val Val Gln
545                 550                 555                 560

Arg Ile Gly Ile Glu Leu Asp Asn Ala Gly Asn Val Thr Lys Thr Lys
                565                 570                 575

Glu Thr Lys Ile Ile Ala Lys Leu Gly Glu Gly Asp Asn Val Phe
                580                 585                 590

Val Gly Ser Gly Thr Thr Glu Ile Asp Gly Gly Glu Gly Tyr Asp Arg
                595                 600                 605

Val His Tyr Ser Arg Gly Asn Tyr Gly Ala Leu Thr Ile Asp Ala Thr
610                 615                 620

Lys Glu Thr Glu Gln Gly Ser Tyr Thr Val Asn Arg Phe Val Glu Thr
625                 630                 635                 640

Gly Lys Ala Leu His Glu Val Thr Ser Thr His Thr Ala Leu Val Gly
                645                 650                 655

Asn Arg Glu Glu Lys Ile Glu Tyr Arg His Ser Asn Asn Gln His His
                660                 665                 670

Ala Gly Tyr Tyr Thr Lys Asp Thr Leu Lys Ala Val Glu Glu Ile Ile
                675                 680                 685

Gly Thr Ser His Asn Asp Ile Phe Lys Gly Ser Lys Phe Asn Asp Ala
690                 695                 700

Phe Asn Gly Gly Asp Gly Val Asp Thr Ile Asp Gly Asn Asp Gly Asn
```

-continued

```
              705                 710                 715                 720
Asp Arg Leu Phe Gly Gly Lys Gly Asp Asp Ile Leu Asp Gly Gly Asn
                    725                 730                 735

Gly Asp Asp Phe Ile Asp Gly Gly Lys Gly Asn Asp Leu Leu His Gly
                740                 745                 750

Gly Lys Gly Asp Asp Ile Phe Val His Arg Lys Gly Asp Gly Asn Asp
                755                 760                 765

Ile Ile Thr Asp Ser Asp Gly Asn Asp Lys Leu Ser Phe Ser Asp Ser
                770                 775                 780

Asn Leu Lys Asp Leu Thr Phe Glu Lys Val Lys His Asn Leu Val Ile
785                 790                 795                 800

Thr Asn Ser Lys Lys Glu Lys Val Thr Ile Gln Asn Trp Phe Arg Glu
                805                 810                 815

Ala Asp Phe Ala Lys Glu Val Pro Asn Tyr Lys Ala Thr Lys Asp Glu
                820                 825                 830

Lys Ile Glu Glu Ile Ile Gly Gln Asn Gly Glu Arg Ile Thr Ser Lys
                835                 840                 845

Gln Val Asp Asp Leu Ile Ala Lys Gly Asn Gly Lys Ile Thr Gln Asp
                850                 855                 860

Glu Leu Ser Lys Val Val Asp Asn Tyr Glu Leu Leu Lys His Ser Lys
865                 870                 875                 880

Asn Val Thr Asn Ser Leu Asp Lys Leu Ile Ser Ser Val Ser Ala Phe
                885                 890                 895

Thr Ser Ser Asn Asp Ser Arg Asn Val Leu Val Ala Pro Thr Ser Met
                900                 905                 910

Leu Asp Gln Ser Leu Ser Ser Leu Gln Phe Ala Arg
                915                 920
```

(2) INFORMATION FOR SEQ ID NO:9:

(i) SEQUENCE CHARACTERISTICS:
        (A) LENGTH: 265 amino acids
        (B) TYPE: amino acid
        (D) TOPOLOGY: linear (ii) MOLECULE TYPE: protein (xi) SEQUENCE DESCRIPTION: SEQ ID NO:9:

```
Ala Ala Cys Ser Ser His Thr Pro Ala Pro Val Glu Asn Ala Lys Asp
1               5                   10                  15

Leu Ala Pro Ser Ile Ile Lys Pro Ile Asn Gly Thr Asn Ser Thr Ala
                20                  25                  30

Trp Glu Pro Gln Val Ile Gln Gln Lys Met Pro Glu Ser Met Arg Val
            35                  40                  45

Pro Lys Ala Thr Asn Ser Thr Tyr Gln Pro Glu Ile Ile Gln Gln Asn
        50                  55                  60

Gln Gln Lys Thr Glu Ser Ile Ala Lys Lys Gln Ala Leu Gln Asn Phe
65              70                  75                  80

Glu Ile Pro Arg Asp Pro Lys Thr Asn Val Pro Val Tyr Ser Lys Ile
                85                  90                  95

Asp Lys Gly Phe Tyr Lys Gly Asp Thr Tyr Lys Val Arg Lys Gly Asp
                100                 105                 110

Thr Met Phe Leu Ile Ala Tyr Ile Ser Gly Met Asp Ile Lys Glu Leu
                115                 120                 125

Ala Thr Leu Asn Asn Met Ser Glu Pro Tyr His Leu Ser Ile Gly Gln
                130                 135                 140
```

```
Val Leu Lys Ile Ala Asn Asn Ile Pro Asp Ser Asn Met Ile Pro Thr
145                 150                 155                 160

Gln Thr Ile Asn Glu Ser Glu Val Thr Gln Asn Thr Val Asn Glu Thr
                165                 170                 175

Trp Asn Ala Asn Lys Pro Thr Asn Glu Gln Met Lys Pro Val Ala Thr
            180                 185                 190

Pro Thr His Ser Thr Met Pro Ile Asn Lys Thr Pro Pro Ala Thr Ser
        195                 200                 205

Asn Ile Ala Trp Ile Trp Pro Thr Asn Gly Lys Ile Ile Gln Gly Phe
    210                 215                 220

Ser Ser Ala Asp Gly Gly Asn Lys Gly Ile Asp Ile Ser Gly Ser Arg
225                 230                 235                 240

Gly Gln Ala Val Asn Ala Ala Ala Trp Thr Gln Leu Tyr Met Pro
                245                 250                 255

Glu Thr Leu Tyr Val Asp Met Val Ile
                260                 265

(2) INFORMATION FOR SEQ ID NO:10:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_difference
        (B) LOCATION: replace(17, "")
        (D) OTHER INFORMATION: /note= "This base differs from the
            wild-type sequence."

(xi) SEQUENCE DESCRIPTION: SEQ ID NO:10:

TGTATTATTA GCAGCTGGTA ATGAAAAAAA TAA                                33
```

NUCLEIC ACID MOLECULES ENCODING *HAEMOPHILUS SOMNUS* PROTEINS

This application is a divisional application under 37 C.F.R. 1.60, of pending prior application Ser. No. 08/038,719 filed on Mar. 29, 1993, now abandoned which is a continuation-in-part of application Ser. No. 07/865,050 filed on Apr. 9, 1992, now abandoned, from which applications priority is claimed pursuant to 35 USC §120 and which are hereby incorporated by reference in their entirety.

TECHNICAL FIELD

The present invention relates generally to the prevention of disease in cattle. More particularly, the present invention relates to subunit vaccines for *Haemophilus somnus*.

BACKGROUND

*Haemophilus somnus* is a Gram negative bacterium which causes a number of disease syndromes in animals. The bacterium is commonly associated with thromboembolic meningoencephalitis (ITEME), septicemia, arthritis, and pneumonia (Corbeil, L. B., *Can. J. Vet. Res.* (1990) 54:S57–S62; Harris, F. W., and Janzen, E. D., *Can. Vet. J.* (1990) 30:816–822; Humphrey, J. D., and Stephens, L. R., *Vet. Bull.* (1983) 53:987–1004). These diseases can cause significant economic losses to the farm industry.

Currently available vaccines are either based on killed whole cells or on a protein fraction enriched in outer membrane proteins (OMPs). However, whole cell bacterins and surface protein extracts often contain immunosuppressive components which can render animals more susceptible to infection. Furthermore, the OMP enriched vaccine has only been shown to offer significant protection against *H. somnus* induced disease in an experimental challenge model (Harland, R. J., et al., *Res. Work. Anim. Dis.* 71st (1990) 29:6).

The outer membrane of *H. somnus* includes a 40 kDa protein (as determined by SDS-PAGE) which reacts with convalescent serum (Corbeil, L. B., et al., *infect. Immun.* (1987) 55:1381–1386; Goglolewski, R. P., et al., *Infect. Immun.* (1988) 56:2307–2316). Additionally, antibodies directed against a 40 kDa OMP have been shown to prevent infection in vitro in a neutralization experiment (Gogolewski et al., supra) and a seroreactive protein of 40 kDa is present in all *H. somnus* isolates that have been tested (Corbeil et al., 1987).

A 39 kDa OMP, antigenically distinct from the 40 kDa OMP described above, has also been identified. This protein reacts with convalescent-phase serum and is conserved among all *H. somnus* isolates tested.

An increasing number of bacterial antigens have now been identified as lipoproteins (Anderson, B. E., et al., *J. Bacteriol.* (1988) 170:4493–4500; Bricker, T. M., et al., *Infect. Immun.* (1988) 56:295–301; Hanson, M. S., and Hansen, E. J., *Mol. Microbiol.* (1991) 5:267–278; Hubbard, C. L., et al., *Infect. Immun.* (1991) 59:1521–1528; Nelson, M. B., et al., *Infect. Immun.* (1988) 56:128–134; Thirkell, D., et al., *Infect. Immun.* (1991) 59:781–784). These lipoproteins are generally localized in the envelope of the cell and are therefore exposed to the host's immune system. It has been shown that the murein lipoprotein from the outer membrane of *Escherichia coli* acts as a potent activator of murine lymphocytes, inducing both proliferation and immunoglobulin secretion (Bessler, W., et al. *Z. Immun.* (1977) 153:11–22; Melchers, F., et al. *J. Exp. Med.* (1975 142:473–482). The active lipoprotein portion of the protein has been shown to reside in the N-terminal fatty acid containing region of the protein. Recent studies using synthetic lipopeptides based on this protein show that even short peptides, containing two to five amino acids covalently linked to palmitate, are able to activate murine lymphocytes (Bessler, W. G., et al. *J. Immunol.* (1985) 135:1900–1905).

To date, only one such lipoprotein from *H. somnus* has been positively identified. This protein, termed "LppA", is an OMP with an apparent molecular mass of 40 kDa, as determined by gel electrophoresis. The nucleotide sequence for LppA has been determined (Theisen, M., et al., *Infect. Immun.* (1992) 60:826–831). However, the protective capability of this protein has not previously been studied.

DISCLOSURE OF THE INVENTION

The present invention is based on the characterization of certain *H. somnus* lipoproteins, termed LppA, LppB and LppC herein, and the recombinant production thereof. These proteins, or antigenic fragments thereof, can be used either alone or in combination in novel subunit vaccines to provide protection from *H. somnus* infection in vertebrate subjects.

Accordingly, in one embodiment, the subject invention is directed to a purified, immunogenic *H. somnus* protein selected from the group consisting of LppA, LppB, LppC and immunogenic fragments of LppA, LppB and LppC.

In another embodiment, the instant invention is directed to an isolated nucleotide sequence encoding an immunogenic *H. somnus* protein wherein the protein is selected from the group consisting of LppA, LppB, LppC and immunogenic fragments of LppA, LppB and LppC.

In yet another embodiment, the subject invention is directed to a recombinant vector comprising:
 (a) a nucleotide sequence encoding a polypeptide containing at least one epitope of an *Haemophilus somnus* lipoprotein; and
 (b) control sequences that are operably linked to said nucleotide sequence whereby the nucleotide sequence can be transcribed and translated in a host cell, and at least one of the control sequences is heterologous to the nucleotide sequence.

In still further embodiments, the instant invention is directed to host cells transformed with these vectors and methods of recombinantly producing the *H. somnus* lipoproteins.

In another embodiment, the subject invention is directed to a vaccine composition comprising a pharmaceutically acceptable vehicle and at least one *H. somnus* lipoprotein.

In yet another embodiment, the present invention is directed to a method of treating or preventing *H. somnus* infection in a vertebrate subject comprising administering to the subject a therapeutically effective amount of the above vaccine composition. These and other embodiments of the present invention will readily occur to those of ordinary skill in the art in view of the disclosure herein.

BRIEF DESCRIPTION OF THE FIGURES

FIGS. 1A through 1B (SEQ ID NOS:1–2) depicts the nucleotide sequence and deduced amino acid sequence of the *H. somnus* lppA region. The sequence of the antisense strand is shown with numbering starting from the 5'-end Shine-Dalgarno (SD) sequence. The transcriptional start of the lppA gene is indicated by 1.

Figure 2:
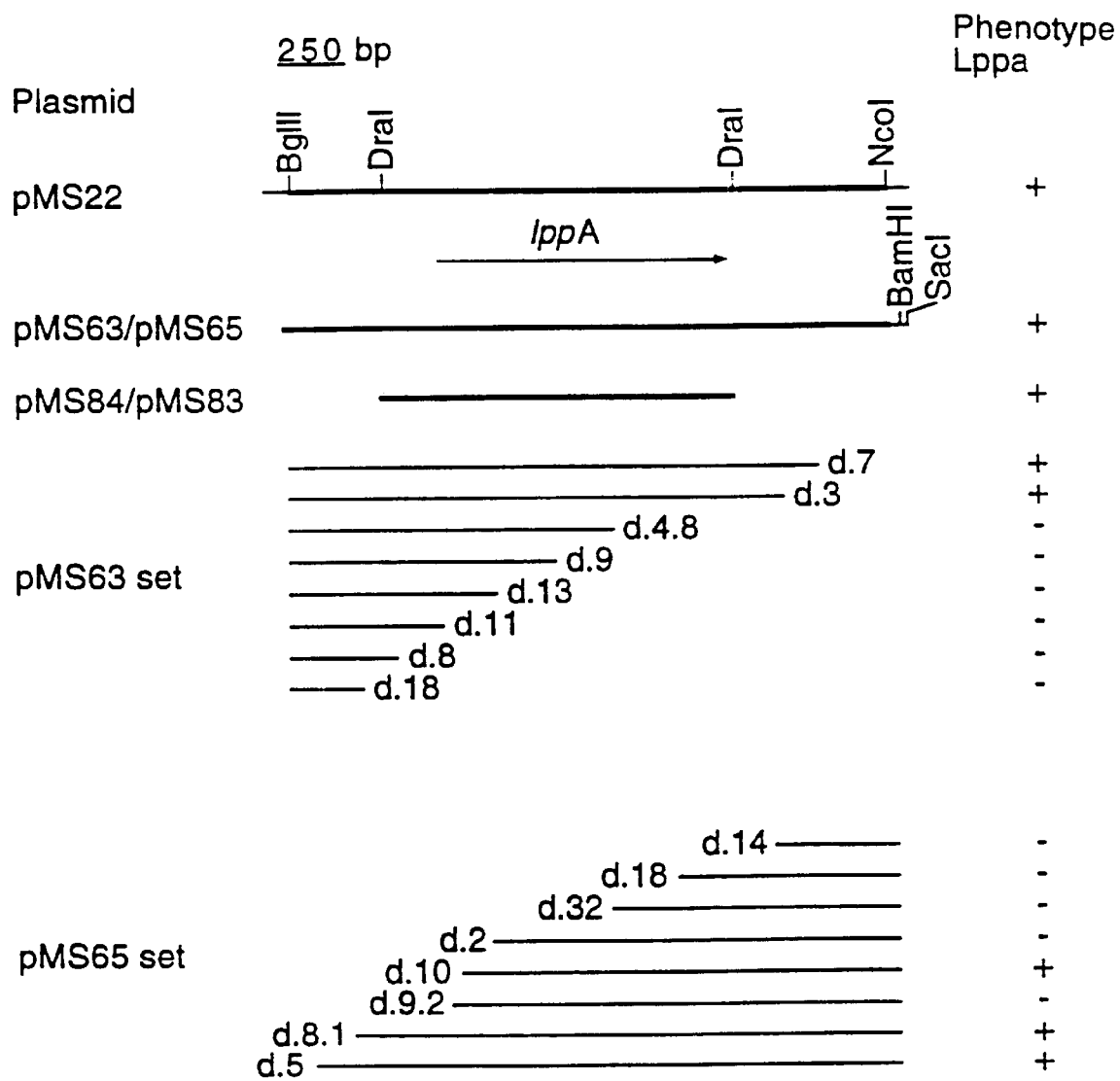
FIG. 2 shows the structure and properties of plasmids described in Example 1. The top line shows a partial restriction map of plasmid pMS22 with relevant sites shown.

The arrow indicates the location and direction of transcription of the lppA gene. The shaded bars beneath the arrow illustrate the DNA cloned in each of the indicated plasmids. Plasmid names indicated with a slash denote fragments cloned in both orientations. The lower two sets of lines show the DNA remaining in the deletion plasmids used for determining the nucleotide sequence of the lppA gene. The far right column indicates the ability of the various plasmids to direct the synthesis of LppA in JM105.

FIGS. 3A through 3B (SEQ ID NOS:3–4) shows the nucleotide sequence and deduced amino acid sequence of the gene encoding H. somnus LppB. The preprotein is encoded by nucleotide positions 872 through 1708 (amino acid residues 1 through 279). The mature protein is encoded by nucleotide positions 920 through 1708 (amino acid-residues 17 through 279).

FIGS. 4A through 4C (SEQ ID NOS:5–6) depicts the nucleotide sequence and predicted amino acid sequence of the gene encoding H. somnus LppC. The preprotein spans nucleotide positions 108 through 1850 (amino acid residues 1 through 581), with the spanning positions 171 through 1850 (amino acids 22 through 581).

FIGS. 5A through 5I (SEQ ID NOS:7–9) depicts the nucleotide sequence and predicted amino acid sequence contained in plasmid pCRR28. The sequence includes the lktA gene from P. haemolytica fused with the lppB gene.

DETAILED DESCRIPTION

The practice of the present invention will employ, unless otherwise indicated, conventional techniques of molecular biology, microbiology, virology, recombinant DNA technology, and immunology, which are within the skill of the art. Such techniques are explained fully in the literature. See, e.g., Sambrook, Fritsch & Maniatis, *Molecular Cloning: A Laboratory Manual*, Second Edition (1989); *DNA Cloning*, Vols. I and II (D. N. Glover ed. 1985); *Oligonucleotide synthesis* (M. J. Gait ed. 1984); *Nucleic Acid Hybridization* (B. D. Hames & S. J. Higgins eds. 1984); *Animal Cell Culture* (R. K. Freshney ed. 1986); *Immobilized Cells and Enzymes* (IRL press, 1986); Perbal, B., *A Practical Guide to Molecular Cloning* (1984); the series, *Methods In Enzymology* (S. Colowick and N. Kaplan eds., Academic Press, Inc.); and *Handbook of Experimental Immunology*, Vols. I–IV (D. M. Weir and C. C. Blackwell eds., 1986, Blackwell Scientific Publications).

All patents, patent applications and publications cited herein, whether supra or infra, are hereby incorporated by reference in their entirety.

A. Definitions

In describing the present invention, the following terms will be employed, and are intended to be defined as indicated below.

An "antigen" refers to a molecule containing one or more epitopes that will stimulate a host's immune system to make a humoral and/or cellular antigen-specific response. The term is also used interchangeably with "immunogen."

An "isolated" protein sequence is a protein sequence which is separate and discrete from a whole organism (live or killed) with which the protein or nucleotide sequence is normally associated in nature. Thus, a protein contained in a cell free extract would constitute an "isolated" protein, as would a protein synthetically or recombinantly produced. An "isolated" nucleotide sequence is a nucleotide sequence separate and discrete from the whole organism with which the sequence is found in nature; or a sequence devoid, in whole or part, of sequences normally associated with it in nature; or a sequence, as it exists in nature, but having heterologous sequences (as defined below) in association therewith.

The term "subunit antigen," like purified protein, refers to an antigen entity separate and discrete from a whole organism (live or killed) with which the antigen is associated in nature and is not meant to denote the method by which the antigen is obtained.

A "hapten" is a molecule containing one or more epitopes that does not stimulate a host's immune system to make a humoral or cellular response unless linked to a carrier.

The term "epitope" refers to the site on an antigen or hapten to which specific B cells and T cells respond. The term is also used interchangeably with "antigenic determinant" or "antigenic determinant site."

An "immunological response" to a composition or vaccine is the development in the host of a cellular and/or antibody-mediated immune response to the composition or vaccine of interest. Usually, such a response includes but is not limited to one or more of the following effects; the production of antibodies, B cells, helper T cells, suppressor T cells, and/or cytotoxic T cells and/or γδ T cells, directed specifically to an antigen or antigens included in the composition or vaccine of interest.

The terms "immunogenic" protein or polypeptide refers to an amino acid sequence which elicits an immunological response as described above. An "immunogenic" protein or polypeptide, as used herein, includes the full length (or near full length) sequence of the desired H. somnus protein or an immunogenic fragment thereof. By "immunogenic fragment" is meant a fragment of a polypeptide which includes one or more epitopes and thus elicits the immunological response described above. Such fragments can be identified by, e.g., concurrently synthesizing large numbers of peptides on solid supports, the peptides corresponding to portions of the haemin-binding protein molecule, and reacting the peptides with antibodies while the peptides are still attached to the supports. Such techniques are known in the art and described in, e.g., U.S. Pat. No. 4,708,871; Geysen, H. M. et al. (1984) *Proc. Natl. Acad. Sci. USA* 81:3998–4002; Geysen, H. M. et al. (1986) *Molec. Immunol.* 23:709–715, all incorporated herein by reference in their entireties. Such fragments will usually be at least about 2 amino acids in length, more preferably about 5 amino acids in length, and most preferably at least about 10 to 15 amino acids in length. There is no critical upper limit to the length of the fragment, which could comprise nearly the full length of the protein sequence, or even a fusion protein comprising fragments of two or more of the H. somnus antigens or one or more of the H. somnus antigens fused to, i.e., a bacterial, fungal, viral or protozoal antigen.

By "vertebrate subject" is meant any member of the subphylum chordata, including, without limitation, mammals such as cattle, sheep, pigs, goats, horses, and man; domestic animals such as dogs and cats; and birds, including domestic, wild and game birds such as cocks and hens including chickens, turkeys and other gallinaceous birds. The term does not denote a particular age. Thus, both adult and newborn animals are intended to be covered.

The term "polypeptide" is used in its broadest sense, i.e., any polymer of amino acids (dipeptide or greater) linked through peptide bonds. Thus, the term "polypeptide" includes proteins, oligopeptides, protein fragments, analogs, muteins, fusion proteins and the like.

"Recombinant" polypeptides refer to polypeptides produced by recombinant DNA techniques; i.e., produced from cells transformed by an exogenous DNA construct encoding the desired polypeptide. "Synthetic" polypeptides are those prepared by chemical synthesis.

A "replicon" is any genetic element (e.g., plasmid, chromosome, virus) that functions as an autonomous unit of DNA replication in vitro and in vivo; i.e., capable of replication under its own control.

A "vector" is a replicon, such as a plasmid, phage, or cosmid, to which another DNA segment may be attached so as to bring about the replication of the attached segment.

A DNA "coding sequence" or a "nucleotide sequence encoding" a particular protein, is a DNA sequence which is transcribed and translated into a polypeptide in vitro or in vivo when placed under the control of appropriate regulatory sequences. The boundaries of the coding sequence are determined by a start codon at the 5' (amino) terminus and a translation stop codon at the 3' (carboxy) terminus. A coding sequence can include, but is not limited to, procaryotic sequences, cDNA from eucaryotic mRNA, genomic DNA sequences from eucaryotic (e.g., mammalian) DNA, and even synthetic DNA sequences. A transcription termination sequence will usually be located 3' to the coding sequence.

DNA "control sequences" refers collectively to promoter sequences, ribosome binding sites, polyadenylation signals, transcription termination sequences, upstream regulatory domains, enhancers, and the like, which collectively provide for the transcription and translation of a coding sequence in a host cell. Not all of these control sequences need always be present in a recombinant vector so long as the desired gene is capable of being transcribed and translated.

"Operably linked" refers to an arrangement of elements wherein the components so described are configured so as to perform their usual function. Thus, control sequences operably linked to a coding sequence are capable of effecting the expression of the coding sequence. The control sequences need not be contiguous with the coding sequence, so long as they function to direct the expression thereof. Thus, for example, intervening untranslated yet transcribed sequences can be present between a promoter sequence and the coding sequence and the promoter sequence can still be considered "operably linked" to the coding sequence. Similarly, a coding sequence is "operably linked to" another coding sequence (i.e., in the case of a chimeric protein) when RNA polymerase will transcribe the two coding sequences into mRNA, which is then translated into the polypeptides encoded by the two coding sequences. The coding sequences need not be contiguous to one another so long as the transcribed sequence is ultimately processed to produce the desired protein.

A control sequence "directs the transcription" of a coding sequence in a cell when RNA polymerase will bind the promoter sequence and transcribe the coding sequence into mRNA, which is then translated into the polypeptide encoded by the coding sequence.

A "host cell" is a cell which has been transformed, or is capable of transformation, by an exogenous DNA sequence.

A cell has been "transformed" by exogenous DNA when such exogenous DNA has been introduced inside the cell membrane. Exogenous DNA may or may not be integrated (covalently linked) into chromosomal DNA making up the genome of the cell. In procaryotes and yeasts, for example, the exogenous DNA may be maintained on an episomal element, such as a plasmid. With respect to eucaryotic cells, a stably transformed cell is one in which the exogenous DNA has become integrated into the chromosome so that it is inherited by daughter cells through chromosome replication. This stability is demonstrated by the ability of the eucaryotic cell to establish cell lines or clones comprised of a population of daughter cell containing the exogenous DNA.

A "clone" is a population of cells derived from a single cell or common ancestor by mitosis. A "cell line" is a clone of a primary cell that is capable of stable growth in vitro for many generations.

Two DNA or polypeptide sequences are "substantially homologous" when at least about 80% (preferably at least about 90%, and most preferably at least about 95%) of the nucleotides or amino acids match over a defined length of the molecule. As used herein, substantially homologous also refers to sequences showing identity to the specified DNA or polypeptide sequence. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; *DNA Cloning*, vols I & II, supra; *Nucleic Acid Hybridization*, supra.

The term "functionally equivalent" intends that the amino acid sequence of the subject peptide is one that will elicit an immunological response, as defined above, equivalent to the response elicited by an LppA, LppB or LppC antigenic peptide having identity with either the entire coding sequence for the various proteins depicted in the figures, or an immunogenic portion thereof.

A "heterologous" region of a DNA construct is an identifiable segment of DNA within or attached to another DNA molecule that is not found in association with the other molecule in nature. Thus, when the heterologous region encodes a bacterial gene, the gene will usually be flanked by DNA that does not flank the bacterial gene in the genome of the source bacteria. Another example of the heterologous coding sequence is a construct where the coding sequence itself is not found in nature (e.g., synthetic sequences having codons different from the native gene). Allelic variation or naturally occurring mutational events do not give rise to a heterologous region of DNA, as used herein.

The term "treatment" as used herein refers to either (i) the prevention of infection or reinfection (prophylaxis), or (ii) the reduction or elimination of symptoms of the disease of interest (therapy).

B. General Methods

Central to the present invention is the discovery of certain *H. somnus* lipoproteins able to elicit an immune response in an animal to which they are administered. Specifically, the genes for three antigenic *H. somnus* lipoproteins, LppA, LppB and LppC, have been cloned and the proteins characterized. The proteins, immunogenic fragments thereof or chimeric proteins comprising the same, are provided in subunit vaccine compositions and thus problems inherent in prior vaccine compositions, such as localized and systemic side reactions, as well as immunosuppressive effects, are avoided.

The vaccine compositions can be used to treat or prevent a wide variety of *H. somnus* infections in animals. Such infections include thromboembolic meningoencephalitis (ITEME), septicemia, arthritis, and pneumonia (Corbelll, L. B., *Can. J. Vet. Res*. (1990) 54:S57–S62; Harris, F. W., and Janzen, E. D., *Can. Vet. J*. (1990) 30:816–822; Humphrey, J.

D., and Stephens, L. R., *Vet. Bull.* (1983) 53:987–1004), as well as myocarditis, pericarditis, spontaneous abortion, infertility and mastitis. Other bacterial, viral, fungal and/or protozoal antigens can also be included in the vaccine compositions, such as the *P. haemolytica* leukotoxin described further below. Thus, the compositions will also serve to prevent diseases caused by these organisms, i.e., respiratory diseases caused by *P. haemolytica*, symptoms of shipping fever and bovine respiratory disease in feedlot cattle, among others.

In addition to use in vaccine compositions, the proteins or antibodies thereto can be used as diagnostic reagents to detect the presence of *H. somnus* infection in a subject. Similarly, the genes encoding the proteins can be cloned and used to design probes for the detection of *H. somnus* in tissue samples as well as for the detection of homologous genes in other bacterial strains.

The proteins of the present invention are polypeptides from at least one of the *H. somnus* lipoproteins LppA, LppB, or LppC. These lipoproteins have DNA and amino acid sequences corresponding to those depicted in the figures. However, it is to be understood that modifications, such as deletions, additions and substitutions (generally conservative in nature), to the sequences may be made, as long as activity is not destroyed and such modifications are specifically encompassed by the terms LppA, LppB and LppC, as used herein. Furthermore, the terms denote both the precursor and mature forms of the lipoproteins.

While it is preferred to use subunit lipoproteins containing the full-length (or near full-length) sequence of the selected *H. somnus* lipoprotein, shorter sequences encoding one or more epitopes can also be employed. Accordingly, the terms LppA, LppB and LppC also encompass polypeptides including such epitopes. Epitopes can be identified and tested for immunogenicity using standard techniques such as described in, e.g., U.S. Pat. No. 4,708,871; Geysen, H. M. et al. (1984) *Proc. Natl. Acad. Sci. USA* 81:3998–4002; Geysen, H. M. et al. (1986) *Molec. Immunol.* 23:709–715, all incorporated herein by reference in their entireties. Studies with other bacterial lipoproteins have shown that the portion of the molecule responsible for biological activity resides in the N-terminal fatty acid containing region. Short peptides, including two to five amino acids covalently linked to palmitate, have been shown to possess biological activity (Bessler, W. G., et al. *J. Immunol.* (1985) 135:1900–1905). Accordingly, active proteins, having at least about 2 amino acids, more preferably 2 to 5 amino acids, and most preferably at least about 10 to 15 amino acids, will find use in the subject vaccine compositions. There is no critical upper limit to the length of the subunit antigen, which could comprise the entire lipoprotein sequence, or even a fusion protein comprising the full or partial sequences of two or more of the lipoproteins or other bacterial, viral, fungal or protozoal antigens.

Additionally, the lipoproteins (or fragments thereof) of the present invention can occur in neutral form or in the form of basic or acid addition salts depending on the mode of preparation. Such acid addition salts may involve free amino groups and basic salts may be formed with free carboxyls. Pharmaceutically acceptable basic and acid addition salts are discussed further below. In addition, the protein may be modified by combination with other biological materials such as lipids (either those normally associated with the lipoprotein or other lipids that do not destroy activity) and saccharides, or by side chain modification, such as acetylation of amino groups, phosphorylation of hydroxyl side chains, oxidation of sulfhydryl groups, glycosylation of amino acid residues, as well as other modifications of the encoded primary sequence. Thus, included within the definition of lipoproteins herein are glycosylated and unglycosylated forms, the amino acid sequences with or without associated lipids, and amino acid sequences substantially homologous to the native sequences which retain the ability to elicit an immune response.

As explained above, the proteins of the present invention are normally found in association with lipid moieties. It is likely that the fatty acid moiety present is a palmitic acid derivative. The antigens of the present invention, even though carrying epitopes derived from lipoproteins, do not require the presence of the lipid moiety. Furthermore, if the lipid is present, it need not be a lipid commonly associated with the lipoprotein, so long as the appropriate immunologic response is elicited. In any event, suitable fatty acids, such as but not limited to, palmitic acid or palmitic acid analogs, can be conveniently added to the desired amino acid sequence during synthesis, using standard techniques. For example, palmitoyl bound to S-glyceryl-L-Cys (Pam$_3$-Cys) is commercially available (e.g. through Boehringer Mannheim, Dorval, Quebec) and can easily be incorporated into an amino acid sequence during synthesis. See, e.g. Deres, K., et al. *Nature* (1989) 342:561. This is a particularly convenient method for production when relatively short amino acid sequences are used. Similarly, recombinant systems can be used which will process the expressed proteins by adding suitable fatty acids. Representative systems for recombinant production are discussed further below.

In the vaccines of the present invention, it will sometimes be preferable to have more than one epitope in the subunit antigen(s). Furthermore, it may also be desirable to include epitopes from more than one lipoprotein in the subunit antigen(s). In its simplest form, this can be achieved by employing a polypeptide encoding the complete sequence of a lipoprotein (usually encompassing more than one epitope), or by employing a combination of polypeptides encoding the sequences of two or all three of the described lipoproteins. Thus, the vaccine compositions could comprise, for example, LppA, a combination of LppA and LppB (LppA/LppB), a combination of LppA and LppC (LppA/LppC), a combination of LppB and LppC (LppB/LppC), or a combination of all three lipoproteins (LppA/LppB/LppC).

Each of the LppA, LppB and LppC antigens will be described in more detail below.

LppA

LppA appears to correspond to the major *H. somnus* 40 kDa OMP. The gene encoding LppA, lppA, has been cloned and the nucleotide sequence determined. LppA is specified by a single transcript approximately 1300 nucleotides in length. The start point is located at position 757 of FIGS. 1A through 1B (SEQ ID NOS:1–2), suggesting that transcription terminates beyond the 3'-end of the cloned DNA. One open reading frame (ORF) is present, starting at an ATG codon at position 791 and running through position 1531 of FIG. 1 (amino acid residues 1 through 247). This region appears to encode the preprotein.

The calculated molecular weight based on the sequence is 27,072. This reading frame has been confirmed by sequencing the fusion joint of two independent lppA::TnphoA gene fusions. Thus, although the predicted molecular weight is less than expected, the ORF indeed encodes the LppA protein. The anomalous molecular weight is likely due to the lipid nature of the molecule. The region downstream of the lppA gene does not contain ORFs of any significant length. Also, the LppA protein is the only polypeptide specified by the H. somnus insert in E. coli minicells. Therefore, it is likely that lppA is transcribed as a single cistron.

No significant homology between the complete LppA amino acid sequence and sequences compiled in Genbank have been found.

LppA appears to include a signal sequence. The 21 N-terminal amino acids show strong sequence homology to the signal peptide of other secreted proteins, and the sequence, Leu-Leu-Ala-Ala-Cys, at the putative cleavage site, is identical to the consensus cleavage sequence of lipoproteins from Gram-negative bacteria. Thus the mature protein spans positions 854 through 1531 (amino acid residues 22 through 247), inclusive, of FIGS. 1A through 1B (SEQ ID NOS:1–2). The ORF thus encodes a preprotein having 247 amino acid residues and a mature polypeptide having 226 amino acid residues.

The presence of the lipid moiety on the protein was shown by incorporation of radioactive palmitic acid into the natural H. somnus protein. Palmitic acid was also incorporated into the protein when it was recombinantly produced in E. coli. Synthesis of the mature LppA lipoprotein was inhibited by globomycin, showing that cleavage of the signal peptide is mediated by signal peptidase II in both organisms. Using site-directed mutagenesis, the Cys residue at the cleavage site was changed to glycine. Radiolabeled palmitate was not incorporated into the mutated protein, showing that lipid modification occurs at the Cys-22 residue.

LppB

A second lipoprotein, LppB, has been cloned and studied. The gene, lppB, also encodes a 40 kDa H. somnus outer membrane lipoprotein. This lipoprotein is antigenically distinct from LppA and plasmids harboring the lppB gene do not hybridize to plasmids encoding LppA. Lipid moieties on the molecule were detected as described above.

FIGS. 3A through 3B (SEQ ID NOS:3–4) depicts a chromosomal fragment which includes lppB. The ORF encoding LppB begins at position 872 and ends with the TAA codon at position 1709. A putative ribosome binding site, GGAG, is located upstream and a seven base pair A/T rich spacer precedes the ATG start codon. The lppB gene encodes a preprotein having 279 amino acids. The first 16 amino acids of LppB appear to specify a signal sequence. Amino acid residues 1 to 13 are followed by a lipoprotein box, Leu-Ala-Ala-Cys. This region strongly resembles signal peptides of other procaryotic lipoproteins, including LppA described above. The mature lipoprotein spans positions 920 through 1708 (amino acid residues 17 through 279) of FIGS. 3A through 3B (SEQ ID NOS:3–4). The calculated molecular mass of LppB is 31307 Daltons. Again, the discrepancy in size is probably due to the lipid nature of the protein.

LppB was shown to bind both Congo red and hemin on agar plates. LppA, on the other hand, binds neither of these proteins. It is known that some pathogenic bacteria can adsorb the aromatic dye Congo red and that this ability is strongly correlated with virulence (Daskaleros & Payne Infect. Immun. (1985) 48:165–168; Maurelli et al. Infect. Immun. (1984) 43:397–401). The molecular basis for this adsorption is unclear, although in E. coli and S. flexneri, Congo red binding has been associated with the presence of a large virulence plasmid (Maurelli et al. 1984). It has also been suggested that the ability of certain species to bind Congo red is related to their ability to sequester iron and that Congo red binding and hemin adsorption is correlated (Prpic et al. 1983). The ability of LppB to bind Congo red and hemin can be used as a selection technique in recombinant production.

LppC

The gene encoding a third H. somnus lipoprotein, LppC, has also been cloned. LppC is a 60 kDa lipoprotein, as determined by gel electrophoresis. The nucleotide sequence and predicted amino acid sequence of LppC is shown in FIGS. 4A through 4C (SEQ ID NOS:5–6). An ORF beginning at position 108 and ending at position 1850 codes for a protein with a calculated molecular weight of 63,336 Daltons. As with LppA and LppB, the preprotein includes a typical procaryotic signal sequence. The signal sequence includes the first 21 amino acids and thus the DNA coding for the mature protein begins at nucleotide position 171.

The lipid nature of this protein was confirmed as with LppA and LppB. Like LppB, LppC is able to bind both Congo red and hemin.

Production of the Lipoproteins

The above described antigens can be produced by a variety of methods. Specifically, the antigens can be isolated directly from H. somnus from outer membrane preparations, using standard purification techniques. See, e.g. Theisen, M. and Potter, A. Infect. Immun. (1992), in press. Alternatively, the antigens can be recombinantly produced as described herein. The proteins can also be synthesized, based on the described amino acid sequences, using techniques well known in the art.

For example, the proteins can be isolated from bacteria which express the same. This is generally accomplished by first preparing a crude extract which lacks cellular components and several extraneous proteins. The desired antigens can then be further purified i.e. by column chromatography, HPLC, immunoadsorbent techniques or other conventional methods well known in the art.

The proteins of the present invention can be conveniently produced as recombinant polypeptides. As explained above, these recombinant products can take the form of partial Lpp protein sequences, full-length sequences, or even fusion proteins (e.g., with an appropriate leader for the recombinant host, or with another subunit antigen sequence for H. somnus or another pathogen). In particular, chimeric proteins comprising a LppB, fused to the P. haemolytica leukotoxin gene, have been constructed and the sequence depicted in FIG. 5. The chimera in FIGS. 5A through 5I (SEQ ID NOS:7–9) includes a gene coding for LppB, fused to a truncated leukotoxin molecule, encoded by the lktA gene of P. haemolytica (available from ATCC Accession No. 68283). Such chimeric proteins can be produced using recombinant techniques described herein and, e.g., in U.S. Pat. No. 4,366,246; Hughes, H. P. A. et al. (1992) Infect. Immun. 60:565–570; PCT Publication No. WO 88/00971 (published Feb. 11, 1988); and allowed U.S. patent application Ser. No. 07/571,301.

Genes encoding the subject proteins can be identified by constructing gene libraries, using the resulting clones to transform E. coli and pooling and screening individual colonies using polyclonal serum or monoclonal antibodies to the desired antigen.

Alternatively, once the amino acid sequences of the subject proteins are determined, oligonucleotide probes which contain the codons for a portion of the determined amino acid sequences can be prepared and used to screen DNA libraries for genes encoding the subject proteins. The basic strategies for preparing oligonucleotide probes and DNA libraries, as well as their screening by nucleic acid hybridization, are well known to those of ordinary skill in the art. See, e.g., DNA Cloning: Vol. I, supra; Nucleic Acid Hybridization, supra; Oligonucleotide Synthesis, supra; T. Maniatis et al., supra. Once a clone from the screened library has been identified by positive hybridization, it can be confirmed by restriction enzyme analysis and DNA sequencing that the particular library insert contains a gene for the desired protein.

Alternatively, DNA sequences encoding the proteins of interest can be prepared synthetically rather than cloned. The DNA sequence can be designed with the appropriate codons for the particular amino acid sequence. In general, one will select preferred codons for the intended host if the sequence will be used for expression. The complete sequence is assembled from overlapping oligonucleotides prepared by standard methods and assembled into a complete coding sequence. See, e.g., Edge (1981) *Nature* 292:756; Nambair et al. (1984) *Science* 223:1299; Jay et al. (1984) *J. Biol. Chem.* 259:6311.

Once coding sequences for the desired proteins have been prepared or isolated, they can be cloned into any suitable vector or replicon. Numerous cloning vectors are known to those of skill in the art, and the selection of an appropriate cloning vector is a matter of choice. Examples of recombinant DNA vectors for cloning and host cells which they can transform include the bacteriophage λ (*E. coli*), pBR322 (*E. coli*), pACYC177 (*E. coli*), pKT230 (gram-negative bacteria), pGV1106 (gram-negative bacteria), pLAFR1 (gram-negative bacteria), pME290 (non-*E. coli* gram-negative bacteria), pHV14 (*E. coli* and *Bacillus subtilis*), pBD9 (Bacillus), pIJ61 (Streptomyces), pUC6 (Streptoihyces), YIp5(Saccharomyces), YCp19 (Saccharomyces) and bovine papilloma virus (mammalian cells). See, generally, *DNA Cloning*: Vols. I & II, supra; T. Maniatis et al., supra; B. Perbal, supra.

The gene can be placed under the control of a promoter, ribosome binding site (for bacterial expression) and, optionally, an operator (collectively referred to herein as "control" elements), so that the DNA sequence encoding the desired protein is transcribed into RNA in the host cell transformed by a vector containing this expression construction. The coding sequence may or may not contain a signal peptide or leader sequence. As explained above, the lipoproteins of the instant invention include signal sequences. Thus the lipoprotein genes can be expressed with the native signal sequences. Alternatively, heterologous signal sequences can be used. The subunit antigens of the present invention can be expressed using, for example, the *E. coli* tac promoter or the protein A gene (spa) promoter and signal sequence. Leader sequences can be removed by the bacterial host in post-translational processing. See, e.g., U.S. Pat. Nos. 4,431,739; 4,425,437; 4,338,397.

Other regulatory sequences may also be desirable, which allow for regulation of the expression of the protein sequences relative to the growth of the host cell. Regulatory sequences are known to those of skill in the art, and examples include those which cause the expression of a gene to be turned on or off in response to a chemical or physical stimulus, including the presence of a regulatory compound. other types of regulatory elements may also be present in the vector, for example, enhancer sequences.

The control sequences and other regulatory sequences may be ligated to the coding sequence prior to insertion into a vector, such as the cloning vectors described above. Alternatively, the coding sequence can be cloned directly into an expression vector which already contains the control sequences and an appropriate restriction site.

In some cases it may be necessary to modify the coding sequence so that it may be attached to the control sequences with the appropriate orientation; i.e., to maintain the proper reading frame. It may also be desirable to produce mutants or analogs of the Lpp protein of interest. Mutants or analogs may be prepared by the deletion of a portion of the sequence encoding the protein, by insertion of a sequence, and/or by substitution of one or more nucleotides within the sequence. Techniques for modifying nucleotide sequences, such as site-directed mutagenesis, are described in, e.g., Sambrook et al., supra; *DNA Cloning*, Vols. I and II, supra; *Nucleic Acid Hybridization*, supra.

The expression vector is then used to transform an appropriate host cell. A number of mammalian cell lines are known in the art and include immortalized cell lines available from the American Type Culture Collection (ATCC), such as, but not limited to, Chinese hamster ovary (CHO) cells, HeLa cells, baby hamster kidney (BHK) cells, monkey kidney cells (COS), human hepatocellular carcinoma cells (e.g., Hep G2), Madin-Darby bovine kidney ("MDBK") cells, as well as others. Similarly, bacterial hosts such as *E. coli, Bacillus subtilis*, and Streptococcus spp., will find use with the present expression constructs. Yeast hosts useful in the present invention include inter alia, *Saccharomyces cerevisiae, Candida albicans, Candida maltosa, Hansenula polymorpha, Kluyveromyces fragilis, Kluyveromyces lactis, Pichia guillerimondii, Pichia pastoris, Schizosaccharomyces pombe* and *Yarrowia lipolytica*. Insect cells for use with baculovirus expression vectors include, inter alia, *Aedes aegypti, Autographa californica, Bombyx mori, Drosophila melanogaster, Spodoptera frugiperda*, and *Trichoplusia ni.*

Depending on the expression system and host selected, the proteins of the present invention are produced by growing host cells transformed by an expression vector described above under conditions whereby the protein of interest is expressed. The protein is then isolated from the host cells and purified. If the expression system secretes the protein into growth media, the protein can be purified directly from the media. If the protein is not secreted, it is isolated from cell lysates. The selection of the appropriate growth conditions and recovery methods are within the skill of the art.

The proteins of the present invention may also be produced by chemical synthesis such as solid phase peptide synthesis, using known amino acid sequences or amino acid sequences derived from the DNA sequence of the genes of interest. Such methods are known to those skilled in the art. Chemical synthesis of peptides may be preferable if a small fragment of the antigen in question is capable of raising an immunological response in the subject of interest.

The proteins of the present invention or their fragments can be used to produce antibodies, both polyclonal and monoclonal. If polyclonal antibodies are desired, a selected mammal, (e.g., mouse, rabbit, goat, horse, etc.) is immunized with an antigen of the present invention, or its fragment, or a mutated antigen. Serum from the immunized animal is collected and treated according to known procedures. If serum containing polyclonal antibodies is used, the polyclonal antibodies can be purified by immunoaffinity chromatography, using known procedures.

Monoclonal antibodies to the proteins of the present invention, and to the fragments thereof, can also be readily produced by one skilled in the art. The general methodology for making monoclonal antibodies by using hybridoma technology is well known. Immortal antibody-producing cell lines can be created by cell fusion, and also by other techniques such as direct transformation of B lymphocytes with oncogenic DNA, or transfection with Epstein-Barr virus. See, e.g., M. Schreier et al., *Hybridoma Techniques* (1980); Hammerling et al., *Monoclonal Antibodies and T-cell Hybridomas* (1981); Kennett et al., *Monoclonal Antibodies* (1980); see, also, U.S. Pat. Nos. 4,341,761; 4,399, 121; 4,427,783; 4,444,887; 4,452,570; 4,466,917; 4,472, 500, 4,491,632; and 4,493,890. Panels of monoclonal antibodies produced against the antigen of interest, or fragment thereof, can be screened for various properties; i.e., for isotype, epitope, affinity, etc. Monoclonal antibodies are useful in purification, using immunoaffinity techniques, of the individual antigens which they are directed against.

Vaccine Formulations and Administration

The *H. somnus* proteins of the present invention can be formulated into vaccine compositions, either alone or in combination with other antigens, for use in immunizing subjects as described below. Methods of preparing such formulations are described in, e.g., *Remington's Pharmaceutical Sciences*, Mack Publishing Company, Easton, Pa., 15th edition, 1975.

Typically, the vaccines of the present invention are prepared as injectables, either as liquid solutions or suspensions. Solid forms suitable for solution in or suspension in liquid vehicles prior to injection may also be prepared. The preparation may also be emulsified or the active ingredient encapsulated in liposome vehicles. The active immunogenic ingredient is generally mixed with a compatible pharmaceutical vehicle, such as, for example, water, saline, dextrose, glycerol, ethanol, or the like, and combinations thereof. In addition, if desired, the vehicle may contain minor amounts of auxiliary substances such as wetting or emulsifying agents and pH buffering agents.

Adjuvants which enhance the effectiveness of the vaccine may also be added to the formulation. Adjuvants may include for example, muramyl dipeptides, avridine, aluminum hydroxide, oils, saponins, cytokines, and other substances known in the art.

The protein may be linked to a carrier in order to increase the immunogenicity thereof. Suitable carriers include large, slowly metabolized macromolecules such as proteins, including serum albumins, keyhole limpet hemocyanin, immunoglobulin molecules, thyroglobulin, ovalbumin, and other proteins well known to those skilled in the art; polysaccharides, such as sepharose, agarose, cellulose, cellulose beads and the like; polymeric amino acids such as polyglutamic acid, polylysine, and the like; amino acid copolymers; and inactive virus particles.

The protein substrates may be used in their native form or their functional group content may be modified by, for example, succinylation of lysine residues or reaction with Cys-thiolactone. A sulfhydryl group may also be incorporated into the carrier (or antigen) by, for example, reaction of amino functions with 2-iminothiolane or the N-hydroxysuccinimide ester of 3-(4-dithiopyridyl propionate. Suitable carriers may also be modified to incorporate spacer arms (such as hexamethylene diamine or other bifunctional molecules of similar size) for attachment of peptides.

Other suitable carriers for the proteins of the present invention include VP6 polypeptides of rotaviruses, or functional fragments thereof, as disclosed in U.S. Pat. No. 5,071,651, incorporated herein by reference. Also useful is a fusion product of a viral protein and the subject immunogens made by methods disclosed in U.S. Pat. No. 4,722,840. Still other suitable carriers include cells, such as lymphocytes, since presentation in this form mimics the natural mode of presentation in the subject, which gives rise to the immunized state. Alternatively, the proteins of the present invention may be coupled to erythrocytes, preferably the subject's own erythrocytes. Methods of coupling peptides to proteins or cells are known to those of skill in the art.

Furthermore, the proteins (or complexes thereof) may be formulated into vaccine compositions in either neutral or salt forms. Pharmaceutically acceptable salts include the acid addition salts (formed with the free amino groups of the active polypeptides) and which are formed with inorganic acids such as, for example, hydrochloric or phosphoric acids, or such organic acids as acetic, oxalic, tartaric, mandelic, and the like. Salts formed from free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

Injectable vaccine formulations will contain a "therapeutically effective amount" of the active ingredient, that is, an amount capable of eliciting an immune response in a subject to which the composition is administered. The exact amount is readily determined by one skilled in the art. The active ingredient will typically range from about 1% to about 95% (w/w) of the composition, or even higher or lower if appropriate. With the present vaccine formulations, 50 to 500 µg of active ingredient per ml of injected solution should be adequate to raise an immunological response when a dose of 1 to 3 ml per animal is administered. To immunize a subject, the vaccine is generally administered parenterally, usually by intramuscular injection. Other modes of administration, however, such as subcutaneous, intraperitoneal and intravenous injection, are also acceptable. The quantity to be administered depends on the animal to be treated, the capacity of the animal's immune system to synthesize antibodies, and the degree of protection desired. Effective dosages can be readily established by one of ordinary skill in the art through routine trials establishing dose response curves. The subject is immunized by administration of the vaccine in at least one dose, and preferably two doses. Moreover, the animal may be administered as many doses as is required to maintain a state of immunity to *H. somnus* infection.

As explained above, LppA, LppB and LppC, chimeric proteins comprising one or more of these antigens, or immunogenic fragments thereof, or cell free extracts including the same, can be administered either alone or in combination in one or several vaccine formulations. If used in combination, the antigens can be administered in the same formulation or provided as separate entities. Furthermore, if separate compositions are used, the timing of administration may be concurrent or staggered.

Additional vaccine formulations which are suitable for other modes of administration include suppositories and, in some cases, aerosol, intranasal, oral formulations, and sustained release formulations. For suppositories, the vehicle composition will include traditional binders and carriers, such as, polyalkaline glycols, or triglycerides. Such suppositories may be formed from mixtures containing the active ingredient in the range of about 0.5% to about 10% (w/w), preferably about 1% to about 2%. Oral vehicles include such normally employed excipients as, for example, pharmaceutical grades of mannitol, lactose, starch, magnesium, stearate, sodium saccharin cellulose, magnesium carbonate, and the like. These oral vaccine compositions may be taken in the form of solutions, suspensions, tablets, pills, capsules, sustained release formulations, or powders, and contain from about 10% to about 95% of the active ingredient, preferably about 25% to about 70%.

Intranasal formulations will usually include vehicles that neither cause irritation to the nasal mucosa nor significantly disturb ciliary function. Diluents such as water, aqueous saline or other known substances can be employed with the subject invention. The nasal formulations may also contain preservatives such as, but not limited to, chlorobutanol and benzalkonium chloride. A surfactant may be present to enhance absorption of the subject proteins by the nasal mucosa.

Controlled or sustained release formulations are made by incorporating the protein into carriers or vehicles such as liposomes, nonresorbable impermeable polymers such as ethylenevinyl acetate copolymers and Hytrel® copolymers, swellable polymers such as hydrogels, or resorbable polymers such as collagen and certain polyacids or polyesters such as those used to make resorbable sutures. The proteins can also be delivered using implanted mini-pumps, well known in the art.

The novel proteins of the instant invention can also be administered via a carrier virus which expresses the same. Carrier viruses which will find use with the instant invention include but are not limited to the vaccinia and other pox viruses, adenovirus, and herpes virus. By way of example, vaccinia virus recombinants expressing the novel proteins can be constructed as follows. The DNA encoding the particular protein is first inserted into an appropriate vector so that it is adjacent to a vaccinia promoter and flanking vaccinia DNA sequences, such as the sequence encoding thymidine kinase (TK). This vector is then used to transfect cells which are simultaneously infected with vaccinia. Homologous recombination serves to insert the vaccinia promoter plus the gene encoding the instant protein into the viral genome. The resulting TKrecombinant can be selected by culturing the cells in the presence of 5-bromodeoxyuridine and picking viral plaques resistant thereto.

An alternative route of administration involves gene therapy or nucleic acid immunization. Thus, nucleotide sequences (and accompanying regulatory elements) encoding the subject proteins can be administered directly to a subject for in vivo translation thereof. Alternatively, gene transfer can be accomplished by transfecting the subject's cells or tissues ex vivo and reintroducing the transformed material into the host. DNA can be directly introduced into the host organism, i.e., by injection (see International Publication No. WO/90/11092; and Wolff et al., *Science* (1990) 247:1465–1468). Liposome-mediated gene transfer can also be accomplished using known methods. See, e.g., Hazinski et al., *Am. J. Respir. Cell Mol. Biol.* (1991) 4:206–209; Brigham et al., *Am. J. Med. Sci.* (1989) 298:278–281; Canonico et al., *Clin. Res.* (1991) 39:219A; and Nabel et al., *Science* (1990) 249:1285–1288. Targeting agents, such as antibodies directed against surface antigens expressed on specific cell types, can be covalently conjugated to the liposomal surface so that the nucleic acid can be delivered to specific tissues and cells susceptible to *H. somnus* infection.

Below are examples of specific embodiments for carrying out the present invention. The examples are offered for illustrative purposes only, and are not intended to limit the scope of the present invention in any way.

Deposits of Strains Useful in Practicing the Invention

A deposit of biologically pure cultures of the following strains was made with the American Type Culture Collection, 12301 Parklawn Drive, Rockville, Md. The accession number indicated was assigned after successful viability testing, and the requisite fees were paid. Access to said cultures will be available during pendency of the patent application to one determined by the Commissioner to be entitled thereto under 37 CFR 1.14 and 35 USC 122. All restriction on availability of said cultures to the public will be irrevocably removed upon the granting of a patent based upon the application. Moreover, the designated deposits will be maintained for a period of thirty (30) years from the date of deposit, or for five (5) years after the last request for the deposit; or for the enforceable life of the U.S. patent, whichever is longer. Should a culture become nonviable or be inadvertently destroyed, or, in the case of plasmid-containing strains, lose its plasmid, it will be replaced with a viable culture(s) of the same taxonomic description.

| Strain | Deposit Date | ATCC No. |
|---|---|---|
| pMS88 in JM105 | April 7, 1992 | 68956 |
| pMS103 in JM105 | April 7, 1992 | 68957 |
| pCRR27 in DH5 α-F'lac$^{Iq}$ | April 7, 1992 | 68958 |

C. Experimental

Materials and Methods

Enzymes were purchased from commercial sources, and used according to the manufacturers' directions. Radionucleotides and nitrocellulose filters were also purchased from commercial sources.

In the cloning of DNA fragments, except where noted, all DNA manipulations were done according to standard procedures. See Sambrook et al., supra. Restriction enzymes, T$_4$ DNA ligase, *E. coli*, DNA polymerase I, Klenow fragment, and other biological reagents were purchased from commercial suppliers and used according to the manufacturers' directions. Double stranded DNA fragments were separated on agarose gels.

Bacterial Strains, Plasmids and Growth Condition.

*E. coli* DH5α(φ80, lacZΔM15, endA1, recA1, hsdR17 ($r_k$,$m_k$+),supE44, thi-1, ,gyrA96, relA1 Δ(lacZYA-argF), U169)/'lacI$^q$proAB+lacZΔ M15, Tn5 (IKm$^R$); and JM105 (endA1, thi, rpsL, sbcB15, hsdR4, Δlac-proAB), [F'traD36, proAB+, lacI$^q$ZΔM15)] are available commercially (i.e. Stratogene) and CC118 (aroD139, Δ(ara,leu)7697, ΔlacX74, phoAΔ20, galE, galK, thi, rpsE, rpoB, argE$_{am}$, recA1) from C. Manoil, Harvard University (Manoil, C., and Beckwith, *J. Proc. Natl. Acad. Sci. USA* (1985) 82:8129–8133). *E. coli* strains were grown in Luria broth (LB) or M63 (Miller, J. H., *Experiments in Molecular Genetics*, (1972) Cold Spring Harbor Laboratory, Cold Spring Harbor, N.Y.). Ampicillin was used at 100 μg/ml and kanamycin at 25 μg/ml unless otherwise indicated. *H. somnus* strain HS25 has been used in challenge experiments to induce experimental Haemophilosis in calves (Harland, R. J., et al. *Conf. Res. Work. Anim. Dis.* 71st (1990) 29:6). Growth conditions for strain HS25, the plasmid pGH433, and the construction of the genomic library have been described (Theisen, M., and Potter, A. A. *J. Bacteriol.* (1992) 174:17–23). For iron-restricted growth, Brain Heart Infusion broth (BHI-TT) (Difco Laboratories) containing 0.1% Tris base and 0.001% thiamine monophosphate was supplemented with the iron chelator 2,2-dipyridyl (Sigma Chemical Co., St. Louis, Mo.) to a final concentration of 100 μM. Iron-replete bacteria were grown in BHI-TT containing 50 μM Fe(NO$_3$)$_3$.

DNA Techniques.

Restriction enzymes, Klenow fragment of *E. coli* DNA polymerase I, T4 DNA ligase, and exonuclease III were used as recommended by the suppliers. DNA sequencing was accomplished by the chain termination method, essentially as described by Messing, 1983 (Manoil, C., and Beckwith, J., *Science* (1986) 233:1403–1408). Primer extension was performed as previously described (Theisen, M., et al. *Infect. Immun.* (1992) 60:826–831).

Screening of H. somnus Genomic Library.

Recombinant plasmids were transformed into E. coli strain JM105 and plated on LB agar plates containing 0.05% Congo red (for LppB and LppC). After two days of incubation at 37° C. approximately 0.5% of the colonies turned dark red. Congo red binding colonies were picked and purified to single colonies on identical plates. One of each was then tested for the expression of H. somnus antigens by the colony blot method (French, B. T., et al. Anal. Biochem. (1986) 156:417–423). LppA was screened by the colony blot method (French, B. T., et al. Anal. Biochem. (1986).

Transposon TnphoA Mutagenesis.

Fusions of lppA to TnphoA were created with λ::TnphoA (Gutierrez, C., et al. J. Mol. Biol. (1987) 195:289–297). In this system, alkaline phosphatase (AP) activity is only obtained if TnphoA transposes onto a DNA sequence in such a way that AP is fused in frame and downstream of an expressed coding sequence containing appropriate membrane insertional sequences (Hoffman, C. S., and Wright, A. Proc. Natl. Acad. Sci USA (1985) 82:5107–5111; Manoil, C., and Beckwith, J. Proc. Natl. Acad. Sci. USA (1985) 82:8129–8133; Manoil, C., and Beckwith, J. Science (1986) 233:1403–1408). Plasmid pMS22 was transformed into strain CC118. The resulting strain was infected with λ::TnphoA and grown for 15 hours at 30° C. Aliquots were plated on LB agar supplemented with 300 μg/ml kanamycin, 100 μg/ml ampicillin, and 40 μg/ml 5-bromo-4-chloro-3-indoyl phosphate (BCIP). The plates were incubated at 30° C. for 2–3 days, and plasmid DNA was extracted from five pools of blue colonies and used to transform CC118 cells. Individual AP$^+$ (blue) colonies were isolated at 37° C. and their plasmid DNA analyzed by restriction mapping.

PAGE and Immunoblotting.

SDS-PAGE of H. somnus and E. coli proteins was performed in the Laemmli system (Laemmli, U. K., Nature (1970) 227:680–685) or by using the Tricine-SDS polyacrylamide gels with a 16.5% T, 6% C separating gel (Schagger, H., and von Jagow, G. Anal. Biochem. (1987) 166:368–379). Transfer of proteins onto nitrocellulose membranes was performed as recommended by the manufacturer. Blots were incubated with bovine serum diluted 1:500 with TBS-1% BSA (10 mM Tris-Cl pH 7.5, 140 mM NaCl) for two hours. The antiserum used was bovine hyperimmune serum against live H. somnus HS25 (Theisen & Potter, 1992). After three washes in TBS containing 0.5% Tween 20, seroreactive proteins were detected with goat antibovine-IgG coupled to alkaline phosphatase (Kirkegaard and Perry) at 1:5000 in TBS-1% BSA. Alkaline phosphatase activity was visualized using the NBT/BCIP system as described by the supplier (Promega). Prestained or non-stained protein standards were obtained from BioRad.

Hybridization Techniques.

Northern (RNA) blotting was performed as described by Maniatis. RNA was extracted from H. somnus and E. coil by standard techniques (Theisen, M. and Potter, A. A. J. Bacteriol. (1992), in press) and electrophoresed through 1.5% agarose gels containing formaldehyde. Three micrograms of RNA was used per lane. The RNA was blotted to nitrocellulose membrane and hybridized to DNA probes labelled at the 5'-end. After hybridization, blots were washed twice in 0.1×SSC, 0.5% SDS for two hours at 50° C.

Analysis of Plasmid Encoded Proteins.

Minicells were isolated from cultures of BD1854 containing the appropriate plasmids by centrifugation on a 5%–25% sucrose gradient, labelled with [$^{35}$S]methionine, and subjected to SDS-PAGE. The proteins were electroblotted on to nitrocellulose membrane and antigen was detected using hyperimmune serum against HS25. The position of the labelled polypeptides was then determined by autoradiography of the western blot.

Labeling of Proteins with [$^3$H]Palmitate.

E. coli strain DH5αF'IQ harboring the specified plasmids was grown in M63 medium supplemented with glycerol (0.5% w/v) and casamino acids (2% w/v). H. somnus strain HS25 was grown in BHI-TT medium. To exponentially growing cells (4×10$^8$ cells/ml), [$^3$H]palmitate (5 mCi/ml) was added to a final concentration of 50 μCi/ml, and incubation was continued for two hours. Labeling was terminated by precipitation with trichloroacetic acid (10% w/v) for 30 min on ice. When indicated, globomycin (Sankyo Co. Tokyo, Japan) (10 mg/ml in dimethyl sulfoxide) was added at 100 μg/ml, 5 min prior to the addition of palmitate. Proteins were pelleted by centrifugation at 15000×g for 20 min, and the pellets were washed twice with methanol to remove lipids. The dried pellets were resuspended in sample buffer and analyzed by Tricine-SDS PAGE. the radiolabeled protein bands in the dried gel were detected by fluorography.

Oligonucleotide-directed Mutagenesis.

A 33-residue synthetic oligonucleotide with the sequence 5'-TGTATTATTAGCAGCT<u>G</u>GTAATGAAAAAAATAA (SEQ ID NO:10) was synthesized to alter the Cys-22 residue of the LppA protein (the underlined base differs from the wild-type sequence). The point mutation in the resulting plasmid pMS67 was verified by DNA sequencing.

EXAMPLE 1

Cloning and Characterization of LppA

A. Cloning lppA in E. coli

A genomic library of H. somnus HS25 DNA was constructed by cloning 2- to 7-kb fragments, generated by partial Sau3A restriction, into the plasmid expression vector pGH433, and positive transformants were detected by the colony blot method (French, B. T., et al. Anal. Biochem. (1986) 156:417–423) using antiserum against the H. somnus strain HS25. Twenty-eight positive clones were identified and kept for further analysis. To identify the plasmid-encoded proteins reacting with the serum, whole cell lysates of IPTG-induced cell cultures were examined by PAGE and subsequent Western blotting. Three plasmids encoding a seroreactive protein with an M$_r$ of approximately 40,000 were identified. One of these, with a DNA insert of 2-kb, was designated pMS22. Using the radiolabeled insert of pMS22 as a probe, it was shown that the three plasmids contained common sequences, indicating that the 40 kDa recombinant proteins were identical. A Western blot of protein synthesized by E. coli JM105/pMS22 compared with cell fractions of H. somnus. It is apparent that the seroreactive LppA protein is predominantly present in the outer membrane fractions of H. somnus and that it comigrates with the recombinant 40 kDa protein. Moreover, serum from calves immunized with the recombinant LppA protein reacts strongly with the native 40 kDa OMP of H. somnus.

B. Analysis of Recombinant Plasmids

To subclone the lppA gene and construct, plasmids suitable for exonuclease III degradation of the cloned region, the BglII-NcoI fragment of pMS22 was cloned into pTZ18R (FIG. 2). Two plasmids pMS63 and pMS65, with the insert in opposite orientations, were obtained. Both expressed the LppA protein, indicating that the gene is transcribed from a promoter located on the insert DNA. To generate a series of nested deletions, plasmids pMS63 and pMS65 were each cut at the unique SacI and BamHI sites (FIG. 2) and subjected to exonuclease degradation, removal of overhang by S1 nuclease, and religation. A number of plasmids were analyzed, the extent of the degradation (as judged by restriction mapping or DNA sequencing) was compared with the phenotype (FIG. 2). It appears from this deletion experiment that the lppA gene is located between the deletion endpoints of d.3 and d.8.1 because plasmids with a larger insert are LppA$^+$, whereas plasmids with deletion going further into the insert are LppA$^-$. This is true with one exception, namely d.10, which produces a seroreactive truncated version of the LppA protein with an M$_r$ of approximately 37,000 (data not shown). DNA sequencing of the deletion endpoints of the two plasmids revealed that in d.10, the α-peptide of lacZ is fused in frame with the lppA ORF (see below), thereby allowing the gene to be transcribed from lacP or another vector-encoded promoter and translation from the lacZ translational start site. In contrast, lacZ in d.9 is fused out of frame with the lppA ORF.

C. DNA Sequencing and Analysis

The complete DNA sequence of both strands of lppA was determined by the dideoxy method with modified T7 DNA polymerase and single-stranded DNA as the template. The sequence is shown in FIGS. 1A through 1B (SEQ ID NOS:1–2). Only one ORF sufficiently long to encode the lppA gene product is present on the sequenced DNA. It begins with an ATG codon located at position 791–793 and terminates with the TAA stop codon at position 1532–1534. This ORF would encode a polypeptide with a molecular weight of 27,072. The ATG start codon is preceded by a purine-rich sequence <u>AATGAG</u> (underlined bases are complementary to 16 S rRNA), which serves as a ribosome binding site in *E. coli* (Theisen, M., and Potter, A. A. *Infect. Immun.* (1992), in press).

The proposed reading frame was confirmed by sequencing two independent lppA::TnphoA gene fusions (see FIGS. 1A through 1B (SEQ ID NOS:1–2). Further proof that the indicated ORF was lppA was obtained by subcloning the DraI fragment of pMS22 (FIG. 2) into the SmaI site of pTZ18R and generating pMS83 and pMS84, with the insert in opposite orientations. DraI cuts 209 base pairs upstream of the putative ATG start codon and immediately downstream of the TAA stop codon. The lppA protein was expressed in JM105 harboring both plasmids. The N-terminal part of the predicted polypeptide strongly resembles a signal peptide, and the amino acid sequence Leu-Leu-Ala-Ala-Cys at position 842–856 is highly homologous to the consensus cleavage site found in bacterial lipoproteins (von Gabin, A., et al. *Proc. Natl. Acad. Sci. USA* (1983) 80:652–657).

D. Identification of the 5' Terminus of lppA mRNA.

The 5' terminus of the lppA transcript was determined by primer extension mapping. The DNA used as primer was a synthetic 5'-end labeled oligonucleotide complementary to nucleotides between 817 and 835. mRNA was isolated from the *H. somnus* strain HS25 and the two *E. coli* strains JM105/pMS65(LppA$^+$)and JM105/pGH433 (LppA$^-$). One major lppA transcript beginning with the A residue at position 756 (FIGS. 1A through 1B (SEQ ID NOS:1–2), is produced in both HS25 and JM105/pMS65. No product was observed in cells harboring the plasmid vector pGH433. A Pribnow box and −35 region, characteristic of *E. coli* promoters (Harley, C. B., and Reynolds, R. P. *Nuc. Acids Res.* (1987) 15:2343–2361), are located at positions 744 through 749 (TATGCT) and position 722 through 727 (TTATCA), respectively.

E. Post-translational Modification of the LppA Protein.

Because the deduced amino acid sequence of the LppA protein contains a sequence identical to the consensus sequence Leu-Ala(Gly)-Ala(Gly)-Cys for lipid modification in *E. coli* (von Gabin et al., 1983), the lppA gene product may be a lipoprotein. In order to test whether the LppA protein was lipid modified, [$^3$H]palmitate was incorporated into *H. somnus* HS25 and the two *E. coli* strains, DH5αF'IQ/pMS65 and DH5αF'IQ/pTZ18R. Proteins from whole cell lysates were separated by PAGE and transferred to nitrocellulose membranes. The lppA gene product was identified by immunoblotting with antiserum against HS25. At least ten *H. somnus* proteins were labeled with palmitate. One of these was a 40 kDa protein which reacted strongly with *H. somnus* antiserum, showing that it was the lppA gene product. Palmitate was also incorporated into the recombinant lppA gene product since a radiolabeled, immunoreactive 40 kDa protein comigrating with the LppA protein from HS25 was detected in cells harboring pMS65 but not in the plasmid vector pTZ18R. Thus, the *H. somnus* lppA gene product is lipid modified in *E. coli*. Treatment of cells with globomycin leads to the accumulation of unprocessed lipoprotein, and both the natural *H. somnus* LppA and recombinant LppA protein are predominantly present as a larger, putative precursor form in globomycin-treated cells.

To determine if lipid modification of the LppA protein occurs at the cysteine residue Cys-22, the cysteine codon (TGT) was changed to a glycine codon (GGT) generating plasmid pMS67. Cells harboring pMS67 were LppA$^+$. However, only a seroreactive protein comigrating with the larger precursor form was detected in a Western blot. Globomycin did not alter the mobility of the mutated LppA protein, indicating that the mutated LppA protein was no longer a substrate for signal peptidase II. Moreover, this protein was not labeled with palmitate, showing that lipid modification occurs at the Cys-22 residue.

EXAMPLE 2

Cloning and Characterization of LppB

A. Cloning of the Gene for LppB

A genomic library in plasmid pGH433, constructed as described above, was transformed into JM105 and among several thousand ampicillin-resistant transformants approximately 0.1% were found to bind Congo red on Congo red agar plates (Crb+). The *E. coli* strain JM105 had only a modest ability to bind Congo red on these plates. Twenty Crb+ transformants were screened with hyperimmune serum in a colony blot assay, and five were found to be seroreactive. Western blots (immunoblots) of proteins from whole cells separated on polyacrylamide gels showed that one transformant contained a plasmid (pMS10) encoding an approximately 60 kDa seroreactive protein, three transformants contained plasmids (pMS11, pMS14 and pMS15) encoding an approximately 40 kDa seroreactive protein, and one contained a plasmid (pCRx) coding for a 15 kDa antigen. The radiolabeled DNA insert from pMS11 was found to hybridize to pMS14, pMS15 and *H. somnus*, but not to plasmids pMs10 and pCRx, indicating that the three 40 kDa proteins were identical, but different from the 60 kDa and 15 kDa antigens. Also, the same insert did not hybridize to plasmid pMS22, encoding LppA (Theisen et al., 1992) showing that pMS11 encodes a novel 40 kDa protein.

Both JM105/pMS11 and JM105/pMS10 form small dark colonies on minimal plates containing 0.01% hemin, suggesting that the 40 kDa and 60 kDa proteins could be hemin-binding.

B. Location of the Gene for LppB

The 1.9 kb insert isolated from pMS11 was subcloned in the SmaI site of pTZ18R using *E. coli* JM105 as the host strain. Two plasmids, pMS92 and pMS96, were obtained, carrying the insert in opposite orientations. LppB was expressed from both plasmids indicating that lppB is transcribed from a promoter located on the insert DNA. The addition of 2 mM IPTG to the growth medium increased lppB expression from pMS11 approximately four fold (as judged by a western blot) indicating that lppB was on the DNA insert. The indicated plasmids were transformed into a minicell producing strain, and plasmid encoded proteins were analyzed by PAGE. The plasmids pMS11, pMS92 and pMS105 all encode an LppB protein. Thus, LppB must be located downstream on the AhaII site at base 641 in FIGS. 3A through 3B (SEQ ID NOS:3–4).

C. Nucleotide Sequence Analysis

To generate a series of nested deletions for sequencing, plasmids pMS92 and pMS96 were each cut at the unique SacI and BamHI sites present in the vector, subjected to exonuclease degradation, removal of the overhangs by S1 nuclease and religation. FIGS. 3A through 3B (SEQ ID NOS:3–4) shows the sequence of the entire chromosomal fragment. Two large ORFs were identified on the insert. The first ORF starts with an ATG codon at nucleotide 256 and ends with a TAA codon at nucleotide 829. Immediately downstream of this ORF is located a second ORF beginning with an ATG codon at position 872 and ending with a TAA codon at position 1708. The latter appears to correspond to the lppB gene since it is located downstream of the AhaII site at position 641 in FIGS. 3A through 3B (SEQ ID NOS:3–4) and therefore, contained on plasmid second which expressed LppB in the minicell experiment. Upstream from this ORF, there is a putative ribosome binding site GGAG and a seven base pair A/T rich spacer followed by the potential ATG start codon.

The DNA sequence was searched for nucleotide sequence homology in Genbank release 65. Sequences from position 1590 to the end of the cloned DNA in FIGS. 3A through 3B (SEQ ID NOS:3–4) showed 65.5% identity with the katF promoter region from *E. coli* (Mulvey & Loewen, 1989). The katF gene product is a putative sigmafactor which positively regulates catalase HPII (katE) and exonuclease III (xth) expression (Sask et al. 1989). It is interesting that *H. somnus* has sequences similar to katF because it lacks catalase activity (Sample & Czuprynsky, 1991).

D. Amino Acid Sequence Analysis

The ORF in the nucleotide sequence designated lppb encoded 279 amino acid residues, as indicated in FIGS. 3A through 3B (SEQ ID NOS:3–4). The molecular mass of the deduced protein was calculated to be 31307 Daltons. There is a short, hydrophobic region from amino acids 1 to 13 followed by a lipoprotein box, Leu-Ala-Ala-Cys, at the predicted signal peptidase II cleavage site. The hydrophobic-lipoprotein-box sequences strongly resembles the signal peptide of procaryotic lipoproteins, including the recently characterized lipoprotein LppA from *H. somnus*.

The lipid nature of LppB was confirmed as described above.

EXAMPLE 3

Cloning and Characterization of LppC

A genomic library of *H. somnus* DNA was constructed in *E. coli* using the expression vector pGH433, as described above. This library was screened for clones able to bind Congo red by plating cells on LB agar supplemented with ampicillin and 0.05% dye. After two days of incubation at 37° C., approximately 0.1% of the colonies turned dark red. Twenty of these colonies were screened with hyperimmune serum against *H. somnus* in a colony blot assay, and five clones were found to be seroreactive. Western blot analysis of these clones showed that three produced a 40,000 MW protein (LppB; pMS11, pMS14, pMS15), while the other two coded for proteins with molecular weights of 15,000 (pCRR22) and 60,000 (LppC; pMS10). Since Congo Red can act as an analog of porphyrin compounds and one of these clones (pMS10) produced a protein similar in size to other bacterial transferrin receptors, this clone was characterized in more detail.

The DNA insert was subcloned into the vectors pTZ18R and pTZ19R and overlapping deletions were constructed using exonuclease III. The nucleotide sequence of the insert was then determined using the chain termination method and is shown in FIGS. 4A through 4C (SEQ ID NOS:5–6). An open reading frame starting at nucleotide 108 and ending at nucleotide 1850 codes for a protein with a predicted molecular weight of approximately 65,000. The first 21 amino acids of this protein code for a typical procaryotic signal sequence and therefore the DNA coding for the mature protein likely starts at nucleotide 171. This protein has a predicted molecular weight of 63,336, close to the 60,000 MW observed on polyacrylamide gels. This difference can be accounted for by the observation that LppC is lipid modified at the first cysteine of the mature peptide. The predicted amino acid sequence of the mature peptide is shown in FIGS. 5A through 5I (SEQ ID NOS:7–9).

Another construct, pCRR27, was made by taking the insert from pMS10 and subcloning into the vector pTZ18R, giving rise to pCRR26. A HindIII digest of pCRR26 was subcloned into the HindIII site of pGH432, resulting in plasmid pCRR27. This construct gives a high level of expression of LppC.

The lipid nature of the molecule was confirmed as described above.

EXAMPLE 4

Protective Capacity of LppA and LppB

A. Antigen Preparation.

The LppA and LppB antigens were extracted from strains JM105/pMS88 and JM105/pMS103, respectively. Bacteria were grown to mid-log phase in one liter of L-broth supplemented with 50 µg/ml of ampicillin. When the absorbance at 600 nm reached 0.6, isopropyl-β,D-thiogalactoside (IPTG) was added to a final concentration of 1 mM and the cultures were incubated with vigorous agitation for 2 h at 37° C. The bacteria were harvested by centrifugation, resuspended in 40 ml of 25% sucrose/50 mM Tris-HCl buffer (pH 8) and frozen at −70° C. The frozen cells were thawed at room temperature and 10 ml of lysozyme (10 mg/ml in 250 mM Tris-HCl, pH 8) was added. After 15 minutes on ice, 300 ml of detergent mix (5 parts of 20 mM Tris-HCl, pH 7.4/300 mM sodium chloride/2% deoxycholic acid/2% Nonidet-P40 and 4 parts of 100 mM Tris-HCl, pH 8/50 mM EDTA/2% Triton X-l00) were added. The viscosity was reduced by sonication and protein aggregates were harvested by centrifugation at 27,000×g for 15 minutes. The pellets were dissolved in a minimal volume of 4 M guanidine hydrochloride. The proteins were analyzed by sodium dodecyl sulfate-polyacrylamide gel electrophoresis and the protein concentration was estimated by comparing the intensity of the Coomassie blue-stained bands to a bovine serum albumin standard.

B. Vaccine Formulation.

Each vaccine dose was prepared by mixing 100 µg of antigen, alone and in combination, with Emulsigen Plus so that the final volume was 2 ml with an adjuvant concentration of 33% (v/v). Placebo doses were prepared by combining sterile saline with Emulsigen Plus as described above. Each vaccine was mixed by sonication and stored in sterile vaccine vials at 4° C.

C. Immunization.

All calves were immunized with 2 ml of vaccine administered by intramuscular injection. After three weeks, all animals received a second vaccination as described above. The serological response to vaccination was monitored using serum samples collected prior to vaccination, on the day of the second vaccination, and 10–12 days after the second vaccination.

D. Vaccine Trial 1.

The objective of this experiment was to determine the serological response to vaccination with LppA, LppB, LppA+LppB, and a placebo. Four groups of six calves were immunized with these vaccines as described above and the serological response was determined using an enzyme-linked immunosorbent assay (ELISA). The results shown in Table 1 indicate that both antigens elicited an immune response, with LppB being the better of the two. No interference was observed when both antigens were present in the same vaccine.

E. Vaccine Trial 2.

The objective of this vaccine trial was to determine the protective capacity of LppA and LppB using an experimental challenge model. Three groups of eight calves each were vaccinated with LppA, LppB or a placebo formulated as described above. Twelve days after the second vaccination, all animals were challenged by intravenous inoculation of $1 \times 10^8$ cfu of *H. somus* strain HS25. Animals were examined daily for clinical signs of disease for 12 days post-challenge. The results are summarized in Tables 2 to 8. Immunization with LppA reduced the severity of some of the clinical signs of Haemophilosis, including lameness and the daily sick score, while immunization with LppB significantly reduced all clinical signs of disease. Therefore, both antigens appear to be useful immunogens for the prevention of *H. somnus* disease.

EXAMPLE 5

Construction of Leukotoxin-LppB Fusion Proteins

A gene fusion consisting of the *P. haemolytica* leukotoxin gene (lktA), found in plasmid pAA352 (ATCC Accession No. 68283) and LppB, was made in order to increase expression levels. Plasmid pAA352 was digested with BamHI, treated with mung bean nuclease and dephosphorylated with calf intestinal phosphatase. The plasmid pMS11 (described above), containing lppB, was digested with MaeI and AccI, and the resulting 0.855 kb fragment was filled in with DNA polymerase I klenow fragment and ligated into the pAA352 vector. Following transformation, clones which reacted with rabbit antisera against LppB in a colony immunoblot were selected, and one such clone, JM105/pCRR28, was shown to produce an IPTG-inducible protein of the correct molecular weight. The predicted nucleotide and amino acid sequence of this fusion is shown in FIGS. 5A through 5I (SEQ ID NOS:7–9).

EXAMPLE 6

Protective Capacity of LktA::LppB

A vaccine trial was conducted using the leukotoxin-LppB fusion protein from Example 5, in order to test its protective capacity. The recombinant protein was prepared from inclusion bodies as described in Example 4. The inclusion bodies were solubilized in 0.5% sodium dodecyl sulfate, and the unbound detergent was removed by dialysis against four litres of tris buffered saline for 48 hours. The proteins were analyzed by SDS-PAGE as described by Laemli (1970), and the protein concentration was estimated by comparing the intensity of the Coomassie blue-stained band to a bovine serum albumin standard (Pierce Chemical Co., Rockford, Ill.). The antigen was formulated in VSA such that the final concentration was 100 µg per ml of LktA::LppB, 30% Emulsigen Plus, 0.9% Tween-80, and 2.5 mg per ml of DDA. The dose volume was 2 cc containing 200 µg of recombinant antigen.

Three groups of eight calves each were included in the trial, and these received the LppB vaccine, Somnu-Star (formulated in VSA, obtained from BIOSTAR Inc.) as a positive control and, finally, a placebo. The vaccination and challenge schedule was as described in Example 4. The results of the trial are summarized in Table 9, and it can be seen that vaccination with Somnu-Star or LktA:LppB reduced mortality, clinical score, and weight loss. These results confirm that LppB is a protective antigen of *H. somnus*, and that fusion of the gene coding for LppB to the *P. haemolytica* leukotoxin does not diminish its protective capacity. Since *H. somnus* and *P. haemolytica* vaccines are often formulated together as combination products, this antigen has a further benefit of reducing production costs for such a vaccine.

Thus, subunit vaccines for use against *H. somnus* are disclosed, as are methods of making and using the same. Although preferred embodiments of the subject invention have been described in some detail, it is understood that obvious variations can be made without departing from the spirit and the scope of the invention as defined by the appended claims.

TABLE 1

Vaccine trial #1: Serological response to vaccination.

| Ani- | | LppA Titer | | | LppB Titer | | |
|---|---|---|---|---|---|---|---|
| mal # | Group | Bleed 1 | Bleed 2 | Bleed 3 | Bleed 1 | Bleed 2 | Bleed 3 |
| 124 | 1 | N.D. | 25600 | 6400 | 1600 | 1600 | 800 |
| 129 | 1 | 6400 | 1600 | 6400 | 400 | 1600 | 25600 |
| 134 | 1 | 6400 | 3200 | 3200 | 1600 | 3200 | 6400 |
| 190 | 1 | 400 | 3200 | 6400 | 1600 | 102400 | 25600 |
| 192 | 1 | 1600 | 51200 | 25600 | 3200 | 6400 | 6406 |
| 193 | 1 | N.D. | 25600 | 3200 | 400 | 3200 | 1600 |
| 122 | 2 | 25600 | 25600 | 102400 | | Not Done | |
| 123 | 2 | 6400 | 204800 | 819200 | | | |
| 125 | 2 | 3200 | 6400 | 102400 | | | |
| 136 | 2 | 102400 | 204800 | 204800 | | | |
| 186 | 2 | 6400 | 25600 | 51200 | | | |
| 188 | 2 | 6400 | 102400 | 6400 | | | |
| 126 | 3 | 51200 | 819200 | 51200 | 3200 | 102400 | 819200 |
| 127 | 3 | 25600 | 51200 | 51200 | 3200 | 102400 | 819200 |
| 130 | 3 | 25600 | 102400 | 819200 | 800 | 409600 | 819200 |
| 132 | 3 | 6400 | 102400 | 102400 | 800 | 204800 | 819200 |
| 133 | 3 | 102400 | 819200 | 102400 | 3200 | 51200 | 409600 |
| 137 | 3 | 6400 | 51200 | 102400 | 6400 | 51200 | 819200 |
| 128 | 4 | 25600 | 819200 | 819200 | 800 | 204800 | 819200 |
| 131 | 4 | 819200 | 102400 | 102400 | 1600 | 51200 | 819200 |
| 135 | 4 | 6400 | 102400 | 819200 | 1600 | 51200 | 819200 |
| 187 | 4 | 800 | 6400 | 102400 | 800 | 51200 | 819200 |
| 189 | 4 | 400 | 1600 | 12800 | 800 | 204800 | 819200 |
| 191 | 4 | 6400 | 51200 | 102400 | 1600 | 409600 | 819200 |

N.D. = not done
Group 1 = Placebo
Group 2 = LppA
Group 3 = LppB
Group 4 = LppA + LppB

TABLE 2

Vaccine Trial #2: Cumulative Weight Change Per Group

| Day | Placebo | Vac LppA | VacLppB |
|---|---|---|---|
| 1 | −10.4 | −7.7 | −3.5 |
| 2 | −8.6 | −6.3 | −3.5 |
| 3 | −10.4 | −9.9 | −4.3 |
| 4 | −14.4 | −13.7 | −7.1 |
| 5 | −10.8 | −9.4 | −4.3 |
| 6 | −16.2 | −12.7 | −7.8 |
| 7 | −22 | −18.4 | −11.9 |
| 8 | −22.8 | −17.2 | −12.4 |
| 9 | −24.6 | −20.7 | −14.4 |
| 10 | −23.8 | −21.5 | −14.7 |
| 11 | −24 | −22.5 | −15.6 |
| 12 | −27.4 | −24.5 | −16.7 |
| Mean | −2.28333 | −2.041667 | −1.391667 |
| Max | −27.4 | −24.5 | −16.7 |

TABLE 3

Vaccine Trial #2: Average Daily Temperatures Per Group

| Day | Placebo | Vac LppA | VacLppB |
|---|---|---|---|
| 1 | 39.91 | 39.69 | 39.3 |
| 2 | 39.53 | 39.47 | 39.3 |
| 3 | 39.56 | 39.64 | 39.33 |
| 4 | 39.2 | 39.43 | 39.18 |
| 5 | 39.3 | 39.25 | 39.41 |
| 6 | 38.98 | 39.08 | 39.06 |
| 7 | 39.16 | 39.15 | 39.15 |
| 8 | 39.22 | 39.12 | 38.86 |
| 9 | 38.98 | 39.35 | 38.95 |
| 10 | 39 | 39.42 | 38.83 |
| 11 | 39.2 | 39.37 | 38.98 |
| 12 | 39.38 | 39.13 | 38.86 |
| Mean | 39.285 | 39.34167 | 39.10083 |
| Max | 39.91 | 39.69 | 39.41 |

TABLE 4

Vaccine Trial #2: Average Daily Lameness Score Per Group

| Day | Placebo | Vac LppA | VacLppB |
|---|---|---|---|
| 1 | 0 | 0 | 0 |
| 2 | 0.25 | 0 | 0 |
| 3 | 0.2 | 0.143 | 0.063 |
| 4 | 0.2 | 0.083 | 0.125 |
| 5 | 0.2 | 0 | 0.188 |
| 6 | 0.3 | 0.167 | 0.25 |
| 7 | 0.9 | 0.333 | 0.25 |
| 8 | 1.1 | 0.583 | 0.375 |
| 9 | 1 | 0.583 | 0.688 |
| 10 | 1 | 0.5 | 0.625 |
| 11 | 1 | 0.167 | 0.5 |
| 12 | 1.1 | 0.583 | 0.438 |
| Mean | 0.604167 | 0.261833 | 0.291833 |
| Max | 1.1 | 0.583 | 0.688 |

TABLE 5

Vaccine Trial #2: Average Daily Sick Score Per Group

| Day | Placebo | Vac LppA | VacLppB |
|---|---|---|---|
| 1 | 0.3 | 0.2 | 0.1 |
| 2 | 0.5 | 0.1 | 0.1 |
| 3 | 0.4 | 0.5 | 0 |
| 4 | 0.3 | 0.3 | 0 |
| 5 | 0.2 | 0.2 | 0.1 |
| 6 | 0.2 | 0.3 | 0.1 |
| 7 | 0.5 | 0.3 | 0.2 |
| 8 | 0.6 | 0.5 | 0.1 |
| 9 | 0.7 | 0.7 | 0.6 |
| 10 | 0.6 | 0.7 | 0.3 |
| 11 | 0.7 | 0.4 | 0.3 |
| 12 | 0.8 | 0.3 | 0.2 |
| Mean | 0.483333 | 0.375 | 0.175 |
| Max | 0.8 | 0.7 | 0.6 |

TABLE 6

Vaccine Trial #2: Daily Number of Calves with Fevers*

| Day | Placebo | Vac LppA | VacLppB |
|---|---|---|---|
| 1 | 3 | 3 | 1 |
| 2 | 1 | 1 | 1 |
| 3 | 2 | 2 | 0 |
| 4 | 1 | 2 | 0 |
| 5 | 0 | 1 | 0 |
| 6 | 0 | 1 | 0 |
| 7 | 0 | 1 | 0 |
| 8 | 1 | 1 | 0 |
| 9 | 0 | 2 | 0 |
| 10 | 0 | 1 | 0 |
| 11 | 1 | 1 | 0 |
| 12 | 0 | 1 | 0 |
| Daily Maximum | 3 | 3 | 1 |
| Total | 9 | 17 | 2 |

*Temperature >= 40.0

TABLE 7

Vaccine Trial #2: Daily Number of Calves Sick*

| Day | Placebo | Vac LppA | VacLppB |
|---|---|---|---|
| 1 | 4 | 4 | 1 |
| 2 | 4 | 2 | 1 |
| 3 | 5 | 3 | 0 |
| 4 | 4 | 4 | 0 |
| 5 | 4 | 3 | 1 |
| 6 | 4 | 4 | 1 |
| 7 | 6 | 4 | 2 |
| 8 | 7 | 5 | 1 |
| 9 | 7 | 6 | 5 |
| 10 | 7 | 6 | 3 |
| 11 | 7 | 5 | 3 |
| 12 | 7 | 4 | 2 |
| Daily Maximum | 7 | 6 | 5 |
| Total | 62 | 46 | 19 |

*Clinical Sick Score > 0
(Dead animals counted as sick)

TABLE 8

Vaccine Trial #2: Summary of Clinical Findings
Protection Against *H. somnus* Challenge by Subunit Vaccines

| Vaccines | Calves | Died | Sick | Febrile |
|---|---|---|---|---|
| Placebo | 8 | 3 | 7 | 5 |
| Vaccine LppA | 8 | 2 | 7 | 5 |
| Vaccine LppB | 8 | 0 | 5 | 2 |

TABLE 9

Summary of the LktA::LppB vaccine trial

| Group | Mortality | Mean clinical score | Weight change (kg) | Serological response LppB | Serological response Somnu-Star |
|---|---|---|---|---|---|
| Placebo | 2/8 | 1.13 | −5.75 | 5,800 | 8,694 |
| Somnu-Star | 0/8 | 0.38 | −2.38 | 3,201 | 115,057 |
| LktA:LppB | 0/8 | 0.75 | −2.25 | 85,730 | 29,373 |

We claim:

1. An isolated nucleotide sequence encoding an immunogenic *Haemophilus somnus* LppB polypeptide, wherein said sequence comprises (a) a nucleotide sequence as set forth at positions 872 through 1708 of FIGS. 3A through 3B (SEQ ID NO:3), or (b) a nucleotide sequence comprising at least 45 nucleotides that hybridizes to (a) in a hybridization reaction performed under stringent conditions, and further wherein the isolated nucleotide sequence is flanked by sequences that do not flank the coding sequence in the *H. somnus* genome.

2. An isolated nucleotide sequence encoding an immunogenic *Haemophilus sominus* LppB polypeptide, wherein said sequence comprises (a) a nucleotide sequence as set forth at positions 920 through 1708 of FIGS. 3A through 3B (SEQ ID NO:3), or (b) a nucleotide sequence comprising at least 45 nucleotides that hybridizes to (a) in a hybridization reaction performed under stringent conditions, and further wherein the isolated nucleotide sequence is flanked by sequences that do not flank the coding sequence in the *H. somnus* genome.

3. An isolated nucleotide sequence encoding an immunogenic *Haemophilus somnus* LppB polypeptide, wherein said sequence comprises (a) a nucleotide sequence as set forth at positions 256 through 829 of FIGS. 3A through B (SEQ ID NO:3), or (b) a nucleotide sequence comprising at least 45 nucleotides that hybridizes to (a) in a hybridization reaction performed under stringent conditions, and further wherein the isolated nucleotide sequence is flanked by sequences that do not flank the coding sequence in the *H. somnus* genome.

4. A recombinant vector comprising:
   (a) a nucleotide sequence according to claim 1; and
   (b) control sequences that are operably linked to said nucleotide sequence whereby said nucleotide sequence can be transcribed and translated in a host cell, and at least one of said control sequences is heterologous to said nucleotide sequence.

5. A host cell transformed with the recombinant vecotr of claim 4.

6. A method of producing a recombinant polypeptide comprising:
   (a) providing a population of host cells according to claim 5; and
   (b) culturing said population of cells such that the polypeptide encoded by said nucleotide sequence is expressed.

7. An isolated nucleotide sequence comprising a coding sequence for an immunogenic *Haemophilus somnus* LppB protein as present in plasmid pMS103 (ATCC Accession Number 68957, wherein the isolated nucleotide sequence is flanked by sequences that do not flank the coding sequence in the *H. somnus* genome.

8. A recombinant vector comprising:

(a) a nucleotide sequence according to claim 7; and (b) control sequences that are operably linked to said nucleotide sequence whereby said nucleotide sequence can be transcribed and translated in a host cell, and at least one of said control sequences is heterologous to said nucleotide sequence.

9. A host cell transformed with the recombinant vector of claim 8.

10. A method of producing a recombinant polypeptide comprising:

(a) providing a population of host cells according to claim 9; and (b) culturing said population of cells such that the polypeptide encoded by said nucleotide sequence is expressed.

11. A recombinant vector comprising:

(a) a nucleotide sequence according to claim 3; and (b) control sequences that are operably linked to said nucleotide sequence whereby said nucleotide sequence can be transcribed and translated in a host cell, and at least one of said control sequences is heterologous to said nucleotide sequence.

12. A host cell transformed with the recombinant vector of claim 11.

13. A method of producing a recombinant polypeptide comprising:

(a) providing a population of host cells according to claim 12; and (b) culturing said population of cells such that the polypeptide encoded by said nucleotide sequence is expressed.

14. A recombinant vector comprising:

(a) a nucleotide sequence according to claim 2; and (b) control sequences that are operably linked to said nucleotide sequence whereby said nucleotide sequence can be transcribed and translated in a host cell, and at least one of said control sequences is heterologous to said nucleotide sequence.

* * * * *